(12) United States Patent
Dyatkin et al.

(10) Patent No.: US 9,735,373 B2
(45) Date of Patent: Aug. 15, 2017

(54) ORGANIC ELECTROLUMINESCENT MATERIALS AND DEVICES

(71) Applicants: Alexey Dyatkin, Ambler, PA (US); Chuanjun Xia, Lawrenceville, NJ (US); David Zenan Li, Princeton, NJ (US)

(72) Inventors: Alexey Dyatkin, Ambler, PA (US); Chuanjun Xia, Lawrenceville, NJ (US); David Zenan Li, Princeton, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 737 days.

(21) Appl. No.: 13/914,124

(22) Filed: Jun. 10, 2013

(65) Prior Publication Data
US 2014/0361252 A1  Dec. 11, 2014

(51) Int. Cl.
| H01L 51/54 | (2006.01) |
| C09K 11/06 | (2006.01) |
| H01L 51/00 | (2006.01) |
| C07F 5/06 | (2006.01) |
| H01L 51/50 | (2006.01) |

(52) U.S. Cl.
CPC .......... *H01L 51/0081* (2013.01); *C07F 5/069* (2013.01); *H01L 51/0085* (2013.01); *H01L 51/5028* (2013.01)

(58) Field of Classification Search
None
See application file for complete search history.

(56) References Cited

U.S. PATENT DOCUMENTS

| 4,769,292 | A | 9/1988 | Tang et al. |
| 5,061,569 | A | 10/1991 | VanSlyke et al. |
| 5,141,671 | A | 8/1992 | Bryan et al. |
| 5,150,006 | A | 9/1992 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0151042 | A1 | 8/2003 | Hueschen |
| 2003/0152802 | A1 | 8/2003 | Tsuboyama et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |

(Continued)

FOREIGN PATENT DOCUMENTS

| EP | 0650955 | 5/1995 |
| EP | 1725079 | 11/2006 |

(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
Aonuma, Masaki et al., "Material Design of Hole Transport Materials Capable of Thick-Film Formation in Organic Light Emitting Diodes," Appl. Phys. Lett., 90:183503-1-183503-3, Year: 2007.
Baldo et al., Highly Efficient Phosphorescent Emission from Organic Electroluminescent Devices, Nature, vol. 395, 151-154, (1998).
Baldo et al., Very high-efficiency green organic light-emitting devices based on electrophosphorescence, Appl. Phys. Lett., vol. 75, No. 3, 4-6 (1999).

(Continued)

*Primary Examiner* — Andrew K Bohaty
(74) *Attorney, Agent, or Firm* — Duane Morris LLP

(57) ABSTRACT

Aluminum chelate complex compounds with two substituted 8-hydroxyquinoline ligand and one dibenzothiophene, dibenzofuran or dibenzoselenophene ligands or aza-analogs of these molecules, attached directly or through an aromatic spacer to the oxygen atom is provided to improve lifetime, operating voltage and efficiency of an OLED. Additional substitution of dibenzothiophene or dibenzofuran ring may also provide charge delocalization, HOMO modification and higher Tg.

25 Claims, 3 Drawing Sheets

(56) References Cited

U.S. PATENT DOCUMENTS

| | | | |
|---|---|---|---|
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0134514 A1* | 6/2007 | Kondakov .......... | H01L 51/0079 428/690 |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Pakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2009/0206327 A1* | 8/2009 | Radu .................. | C07F 5/069 257/40 |
| 2010/0090241 A1* | 4/2010 | D'Andrade ......... | H01L 27/3211 257/98 |
| 2011/0127510 A1* | 6/2011 | Seo .................... | H01L 51/0052 257/40 |
| 2013/0134402 A1* | 5/2013 | Tanaka ................ | H01L 51/5004 257/40 |

FOREIGN PATENT DOCUMENTS

| | | | |
|---|---|---|---|
| EP | 2034538 | 3/2009 | |
| JP | 2004359671 | 12/2004 | |
| JP | 200511610 | 1/2005 | |
| JP | 2007123392 | 5/2007 | |
| JP | 2007254297 | 10/2007 | |
| JP | 2008074939 | 4/2008 | |
| JP | WO 2012005329 A1 * | 1/2012 | ......... H01L 51/5004 |
| KR | 2010114749 | 10/2010 | |
| WO | 0139234 | 5/2001 | |
| WO | 0202714 | 1/2002 | |
| WO | 0215645 | 2/2002 | |
| WO | 03040257 | 5/2003 | |
| WO | 03060956 | 7/2003 | |
| WO | 2004093207 | 10/2004 | |
| WO | 2004107822 | 12/2004 | |
| WO | 2005014551 | 2/2005 | |
| WO | 2005019373 | 3/2005 | |
| WO | 2005030900 | 4/2005 | |
| WO | 2005089025 | 9/2005 | |
| WO | 2005123873 | 12/2005 | |
| WO | 2006009024 | 1/2006 | |
| WO | 2006056418 | 6/2006 | |
| WO | 2006072002 | 7/2006 | |
| WO | 2006082742 | 8/2006 | |
| WO | 2006098120 | 9/2006 | |
| WO | 2006100298 | 9/2006 | |
| WO | 2006103874 | 10/2006 | |
| WO | 2006114966 | 11/2006 | |
| WO | 2006132173 | 12/2006 | |
| WO | 2007002683 | 1/2007 | |
| WO | 2007004380 | 1/2007 | |
| WO | 2007063754 | 6/2007 | |
| WO | 2007063796 | 6/2007 | |
| WO | 2008056746 | 5/2008 | |
| WO | 2008101842 | 8/2008 | |
| WO | 2008132085 | 11/2008 | |
| WO | 2008153338 | 12/2008 | |
| WO | 2009000673 | 12/2008 | |
| WO | 2009003898 | 1/2009 | |
| WO | 2009008311 | 1/2009 | |
| WO | 2009018009 | 2/2009 | |
| WO | 2009050290 | 4/2009 | |
| WO | 2009021126 | 5/2009 | |
| WO | 2009062578 | 5/2009 | |
| WO | 2009063833 | 5/2009 | |
| WO | 2009066778 | 5/2009 | |
| WO | 2009066779 | 5/2009 | |
| WO | 2009086028 | 7/2009 | |
| WO | 2009100991 | 8/2009 | |

OTHER PUBLICATIONS

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4''-Tri(N-carbazolyl)triphenylamine (TCTA) and 4,4',4''-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

(56) References Cited

OTHER PUBLICATIONS

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5''-Bis(dimesitylboryl)-2,2'5',2''-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based On Silole Derivatives And Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74:985-991 (1997).

Sotoyama, Wataru et al., "Efficient Organic Light-Emitting Diodes with Phosphorescent Platinum Complexes Containing NN^C^N C N^C^N N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes Of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69(15):2160-2162 (1996).

Wang, Y. et al., "Highly Efficient Electroluminescent Materials Based on Fluorinated Organomettallic Iridium Compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Chu et al., "Characterization of electronic structure of aluminum (III) bis(2-methyl-8-quninolinato)-4-phenylphenolate (BAlq) for phosphorescent organic light emitting devices," Chem. Physics Lett. 404 (2005), 121-125.

Bolivar et al., "True Blue: Blue-Emitting Aluminum (III) Quinolinolate Complexes," Inorganic Chemistry (2006) 45(24), 9610-9612.

* cited by examiner

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to organic light emitting devices. More specifically, the present disclosure pertains to compounds for use as emitter hosts or electron transporting materials in organic light emitting devices and organic light emitting devices including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

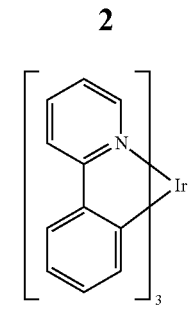

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher"

HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound is provided that has the structure of Formula I shown below

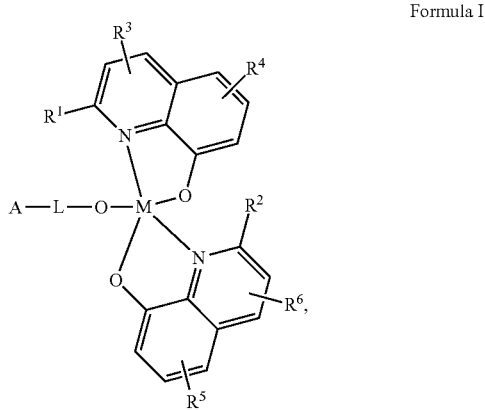

Formula I wherein M is a group III element;
wherein L is a single bond or comprises an aryl or heteroaryl group having from 5-20 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof;
wherein A contains a group selected from the group consisting of dibenzothiophene, dibenzoselenophene, dibenzofuran, aza-dibenzofuran, aza-dibenzothiophene, aza-dibenzoselenophene, and combination thereof, which are optionally further substituted with one or more groups selected from hydrogen, deuterium, alkyl, cycloalkyl, aralkyl, alkoxy, aryloxy, amino, silyl, aryl, heteroaryl, and combinations thereof;
wherein $R^3$, $R^6$ each represent mono, di substitutions, or no substitution;
wherein $R^4$, $R^5$ each represent mono, di, tri substitutions, or no substitution; and
wherein $R^1$, $R^2$, $R^3$, $R^4$, $R^5$ and $R^6$ are each independently selected from the group consisting of hydrogen, deuterium, alkyl, cycloalkyl, aralkyl, alkoxy, aryloxy, amino, silyl, aryl, heteroaryl, and combinations thereof.

According to another embodiment, a first device comprising a first organic light emitting device is also provided.

The first device can include an anode, a cathode, and an organic layer, disposed between the anode and the cathode. The organic layer can include a compound of Formula I. The first device can be a consumer product, an organic light-emitting device, and/or a lighting panel.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
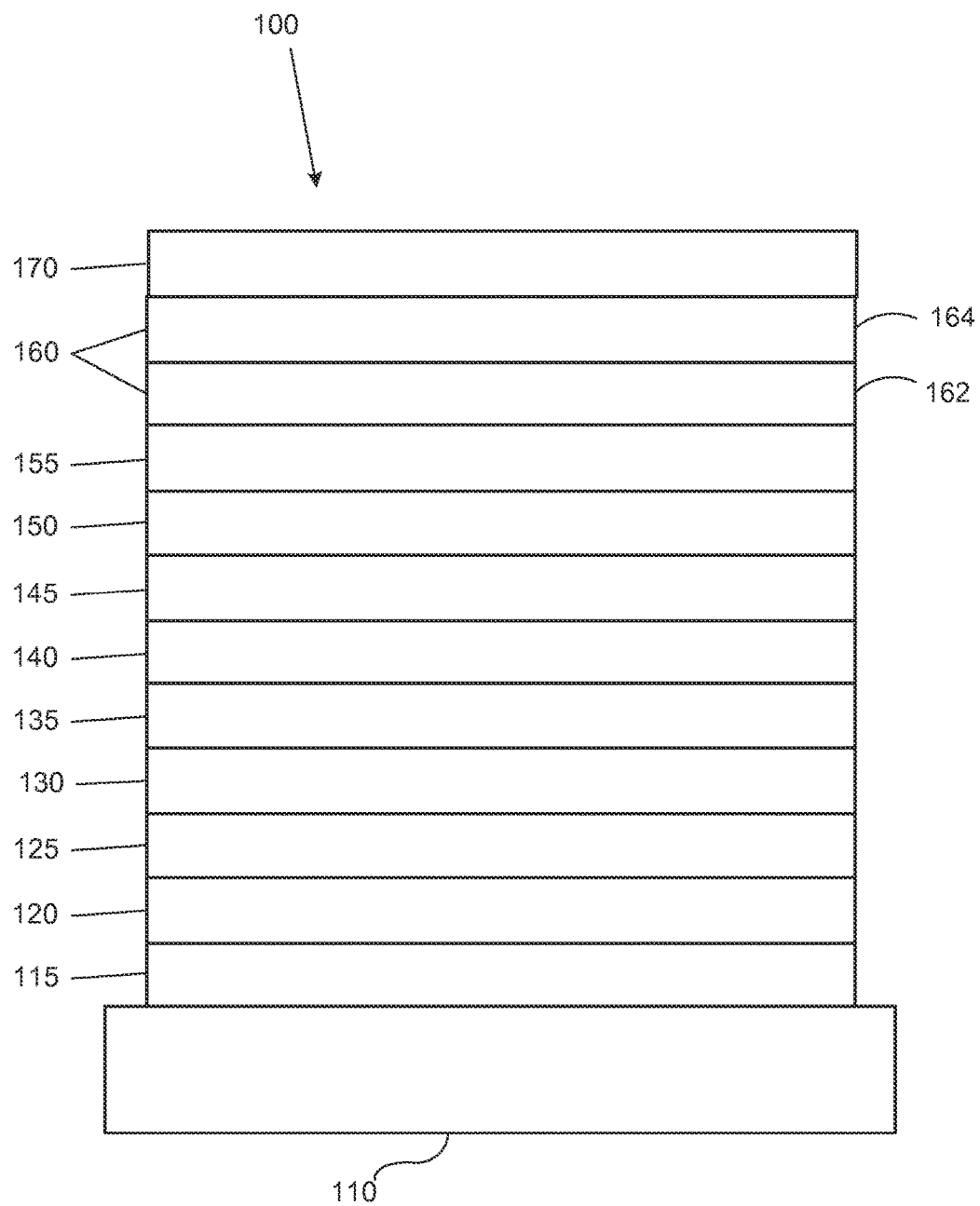
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
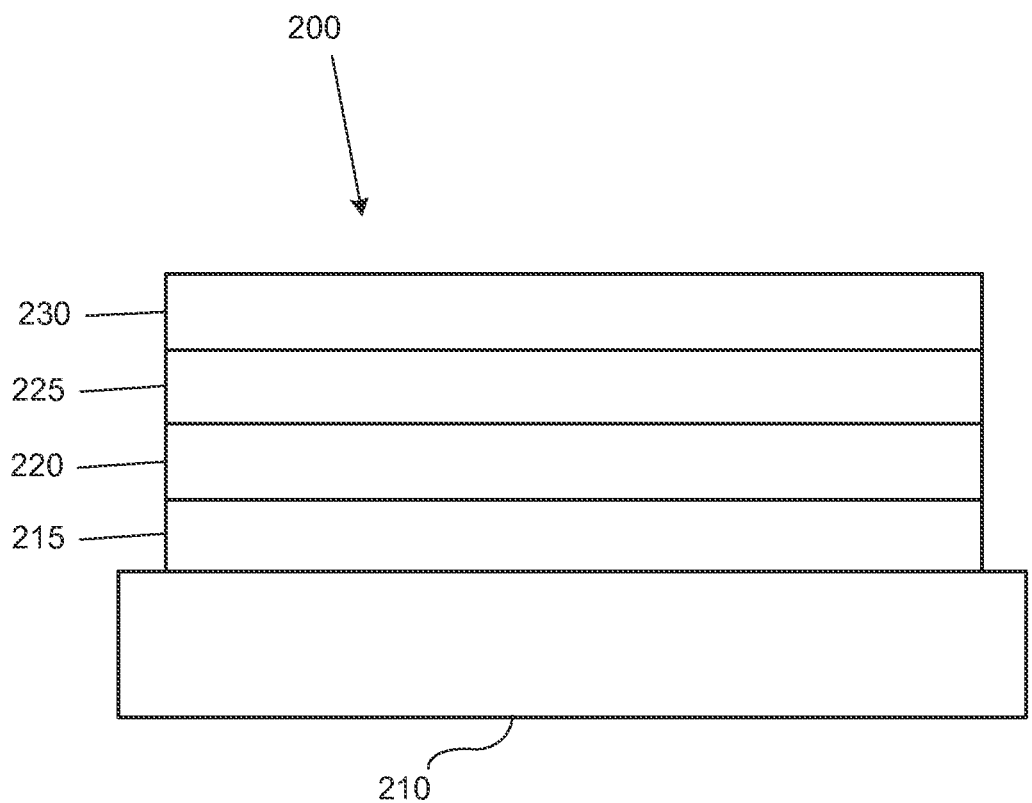
FIG. 2 shows an inverted organic light emitting device that does not have a separate electron transport layer.
Figure 3:
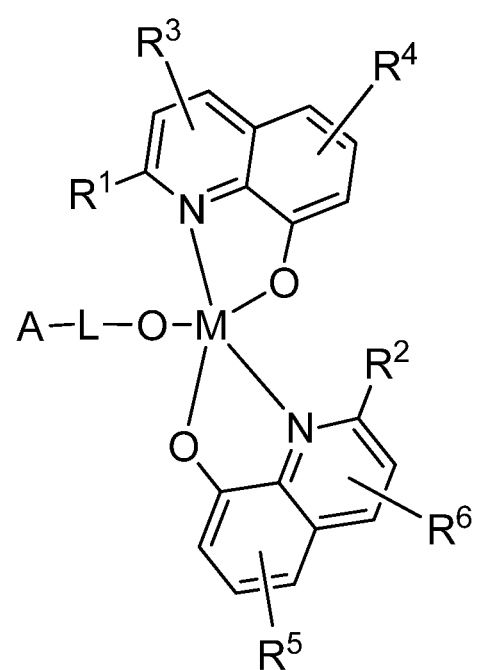
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention may be incorporated into a wide variety of consumer products, including flat panel displays, computer monitors, medical monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, aralkyl, heterocyclic group, aryl, aromatic group, and heteroaryl are known to the art, and are defined in U.S. Pat. No. 7,279,704 at cols. 31-32, which are incorporated herein by reference.

As used herein, "substituted" indicates that a substituent other than H is bonded to the relevant carbon. Thus, where $R^2$ is monosubstituted, then one $R^2$ must be other than H. Similarly, where $R^3$ is disubstituted, then two of $R^3$ must be other than H. Similarly, where $R^2$ is unsubstituted $R^2$ is hydrogen for all available positions.

Al complexes with bidentate ligands like Alq$_3$ ([tris-(8-hydroxyquinoline)aluminum] are widely used in OLED devices as hosts and ETL materials. In an attempt to improve the property of this material, BAlq, aluminum (III) bis(2-methyl-8-quinolinato-4-phenylphenolate was prepared. This compound demonstrated better properties than parent Alq. Calculations concluded that HOMO and LUMO orbitals of BAlq are mainly localized on 4-phenylphenol and 2-methyl-8-hydroxyquinoline ligands respectively. (See Ta-Ya Chu, et al., "Characterization of electronic structure of aluminum (III) bis(2-methyl-8-quninolinato)-4-pheynylphenolate (BAlq) for phosphorescent organic light emitting devices," Chem. Physics Lett. 404, (2005), 121-125).

Modification of the phenol ligand is a good way to improve charge-carrying properties of the material. The inventors discovered that introduction in the molecule of hydroxyl-substituted heteroaromatic compound derived from substituted or non-substituted dibenzothiophene (DBT), dibenzofurane (DBF), or their aza-analogs, may be a good way to achieve that goal. Although DBT and DBF are common building blocks in the construction of OLED materials, Al complexes with these types of ligands have not been reported. Our goal was to improve electron-conducting properties of the host material, so the inventors introduced groups which are known to be good electron-carriers.

The "aza" designation in the fragments described above, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

Another potential benefit of replacing byphenyl ligand by DBT or DBF derivative can be increased glass transition temperature, Tg, an important property of OLED materials. BAlq and it's close analogs are widely used in industry. However, these materials have low Tg; the structure does not permit optimization of charge-carrier properties. Introduction of DBT, DBF fragments or their aza-analogs may tune HOMO level of the molecule and tune-up the charge balance of the device. These tune-up may improve device properties.

The compounds disclosed herein are suitable as hosts in emissive layers, electron transporting materials, or hole blocking materials in OLEDs, particularly for red devices.

According to an embodiment, a compound is provided that has the structure of Formula I shown below

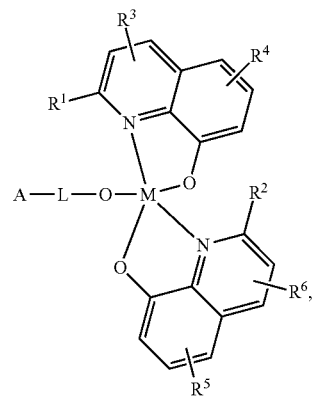

Formula I wherein M is a group III element; L is a single bond or comprises an aryl or heteroaryl group having from 5-20 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof; wherein A contains a group selected from the group consisting of dibenzothiophene, dibenzoselenophene, dibenzofuran, aza-dibenzofuran, aza-dibenzothiophene, aza-dibenzoselenophene, and combination thereof, which are optionally further substituted with one or more groups selected from hydrogen, deuterium, alkyl, cycloalkyl, aralkyl, alkoxy, aryloxy, amino, silyl, aryl, heteroaryl, and combinations thereof; $R^3$, $R^6$ each represent mono, di substitutions, or no substitution; $R^4$, $R^5$ each represent mono, di, tri substitutions, or no substitution; and wherein $R^1$, $R^2$, $R^3$, $R^4$, $R^5$ and $R^6$ are each independently selected from the group consisting of hydrogen, deuterium, alkyl, cycloalkyl, aralkyl, alkoxy, aryloxy, amino, silyl, aryl, heteroaryl, and combinations thereof.

In one embodiment, $R^1$ and $R^2$ are each independently selected from the group consisting of hydrogen, deuterium, methyl, ethyl, propyl, iso-propyl, and combinations thereof.

According to an embodiment, M in Formula I is selected from the group consisting of Al, In and Ga. L in Formula I can be selected from the group consisting of single bond,
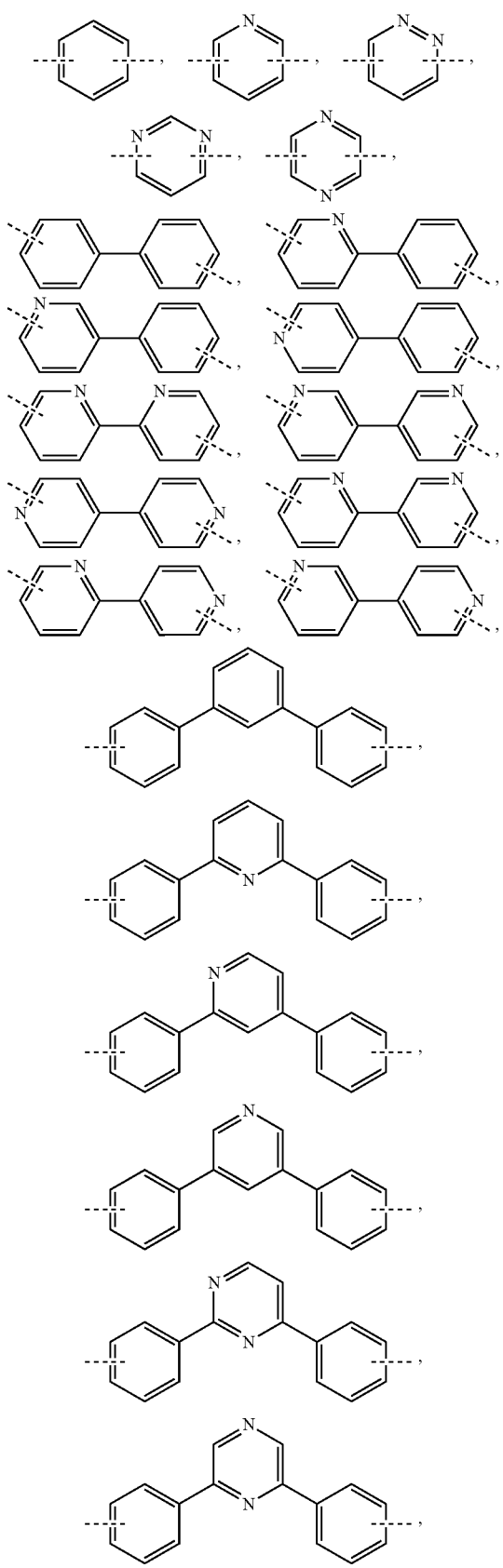
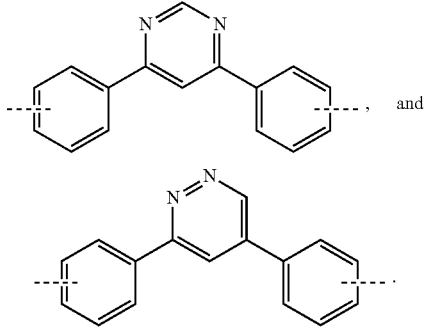
In one embodiment, A in Formula I is selected from the group consisting of:
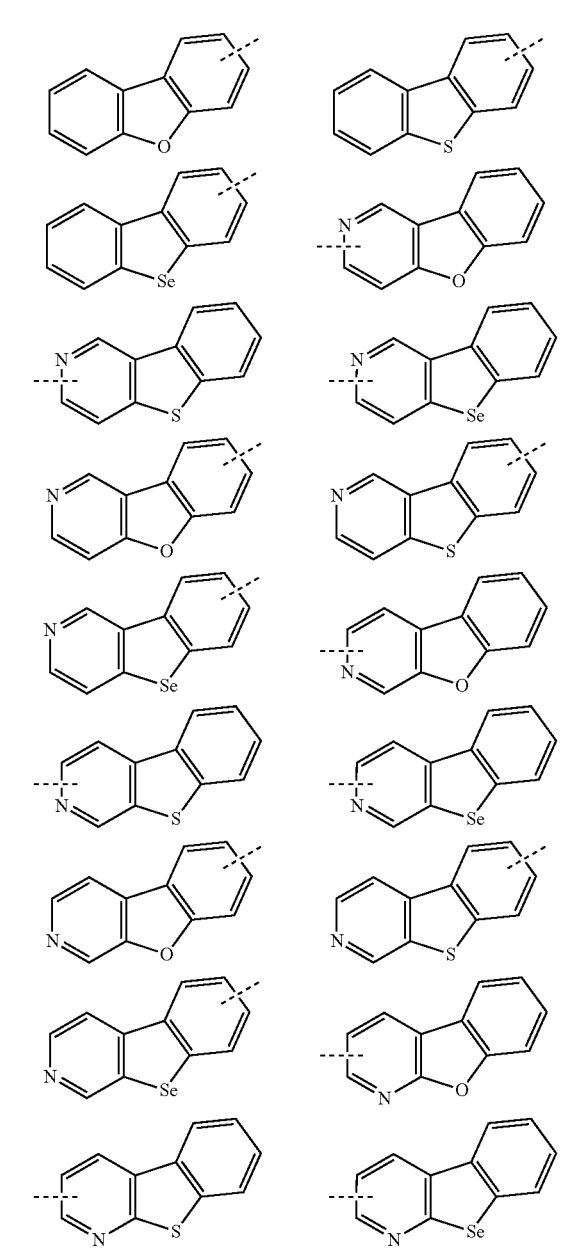

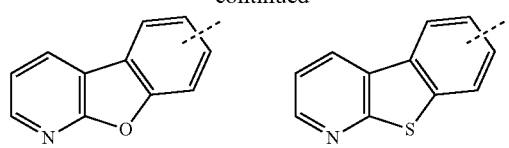
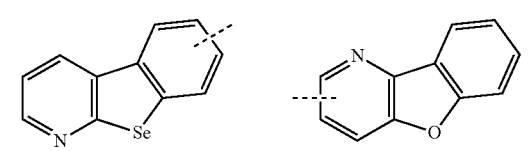
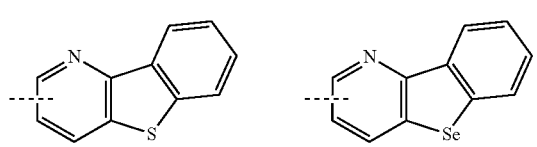
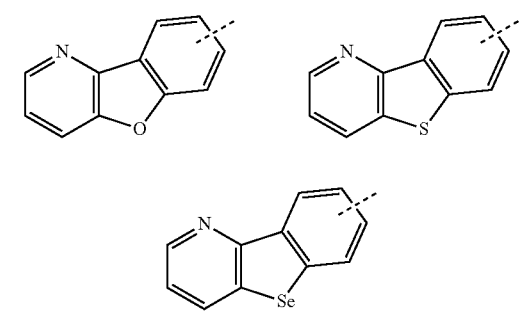
In one preferred embodiment, the compound of Formula I can be selected from the group consisting of
Compound 3
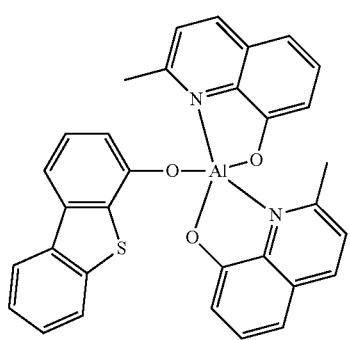
Compound 17
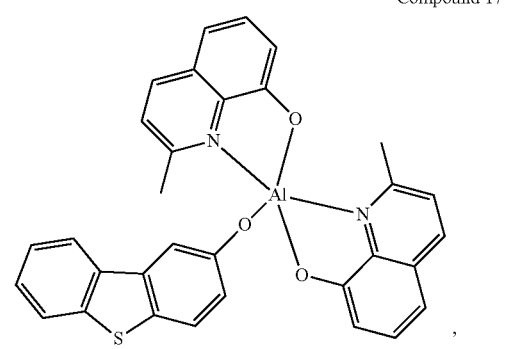
Compound 31
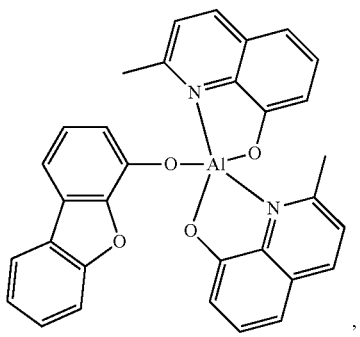
Compound 45
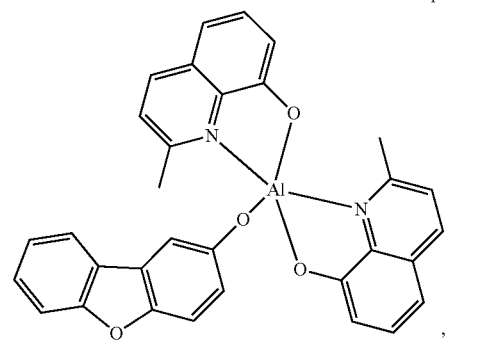
Compound 58
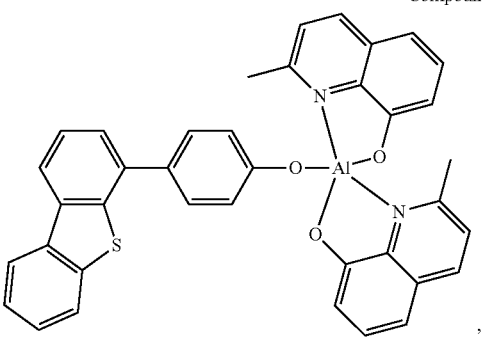
Compound 72
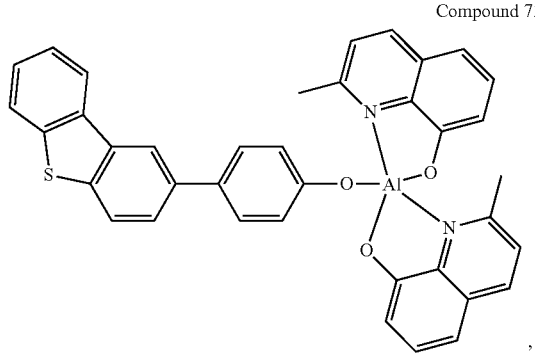

Compound 86
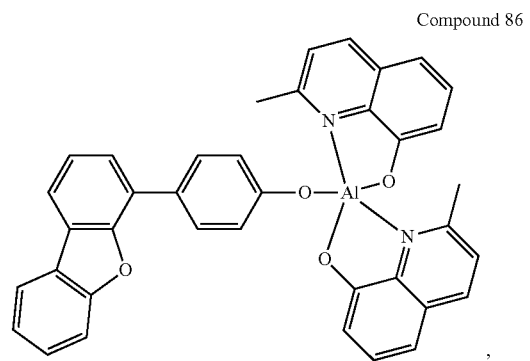
Compound 100
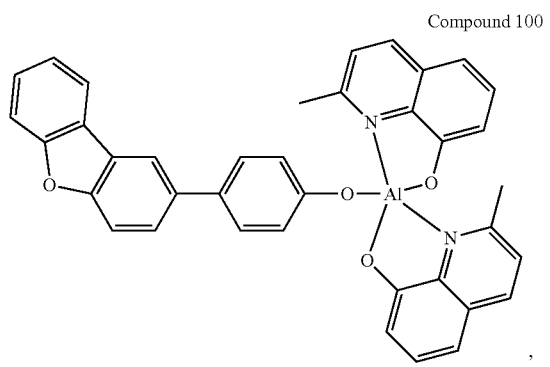
Compound 115
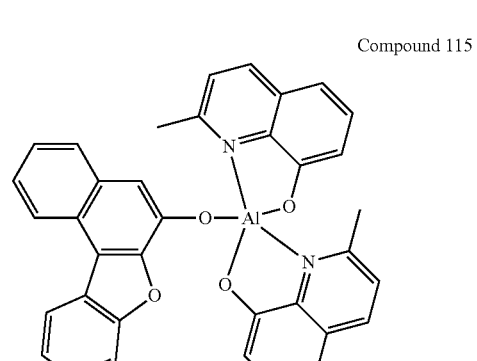
Compound 116
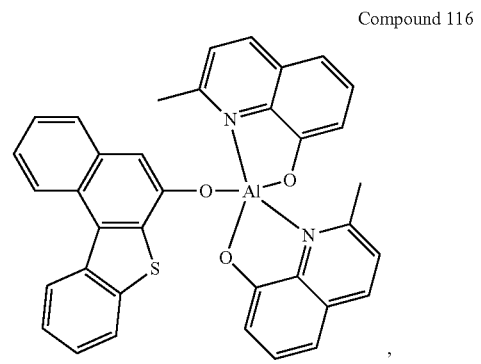
Compound 119
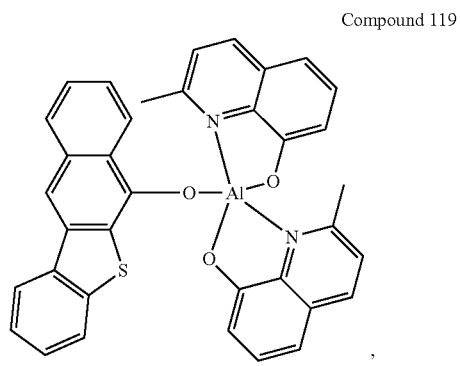
Compound 120
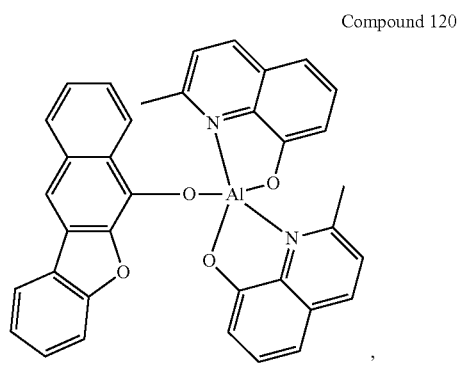
Compound 121
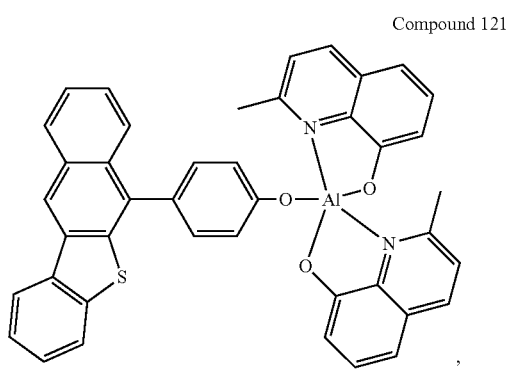
Compound 122
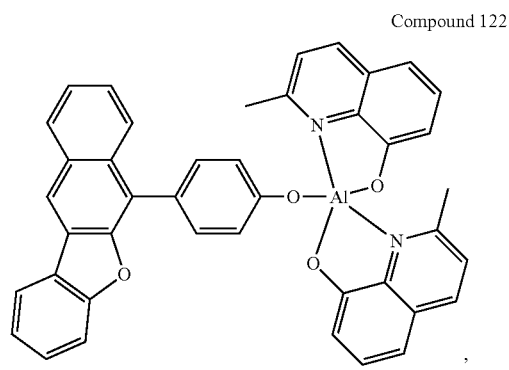

Compound 123
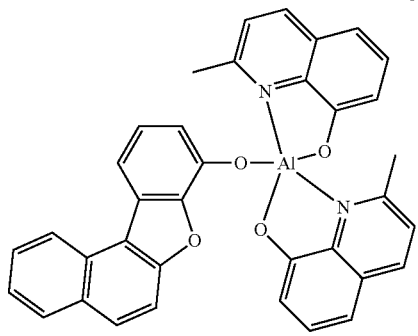

Compound 124
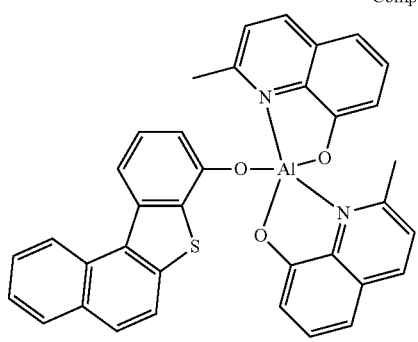

Compound 127
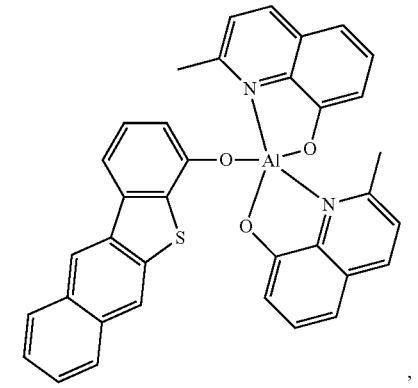

Compound 128
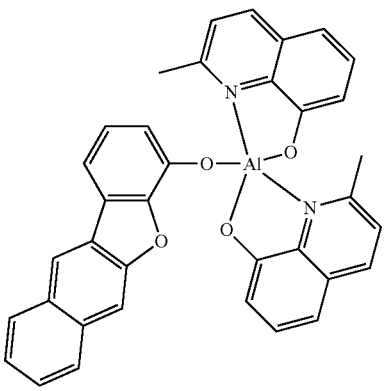

, and

Compound 131
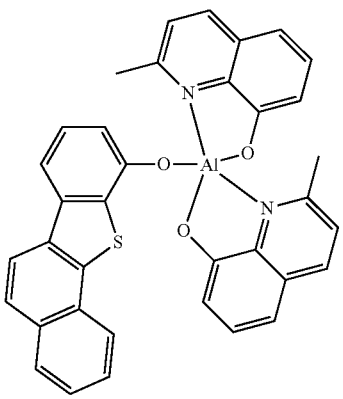

According to another embodiment, the compound having the structure according to Formula I is selected from the group consisting of Compound 1 through Compound 208 listed in TABLE 1 below, wherein R¹, R², L and A are as defined and wherein Me is methyl, H is hydrogen, Et is ethyl, and i-Pr is iso-propyl.

TABLE 1

| Compound number | R¹ | R² | L | A |
|---|---|---|---|---|
| 1 | Me | H | single bond | 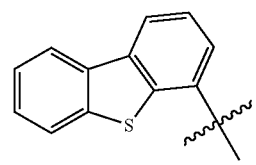 [SMILES: *c1cccc2c1sc1ccccc12] |
| 2 | H | H | single bond | 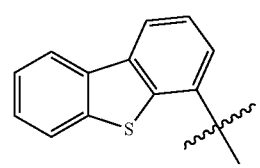 |

TABLE 1-continued
| Compound number | R¹ | R² | L | A |
|---|---|---|---|---|
| 3 | Me | Me | single bond | 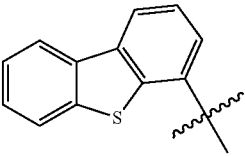 [SMILES: *c1cccc2c1sc1ccccc12] |
| 4 | Me | Et | single bond | 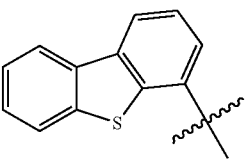 [SMILES: *c1cccc2c1sc1ccccc12] |
| 5 | Me | i-Pr | single bond | 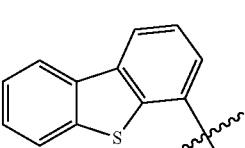 |
| 6 | Et | i-Pr | single bond | 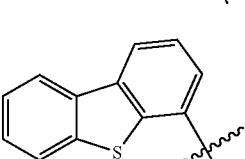 |
| 7 | H | i-Pr | single bond | 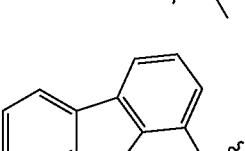 |
| 8 | Me | H | single bond | 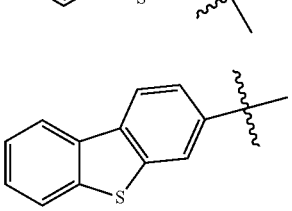 |
| 9 | H | H | single bond | 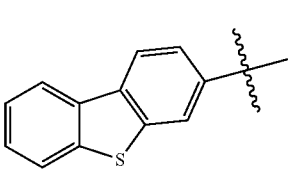 |
| 10 | Me | Me | single bond | 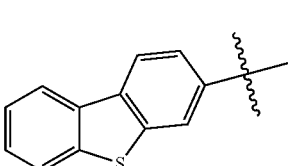 |
| 11 | Me | Et | single bond | 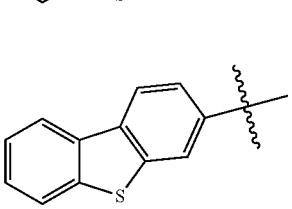 |

TABLE 1-continued
| Compound number | R¹ | R² | L | A |
|---|---|---|---|---|
| 12 | Me | i-Pr | single bond | 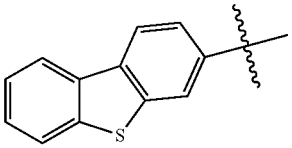 [SMILES: *c1ccc2c(c1)sc1ccccc12] |
| 13 | Et | i-Pr | single bond | 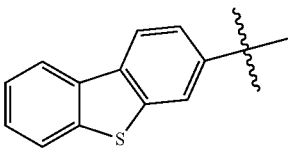 |
| 14 | H | i-Pr | single bond | 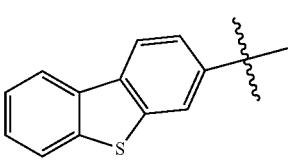 |
| 15 | Me | H | single bond |  |
| 16 | H | H | single bond | 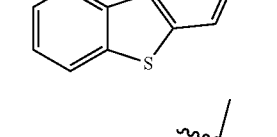 |
| 17 | Me | Me | single bond | 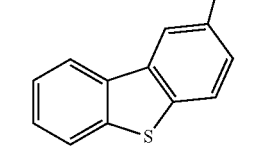 |
| 18 | Me | Et | single bond |  |
| 19 | Me | i-Pr | single bond | 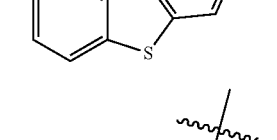 |

TABLE 1-continued
| Compound number | R¹ | R² | L | A |
|---|---|---|---|---|
| 20 | Et | i-Pr | single bond | 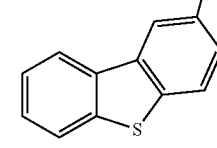 |
| 21 | H | i-Pr | single bond | 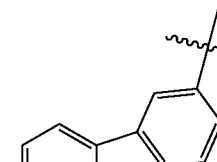 |
| 22 | Me | H | single bond | 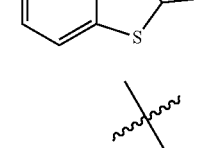 |
| 23 | H | H | single bond | 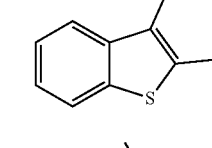 |
| 24 | Me | Me | single bond | 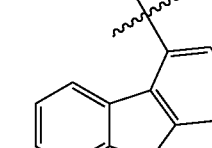 |
| 25 | Me | Et | single bond | 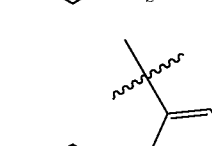 |
| 26 | Me | i-Pr | single bond | 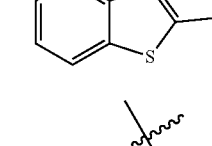 |

TABLE 1-continued
| Compound number | R¹ | R² | L | A |
|---|---|---|---|---|
| 27 | Et | i-Pr | single bond | 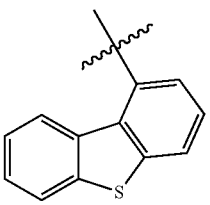 [SMILES: *c1cccc2sc3ccccc3c12] |
| 28 | H | i-Pr | single bond | 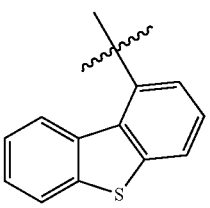 [SMILES: *c1cccc2sc3ccccc3c12] |
| 29 | Me | H | single bond | 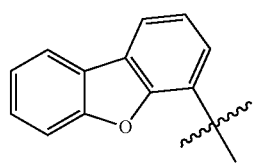 [SMILES: *c1cccc2c1oc1ccccc12] |
| 30 | H | H | single bond | 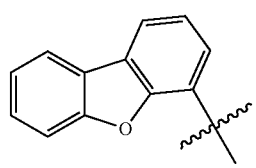 [SMILES: *c1cccc2c1oc1ccccc12] |
| 31 | Me | Me | single bond | 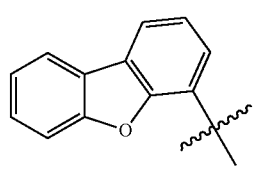 [SMILES: *c1cccc2c1oc1ccccc12] |
| 32 | Me | Et | single bond | 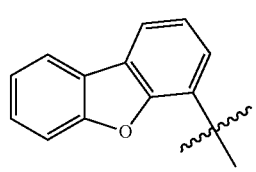 [SMILES: *c1cccc2c1oc1ccccc12] |
| 33 | Me | i-Pr | single bond | 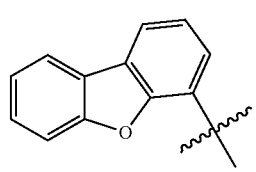 |
| 34 | Et | i-Pr | single bond | 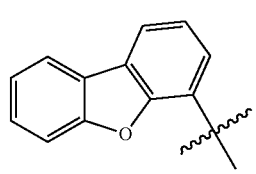 |

TABLE 1-continued

| Compound number | R¹ | R² | L | A |
|---|---|---|---|---|
| 35 | H | i-Pr | single bond | dibenzofuran-4-yl |
| 36 | Me | H | single bond | dibenzofuran-2-yl |
| 37 | H | H | single bond | dibenzofuran-2-yl |
| 38 | Me | Me | single bond | dibenzofuran-2-yl |
| 39 | Me | Et | single bond | dibenzofuran-2-yl |
| 40 | Me | i-Pr | single bond | dibenzofuran-2-yl |
| 41 | Et | i-Pr | single bond | dibenzofuran-2-yl |
| 42 | H | i-Pr | single bond | dibenzofuran-2-yl |
| 43 | Me | H | single bond | dibenzofuran-2-yl |

TABLE 1-continued
| Compound number | R¹ | R² | L | A |
|---|---|---|---|---|
| 44 | H | H | single bond | 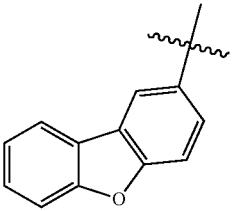 |
| 45 | Me | Me | single bond | 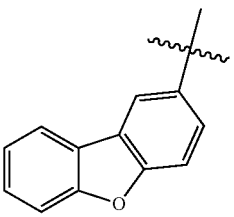 [SMILES: *c1ccc2oc3ccccc3c2c1] |
| 46 | Me | i-Pr | single bond | 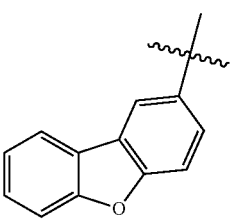 [SMILES: *c1ccc2oc3ccccc3c2c1] |
| 47 | Et | i-Pr | single bond | 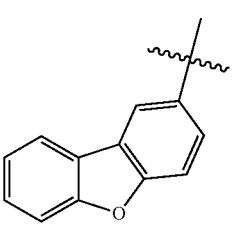 |
| 48 | H | i-Pr | single bond | 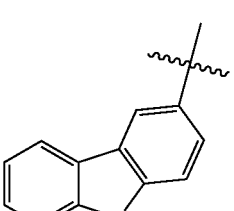 |
| 49 | Me | H | single bond | 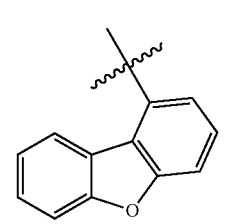 [SMILES: *c1cccc2oc3ccccc3c12] |
| 50 | H | H | single bond | 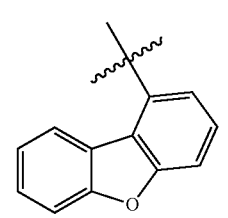 |

TABLE 1-continued

| Compound number | R¹ | R² | L | A |
|---|---|---|---|---|
| 51 | Me | Me | single bond | dibenzofuran-1-yl |
| 52 | Me | Et | single bond | dibenzofuran-1-yl |
| 53 | Me | i-Pr | single bond | dibenzofuran-1-yl |
| 54 | Et | i-Pr | single bond | dibenzofuran-1-yl |
| 55 | H | i-Pr | single bond | dibenzofuran-1-yl |
| 56 | Me | H | 1,4-phenylene | dibenzothiophen-4-yl |
| 57 | H | H | 1,4-phenylene | dibenzothiophen-4-yl |

TABLE 1-continued
| Compound number | R¹ | R² | L | A |
|---|---|---|---|---|
| 58 | Me | Me | 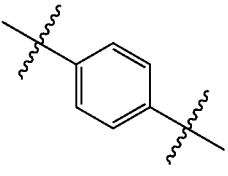 [SMILES: *c1ccc(*)cc1] | 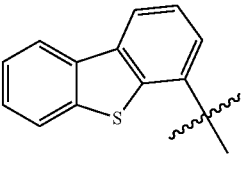 [SMILES: *c1cccc2c1sc1ccccc12] |
| 59 | Me | Et | 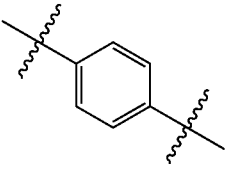 [SMILES: *c1ccc(*)cc1] | 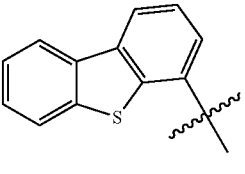 [SMILES: *c1cccc2c1sc1ccccc12] |
| 60 | Me | i-Pr | 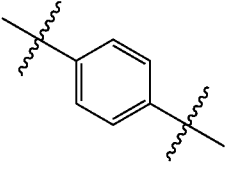 [SMILES: *c1ccc(*)cc1] | 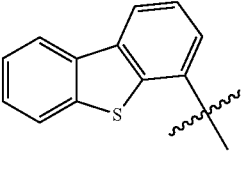 [SMILES: *c1cccc2c1sc1ccccc12] |
| 61 | Et | i-Pr | 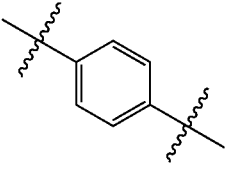 [SMILES: *c1ccc(*)cc1] | 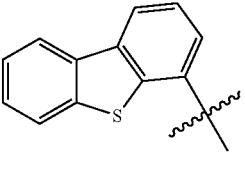 |
| 62 | H | i-Pr | 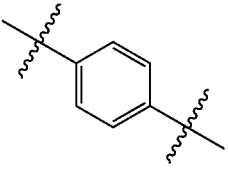 [SMILES: *c1ccc(*)cc1] | 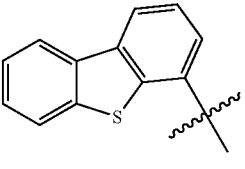 [SMILES: *c1cccc2c1sc1ccccc12] |
| 63 | Me | H | 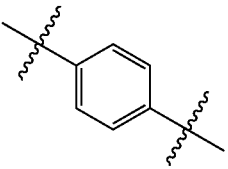 [SMILES: *c1ccc(*)cc1] | 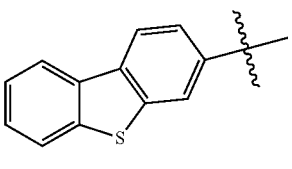 |
| 64 | H | H | 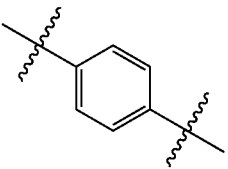 [SMILES: *c1ccc(*)cc1] | 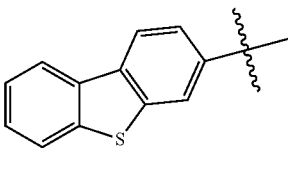 [SMILES: *c1ccc2c(c1)sc1ccccc12] |
| 65 | Me | Me | 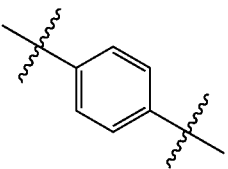 [SMILES: *c1ccc(*)cc1] | 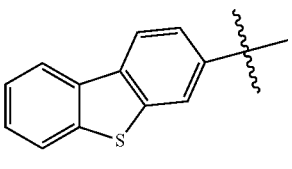 [SMILES: *c1ccc2c(c1)sc1ccccc12] |

TABLE 1-continued
| Compound number | R¹ | R² | L | A |
|---|---|---|---|---|
| 66 | Me | Et | 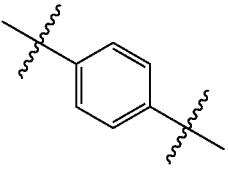 [SMILES: *c1ccc(*)cc1] | 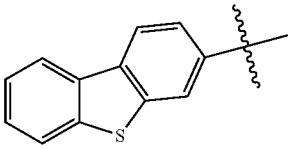 [SMILES: *c1ccc2c(c1)sc1ccccc12] |
| 67 | Me | i-Pr | 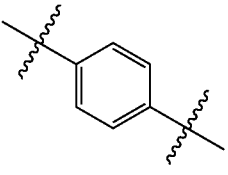 | 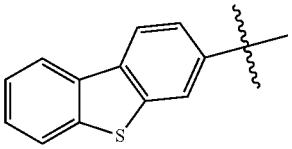 [SMILES: *c1ccc2c(c1)sc1ccccc12] |
| 68 | Et | i-Pr | 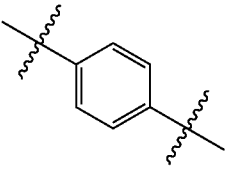 [SMILES: *c1ccc(*)cc1] | 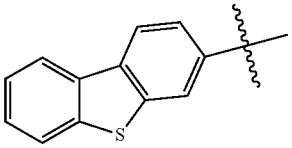 [SMILES: *c1ccc2c(c1)sc1ccccc12] |
| 69 | H | i-Pr | 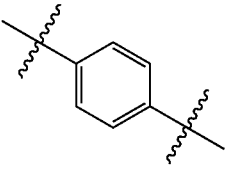 [SMILES: *c1ccc(*)cc1] | 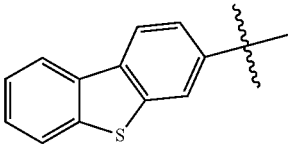 [SMILES: *c1ccc2c(c1)sc1ccccc12] |
| 70 | Me | H | 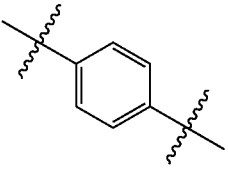 [SMILES: *c1ccc(*)cc1] | 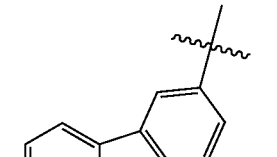 |
| 71 | H | H | 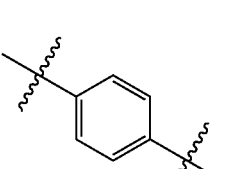 |  |
| 72 | Me | Me | 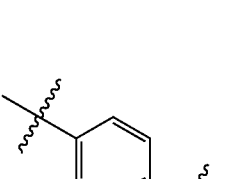 | 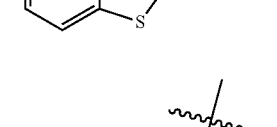 |

TABLE 1-continued
| Compound number | R¹ | R² | L | A |
|---|---|---|---|---|
| 73 | Me | Et | 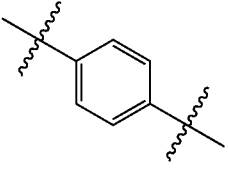 [SMILES: *c1ccc(*)cc1] | 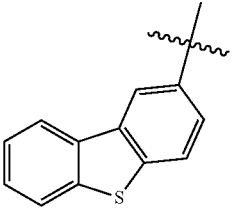 |
| 74 | Me | i-Pr | 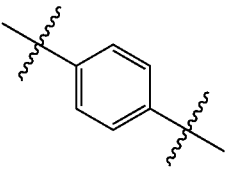 [SMILES: *c1ccc(*)cc1] | 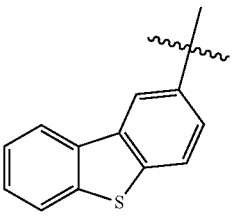 |
| 75 | Et | i-Pr | 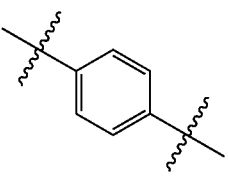 [SMILES: *c1ccc(*)cc1] | 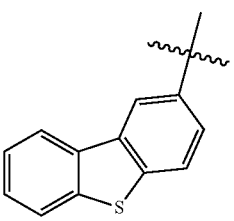 |
| 76 | H | i-Pr | 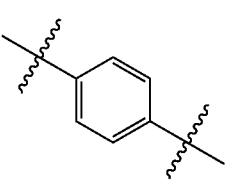 [SMILES: *c1ccc(*)cc1] | 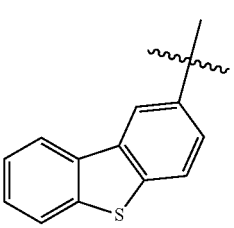 |
| 77 | Me | H | 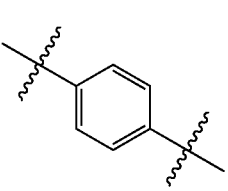 [SMILES: *c1ccc(*)cc1] | 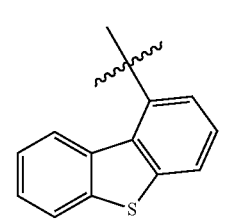 [SMILES: *c1cccc2sc3ccccc3c12] |
| 78 | H | H | 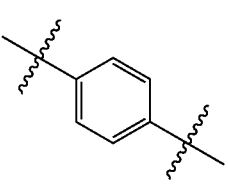 | 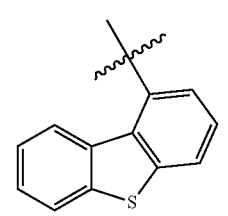 [SMILES: *c1cccc2sc3ccccc3c12] |
| 79 | Me | Me | 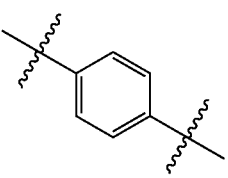 [SMILES: *c1ccc(*)cc1] | 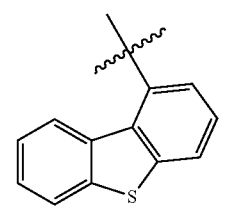 |

TABLE 1-continued
| Compound number | R¹ | R² | L | A |
|---|---|---|---|---|
| 80 | Me | Et | 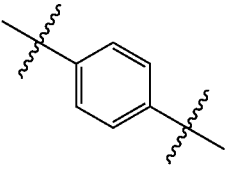 [SMILES: *c1ccc(*)cc1] | 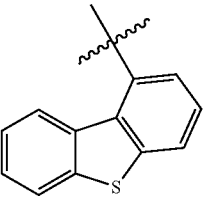 |
| 81 | Me | i-Pr | 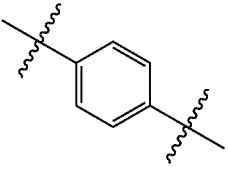 [SMILES: *c1ccc(*)cc1] | 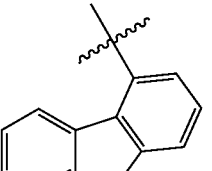 |
| 82 | Et | i-Pr | 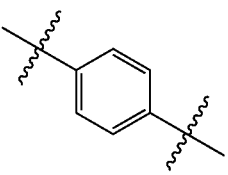 [SMILES: *c1ccc(*)cc1] | 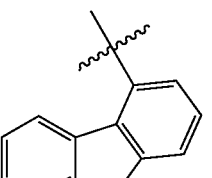 |
| 83 | H | i-Pr | 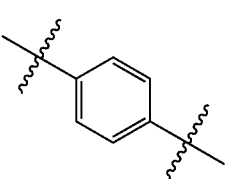 [SMILES: *c1ccc(*)cc1] | 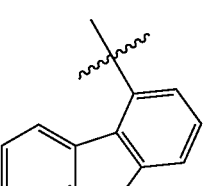 |
| 84 | Me | H | 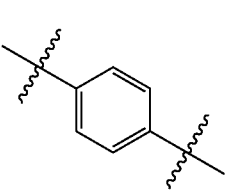 [SMILES: *c1ccc(*)cc1] | 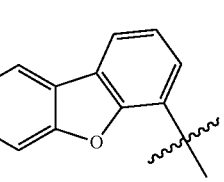 |
| 85 | H | H | 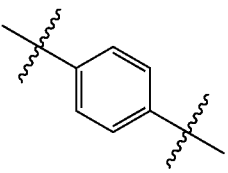 [SMILES: *c1ccc(*)cc1] | 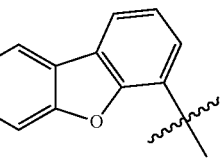 |
| 86 | Me | Me | 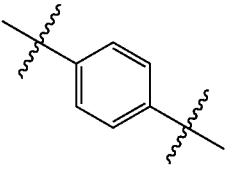 [SMILES: *c1ccc(*)cc1] | 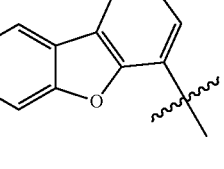 |
| 87 | Me | Et | 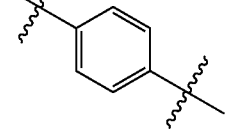 | 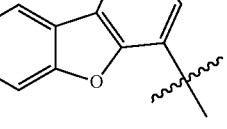 |

TABLE 1-continued
| Compound number | R¹ | R² | L | A |
|---|---|---|---|---|
| 88 | Me | i-Pr | 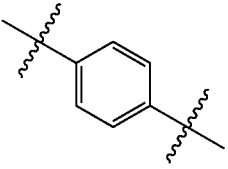 [SMILES: *c1ccc(*)cc1] | 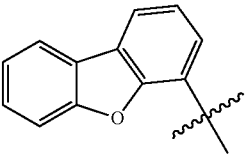 |
| 89 | Et | i-Pr | 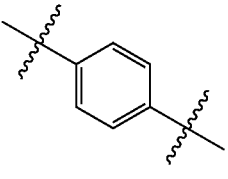 [SMILES: *c1ccc(*)cc1] | 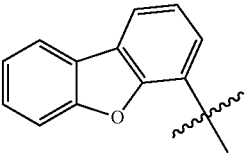 [SMILES: *c1cccc2c1oc1ccccc12] |
| 90 | H | i-Pr | 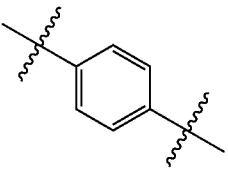 [SMILES: *c1ccc(*)cc1] | 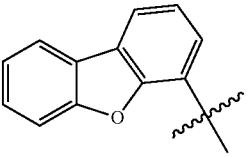 [SMILES: *c1cccc2c1oc1ccccc12] |
| 91 | Me | H | 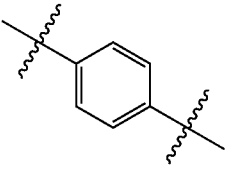 [SMILES: *c1ccc(*)cc1] | 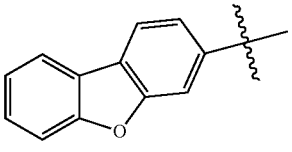 [SMILES: *c1ccc2c(c1)oc1ccccc12] |
| 92 | H | H | 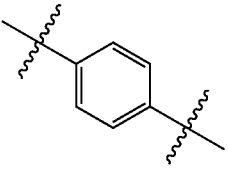 | 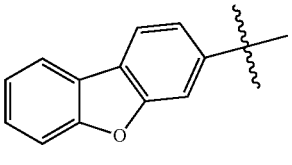 [SMILES: *c1ccc2c(c1)oc1ccccc12] |
| 93 | Me | Me | 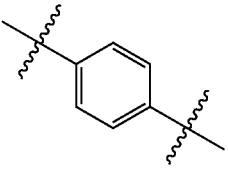 [SMILES: *c1ccc(*)cc1] | 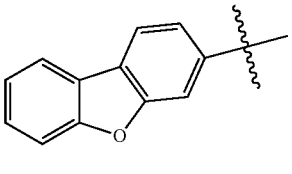 |
| 94 | Me | Et | 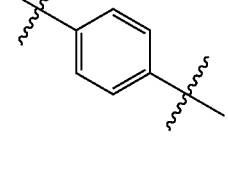 | 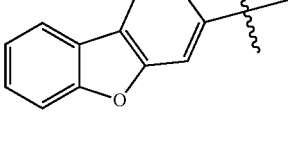 |
| 95 | Me | i-Pr | 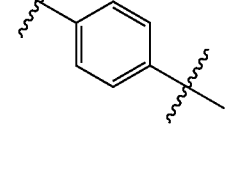 | 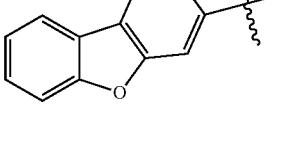 |

TABLE 1-continued
| Compound number | R¹ | R² | L | A |
|---|---|---|---|---|
| 96 | Et | i-Pr | 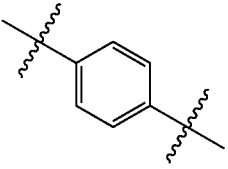 [SMILES: *c1ccc(*)cc1] | 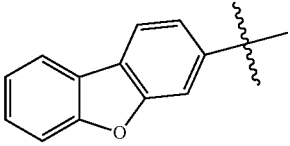 [SMILES: *c1ccc2c(c1)oc1ccccc12] |
| 97 | H | i-Pr | 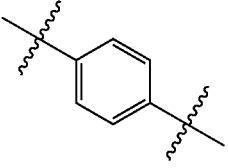 [SMILES: *c1ccc(*)cc1] | 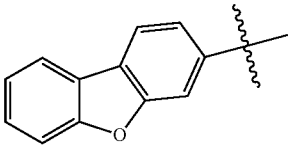 |
| 98 | Me | H | 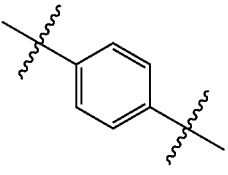 [SMILES: *c1ccc(*)cc1] | 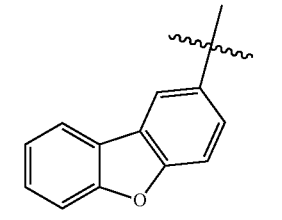 [SMILES: *c1ccc2oc3ccccc3c2c1] |
| 99 | H | H | 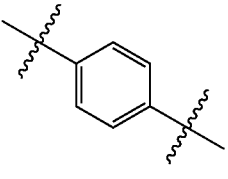 [SMILES: *c1ccc(*)cc1] | 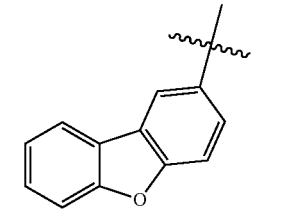 [SMILES: *c1ccc2oc3ccccc3c2c1] |
| 100 | Me | Me | 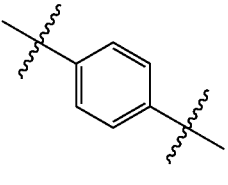 [SMILES: *c1ccc(*)cc1] | 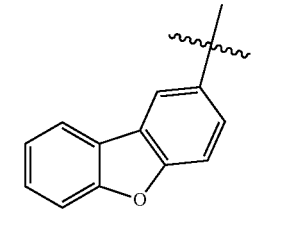 [SMILES: *c1ccc2oc3ccccc3c2c1] |
| 101 | Me | i-Pr | 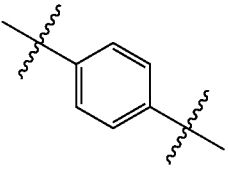 [SMILES: *c1ccc(*)cc1] | 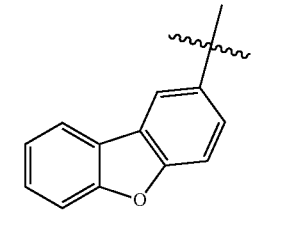 [SMILES: *c1ccc2oc3ccccc3c2c1] |
| 102 | Et | i-Pr | 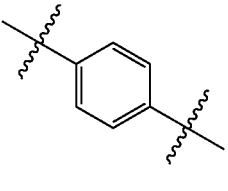 [SMILES: *c1ccc(*)cc1] | 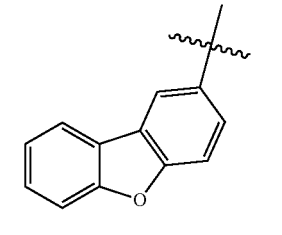 [SMILES: *c1ccc2oc3ccccc3c2c1] |

TABLE 1-continued
| Compound number | R¹ | R² | L | A |
|---|---|---|---|---|
| 103 | H | i-Pr | 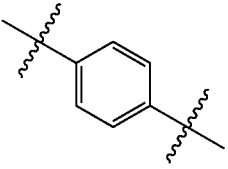 [SMILES: *c1ccc(*)cc1] | 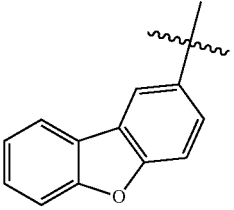 [SMILES: *c1ccc2oc3ccccc3c2c1] |
| 104 | Me | H | 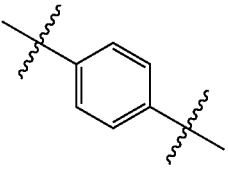 | 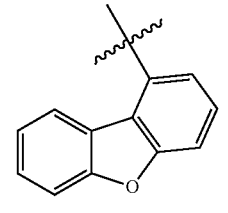 [SMILES: *c1cccc2oc3ccccc3c12] |
| 105 | H | H | 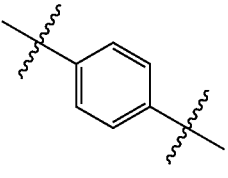 [SMILES: *c1ccc(*)cc1] | 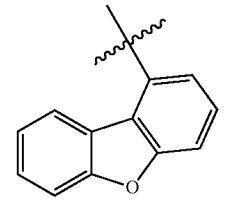 |
| 106 | Me | Me | 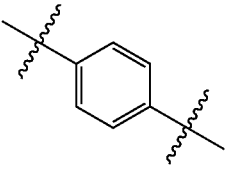 [SMILES: *c1ccc(*)cc1] | 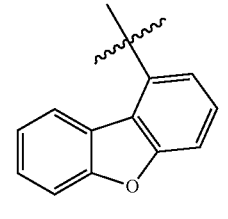 [SMILES: *c1cccc2oc3ccccc3c12] |
| 107 | Me | Et | 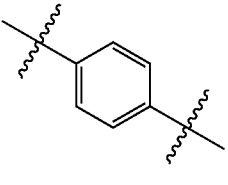 [SMILES: *c1ccc(*)cc1] | 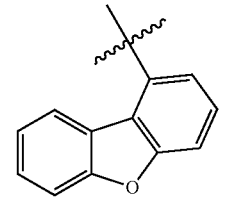 |
| 108 | Me | i-Pr | 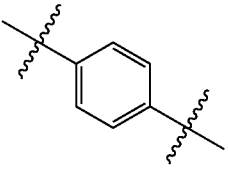 [SMILES: *c1ccc(*)cc1] | 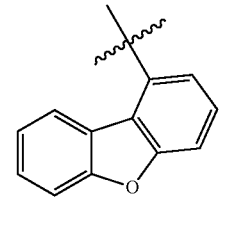 [SMILES: *c1cccc2oc3ccccc3c12] |
| 109 | Et | i-Pr | 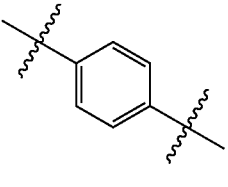 [SMILES: *c1ccc(*)cc1] | 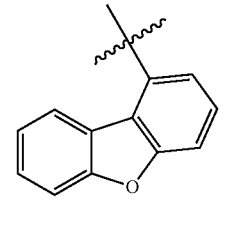 [SMILES: *c1cccc2oc3ccccc3c12] |

TABLE 1-continued
| Compound number | R¹ | R² | L | A |
|---|---|---|---|---|
| 110 | H | i-Pr | 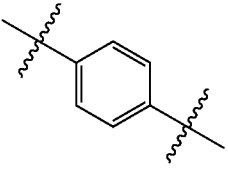 [SMILES: *c1ccc(*)cc1] | 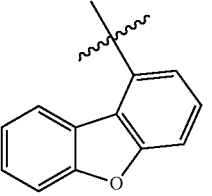 |
| 111 | Me | Me | single bond | 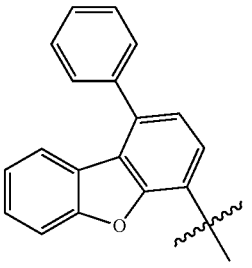 [SMILES: *c1ccc(-c2ccccc2)c2c1oc1ccccc12] |
| 112 | Me | Me | single bond | 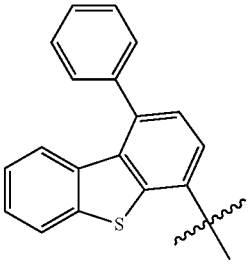 [SMILES: *c1ccc(-c2ccccc2)c2c1sc1ccccc12] |
| 113 | Me | Me | 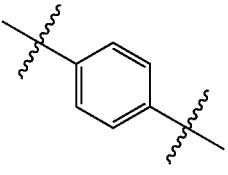 [SMILES: *c1ccc(*)cc1] | 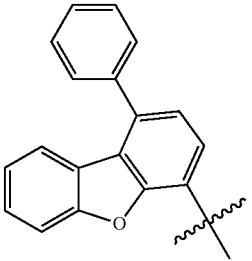 [SMILES: *c1ccc(-c2ccccc2)c2c1oc1ccccc12] |
| 114 | Me | Me | 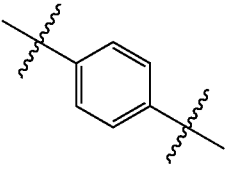 [SMILES: *c1ccc(*)cc1] | 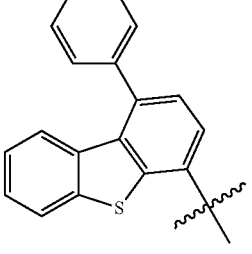 |
| 115 | Me | Me | single bond | 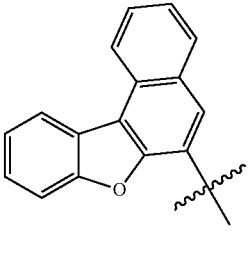 [SMILES: *c1cc2ccccc2c2c1oc1ccccc12] |

TABLE 1-continued

| Compound number | R¹ | R² | L | A |
|---|---|---|---|---|
| 116 | Me | Me | single bond | |
| 117 | Me | Me | | |
| 118 | Me | Me | | |
| 119 | Me | Me | single bond | |
| 120 | Me | Me | single bond | |
| 121 | Me | Me | | |
| 122 | Me | Me | | |

TABLE 1-continued
| Compound number | R¹ | R² | L | A |
|---|---|---|---|---|
| 123 | Me | Me | single bond | 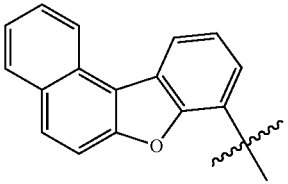 [SMILES: *c1cccc2c1oc1ccc3ccccc3c12] |
| 124 | Me | Me | single bond | 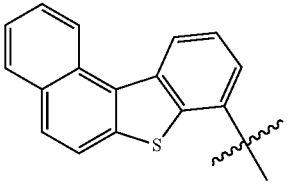 [SMILES: *c1cccc2c1sc1ccc3ccccc3c12] |
| 125 | Me | Me | 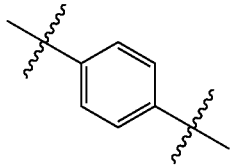 [SMILES: *c1ccc(*)cc1] | 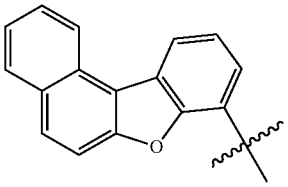 [SMILES: *c1cccc2c1oc1ccc3ccccc3c12] |
| 126 | Me | Me | 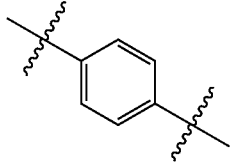 [SMILES: *c1ccc(*)cc1] | 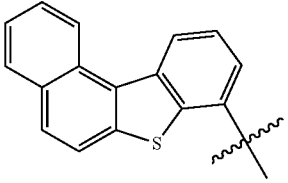 [SMILES: *c1cccc2c1sc1ccc3ccccc3c12] |
| 127 | Me | Me | single bond | 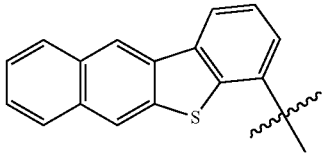 |
| 128 | Me | Me | single bond | 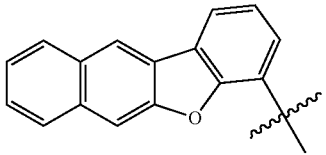 [SMILES: *c1cccc2c1oc1cc3ccccc3cc12] |
| 129 | Me | Me | 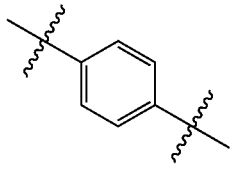 [SMILES: *c1ccc(*)cc1] | 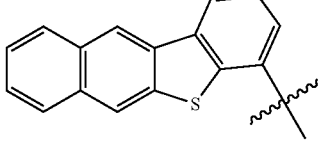 |
| 130 | Me | Me | 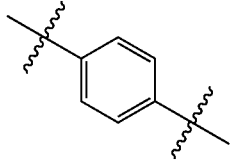 [SMILES: *c1ccc(*)cc1] | 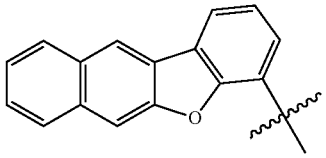 |

TABLE 1-continued
| Compound number | R¹ | R² | L | A |
|---|---|---|---|---|
| 131 | Me | Me | single bond | 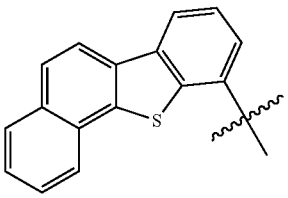 [SMILES: *c1cccc2c1sc1c3ccccc3ccc21] |
| 132 | Me | Me | single bond | 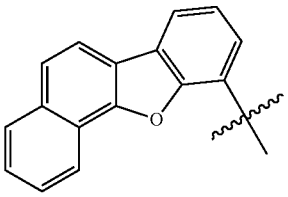 [SMILES: *c1cccc2c1oc1c3ccccc3ccc21] |
| 133 | Me | Me | 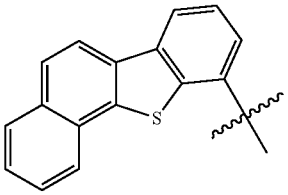 [SMILES: *c1cccc2c1sc1c3ccccc3ccc21] | 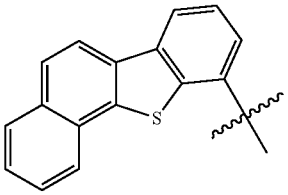 [SMILES: *c1cccc2c1sc1c3ccccc3ccc21] |
| 134 | Me | Me | 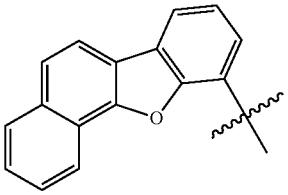 [SMILES: *c1cccc2c1oc1c3ccccc3ccc21] | 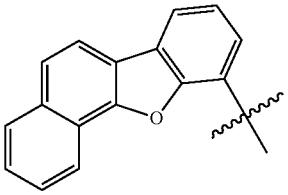 [SMILES: *c1cccc2c1oc1c3ccccc3ccc21] |
| 135 | Me | Me | single bond | 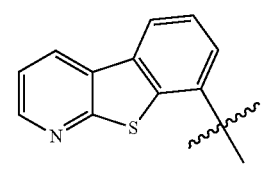 [SMILES: *c1cccc2c1sc1ncccc12] |
| 136 | Me | Me | single bond | 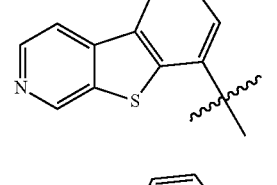 |
| 137 | Me | Me | single bond | 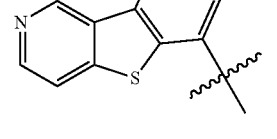 |
| 138 | Me | Me | single bond | 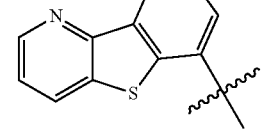 |

TABLE 1-continued
| Compound number | R¹ | R² | L | A |
|---|---|---|---|---|
| 139 | Me | Me | single bond | 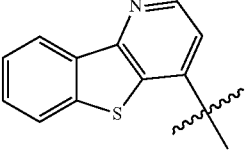 |
| 140 | Me | Me | single bond | 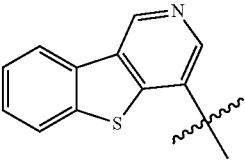 |
| 141 | Me | Me | single bond | 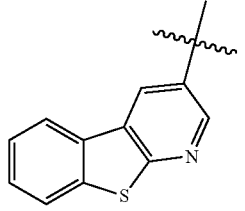 [SMILES: *c1cnc2sc3ccccc3c2c1] |
| 142 | Me | Me | single bond | 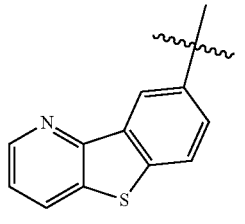 |
| 143 | Me | Me | single bond | 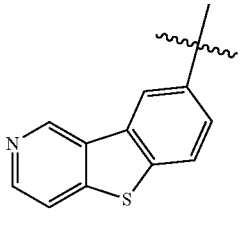 [SMILES: *c1ccc2sc3ccncc3c2c1] |
| 144 | Me | Me | single bond | 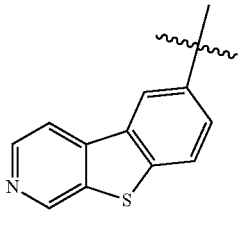 |
| 145 | Me | Me | single bond | 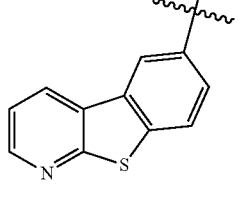 |

TABLE 1-continued
| Compound number | R¹ | R² | L | A |
|---|---|---|---|---|
| 146 | Me | Me | 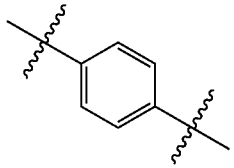 [SMILES: *c1ccc(*)cc1] | 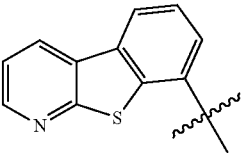 [SMILES: *c1cccc2c1sc1ncccc12] |
| 147 | Me | Me | 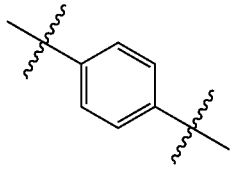 [SMILES: *c1ccc(*)cc1] | 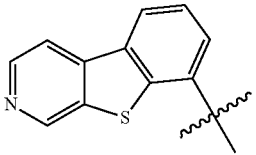 [SMILES: *c1cccc2c1sc1cnccc12] |
| 148 | Me | Me | 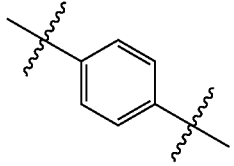 [SMILES: *c1ccc(*)cc1] | 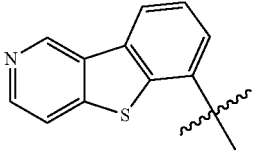 |
| 149 | Me | Me | 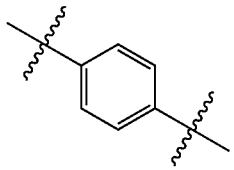 [SMILES: *c1ccc(*)cc1] | 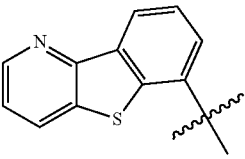 [SMILES: *c1cccc2c1sc1cccnc12] |
| 150 | Me | Me | 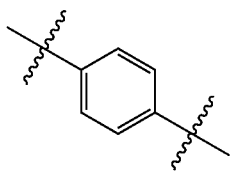 [SMILES: *c1ccc(*)cc1] | 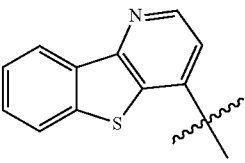 |
| 151 | Me | Me | 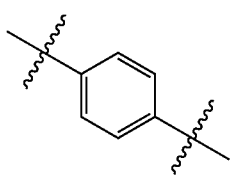 [SMILES: *c1ccc(*)cc1] | 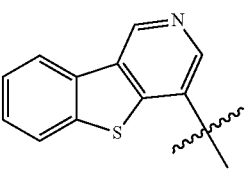 [SMILES: *c1cncc2c1sc1ccccc12] |
| 152 | Me | Me | 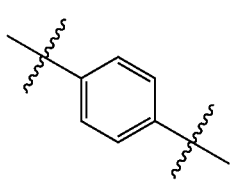 [SMILES: *c1ccc(*)cc1] |  |
| 153 | Me | Me | 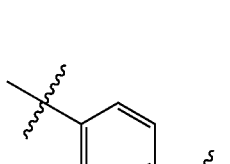 | 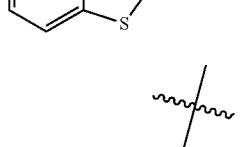 |

TABLE 1-continued

| Compound number | R¹ | R² | L | A |
|---|---|---|---|---|
| 154 | Me | Me | *para*-phenylene | pyrido-benzothiophene (N top-left, S bottom) |
| 155 | Me | Me | *para*-phenylene | pyrido-benzothiophene isomer |
| 156 | Me | Me | *para*-phenylene | pyrido-benzothiophene isomer |
| 157 | Me | Me | single bond | pyrido-benzofuran |
| 158 | Me | Me | single bond | pyrido-benzofuran isomer |
| 159 | Me | Me | single bond | pyrido-benzofuran isomer |
| 160 | Me | Me | single bond | pyrido-benzofuran isomer |
| 161 | Me | Me | single bond | pyrido-benzofuran isomer |

TABLE 1-continued
| Compound number | R¹ | R² | L | A |
|---|---|---|---|---|
| 162 | Me | Me | single bond | 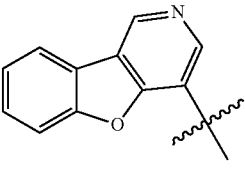 |
| 163 | Me | Me | single bond | 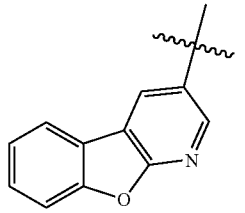 [SMILES: *c1cnc2oc3ccccc3c2c1] |
| 164 | Me | Me | single bond | 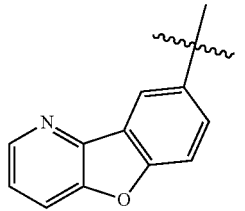 [SMILES: *c1ccc2oc3cccnc3c2c1] |
| 165 | Me | Me | single bond | 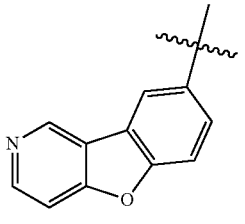 [SMILES: *c1ccc2oc3ccncc3c2c1] |
| 166 | Me | Me | single bond | 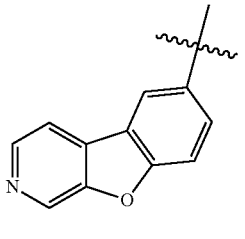 |
| 167 | Me | Me | single bond | 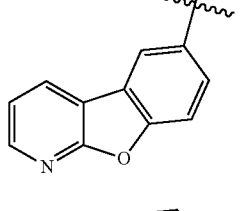 |
| 168 | Me | Me | 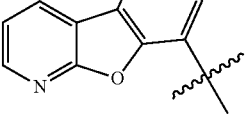 | 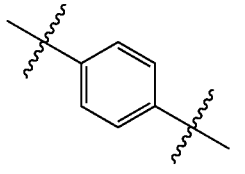 [SMILES: *c1ccc(*)cc1] |

TABLE 1-continued
| Compound number | R¹ | R² | L | A |
|---|---|---|---|---|
| 169 | Me | Me | 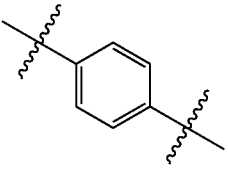 [SMILES: *c1ccc(*)cc1] | 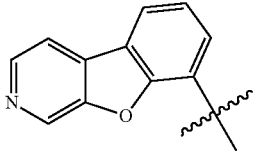 [SMILES: *c1cccc2c1oc1cnccc12] |
| 170 | Me | Me | 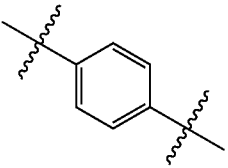 [SMILES: *c1ccc(*)cc1] | 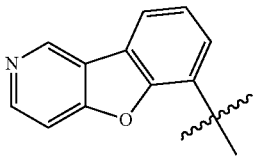 [SMILES: *c1cccc2c1oc1ccncc12] |
| 171 | Me | Me | 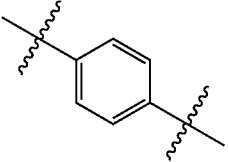 [SMILES: *c1ccc(*)cc1] | 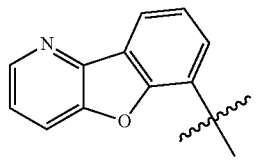 [SMILES: *c1cccc2c1oc1cccnc12] |
| 172 | Me | Me | 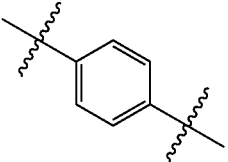 [SMILES: *c1ccc(*)cc1] | 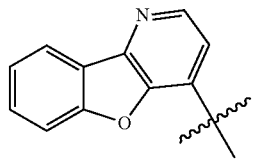 [SMILES: *c1ccnc2c1oc1ccccc12] |
| 173 | Me | Me | 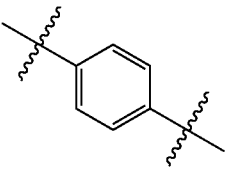 [SMILES: *c1ccc(*)cc1] | 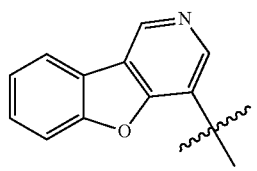 [SMILES: *c1cncc2c1oc1ccccc12] |
| 174 | Me | Me | 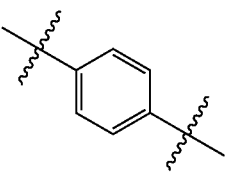 [SMILES: *c1ccc(*)cc1] | 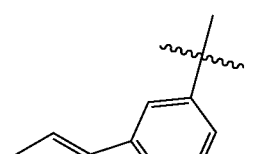 |
| 175 | Me | Me | 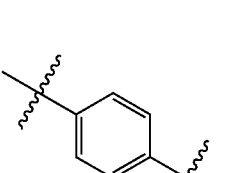 | 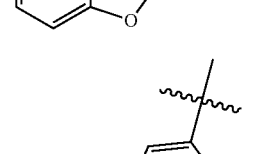 |
| 176 | Me | Me | 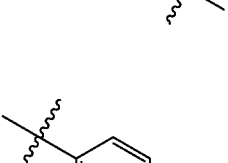 | 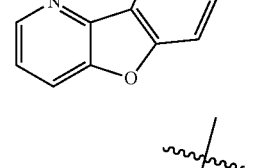 |

TABLE 1-continued
| Compound number | R¹ | R² | L | A |
|---|---|---|---|---|
| 177 | Me | Me | 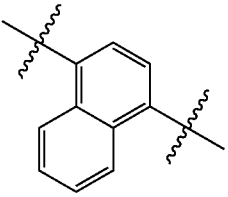 [SMILES: *c1ccc(*)c2ccccc12] | 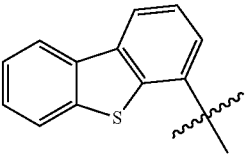 [SMILES: *c1cccc2c1sc1ccccc12] |
| 178 | Me | Me | 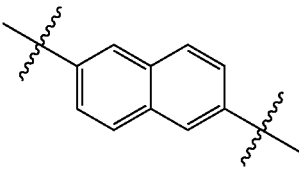 [SMILES: *c1ccc2cc(*)ccc2c1] | 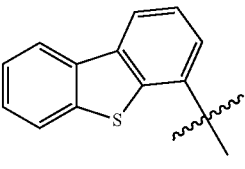 [SMILES: *c1cccc2c1sc1ccccc12] |
| 179 | Me | Me | 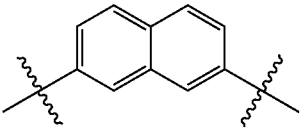 [SMILES: *c1ccc2ccc(*)cc2c1] | 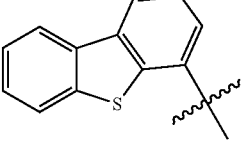 |
| 180 | Me | Me | 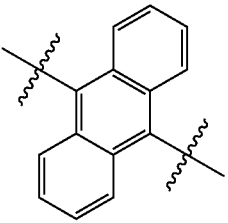 [SMILES: *c1c2ccccc2c(*)c2ccccc12] | 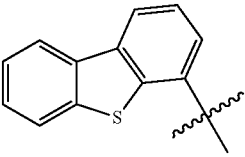 |
| 181 | Me | Me | 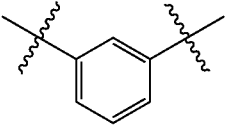 [SMILES: *c1cccc(*)c1] | 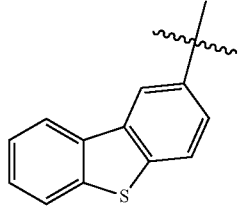 [SMILES: *c1ccc2sc3ccccc3c2c1] |
| 182 | Me | Me | 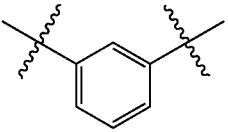 [SMILES: *c1cccc(*)c1] | 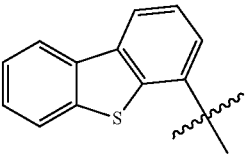 |
| 183 | Me | Me | 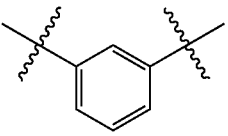 [SMILES: *c1cccc(*)c1] | 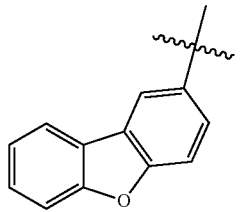 [SMILES: *c1ccc2oc3ccccc3c2c1] |

TABLE 1-continued
| Compound number | R¹ | R² | L | A |
|---|---|---|---|---|
| 184 | Me | Me | 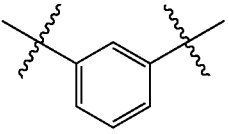 [SMILES: *c1cccc(*)c1] | 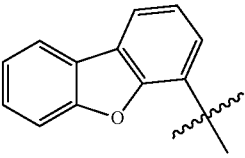 |
| 185 | Me | Me | 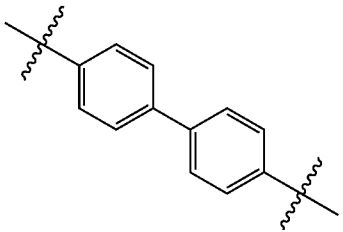 [SMILES: *c1ccc(-c2ccc(*)cc2)cc1] | 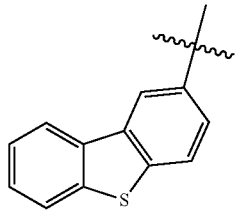 [SMILES: *c1ccc2sc3ccccc3c2c1] |
| 186 | Me | Me | 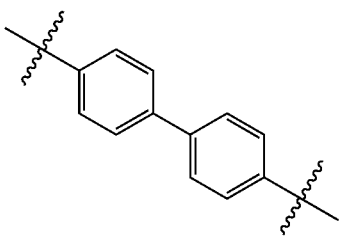 [SMILES: *c1ccc(-c2ccc(*)cc2)cc1] | 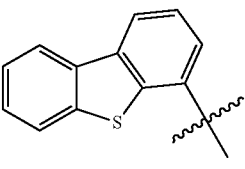 |
| 187 | Me | Me | 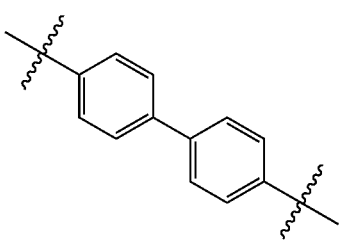 [SMILES: *c1ccc(-c2ccc(*)cc2)cc1] | 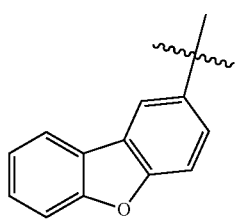 [SMILES: *c1ccc2oc3ccccc3c2c1] |
| 188 | Me | Me | 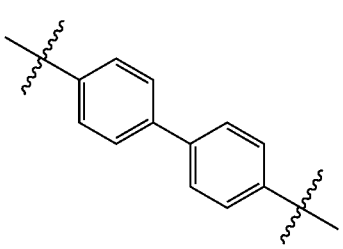 [SMILES: *c1ccc(-c2ccc(*)cc2)cc1] | 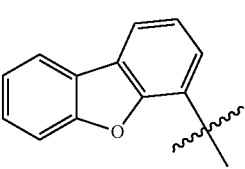 [SMILES: *c1cccc2c1oc1ccccc12] |
| 189 | Me | Me | 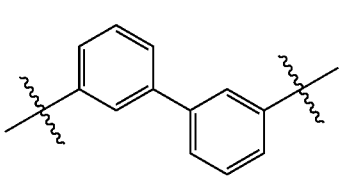 [SMILES: *c1cccc(-c2cccc(*)c2)c1] | 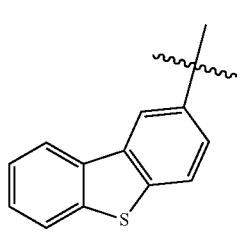 |
| 190 | Me | Me | 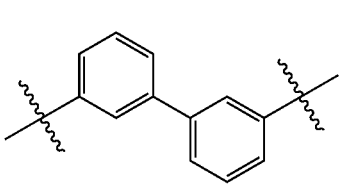 [SMILES: *c1cccc(-c2cccc(*)c2)c1] | 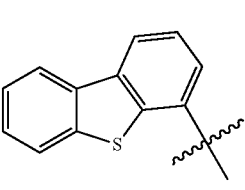 |

TABLE 1-continued

| Compound number | R¹ | R² | L | A |
|---|---|---|---|---|
| 191 | Me | Me | 3,3'-biphenylene | dibenzofuran-2-yl |
| 192 | Me | Me | 3,3'-biphenylene | dibenzofuran-4-yl |
| 193 | Me | Me | 1,4-phenylene | 1-phenyldibenzothiophen-4-yl |
| 194 | Me | Me | 1,4-phenylene | 2-phenyldibenzothiophen-6-yl |
| 195 | Me | Me | 1,4-phenylene | 3-phenyldibenzothiophen-6-yl |
| 196 | Me | Me | 1,4-phenylene | 6-phenyldibenzothiophen-4-yl |
| 197 | Me | Me | 1,4-phenylene | 1-phenyldibenzofuran-4-yl |

TABLE 1-continued
| Compound number | R¹ | R² | L | A |
|---|---|---|---|---|
| 198 | Me | Me | 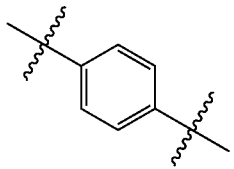 [SMILES: *c1ccc(*)cc1] | 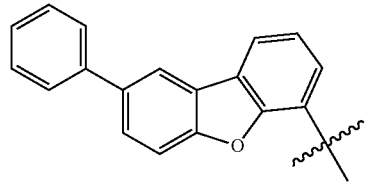 [SMILES: *c1cccc2c1oc1ccc(-c3ccccc3)cc12] |
| 199 | Me | Me | 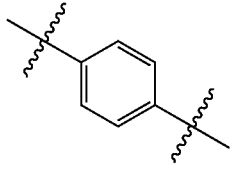 [SMILES: *c1ccc(*)cc1] | 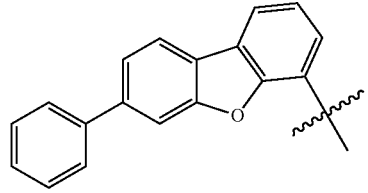 [SMILES: *c1cccc2c1oc1cc(-c3ccccc3)ccc12] |
| 200 | Me | Me | 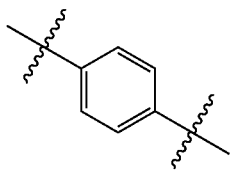 [SMILES: *c1ccc(*)cc1] | 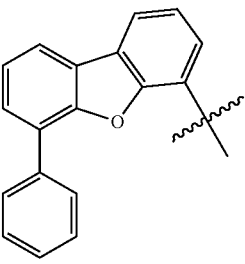 [SMILES: *c1cccc2c1oc1c(-c3ccccc3)cccc12] |
| 201 | Me | Me | single bond | 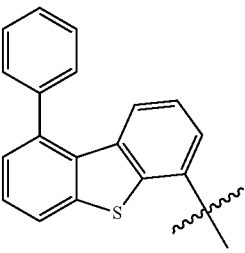 [SMILES: *c1cccc2c1sc1cccc(-c3ccccc3)c12] |
| 202 | Me | Me | single bond |  |
| 203 | Me | Me | single bond | 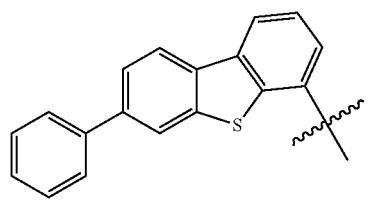 [SMILES: *c1cccc2c1sc1cc(-c3ccccc3)ccc12] |

TABLE 1-continued

| Compound number | R¹ | R² | L | A |
|---|---|---|---|---|
| 204 | Me | Me | single bond | 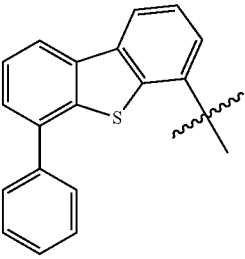 [SMILES: *c1cccc2c1sc1c(-c3ccccc3)cccc12] |
| 205 | Me | Me | single bond | 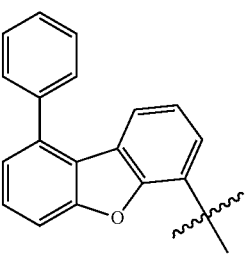 [SMILES: *c1cccc2c1oc1cccc(-c3ccccc3)c12] |
| 206 | Me | Me | single bond | 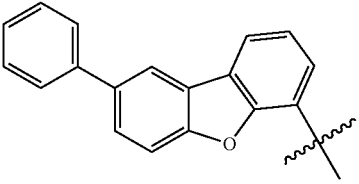 [SMILES: *c1cccc2c1oc1ccc(-c3ccccc3)cc12] |
| 207 | Me | Me | single bond | 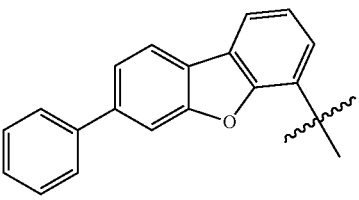 [SMILES: *c1cccc2c1oc1cc(-c3ccccc3)ccc12] |
| 208 | Me | Me | single bond | 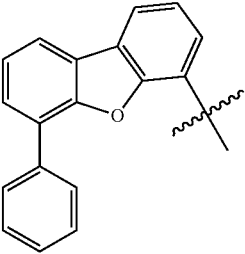 [SMILES: *c1cccc2c1oc1c(-c3ccccc3)cccc12] |

In yet another aspect of the present disclosure, a formulation that includes a compound according to Formula I is described. The formulation can include one or more components selected from the group consisting of a solvent, a host, a hole injection material, hole transport material, an electron transport layer material (see below).

According to another aspect of the present disclosure, a first device is also provided. The first device includes a first organic light emitting device, that includes an anode, a cathode, and an organic layer disposed between the anode and the cathode. The organic layer can be an emissive layer that includes a host and a phosphorescent dopant. The emissive layer can include a compound according to Formula I, and its variations as described herein. In a preferred embodiment, the compound is a host material in the emissive layer. In another embodiment, the compound can be used in an electron transporting layer. The compound is also suitable for use in a hole blocking layer.

In a preferred embodiment, the organic layer comprises a compound having a structure according to Formula I Formula I

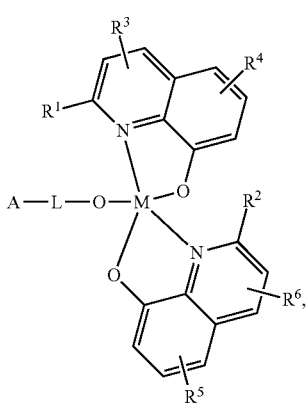

wherein M is a group III element;
wherein L is a single bond or comprises an aryl or heteroaryl group having from 5-20 carbon atoms, which is optionally further substituted with one or more groups selected from hydrogen, deuterium, alkyl, cycloalkyl, aralkyl, alkoxy, aryloxy, amino, silyl, aryl, heteroaryl, and combinations thereof;
wherein A contains a group selected from the group consisting of dibenzothiophene, dibenzoselenophene, dibenzofuran, aza-dibenzofuran, aza-dibenzothiophene, aza-dibenzoselenophene, and combination thereof, which are optionally further substituted with one or more groups selected from hydrogen, deuterium, alkyl, cycloalkyl, aralkyl, alkoxy, aryloxy, amino, silyl, aryl, heteroaryl, and combinations thereof;
wherein $R^3$, $R^6$ each represent mono, di substitutions, or no substitution;
wherein $R^4$, $R^5$ each represent mono, di, tri substitutions, or no substitution; and
wherein $R^1$, $R^2$, $R^3$, $R^4$, $R^5$ and $R^6$ are each independently selected from the group consisting of hydrogen, deuterium, alkyl, cycloalkyl, aralkyl, alkoxy, aryloxy, amino, silyl, aryl, heteroaryl, and combinations thereof.

In one embodiment, $R^1$ and $R^2$ are each independently selected from the group consisting of hydrogen, deuterium, methyl, ethyl, propyl, iso-propyl, and combinations thereof.

According to another aspect of the first device, M is selected from the group consisting of Al, In, Ga. According to another aspect, M is Al. According to another aspect of the first device, L is selected from the group consisting of:
a single bond,

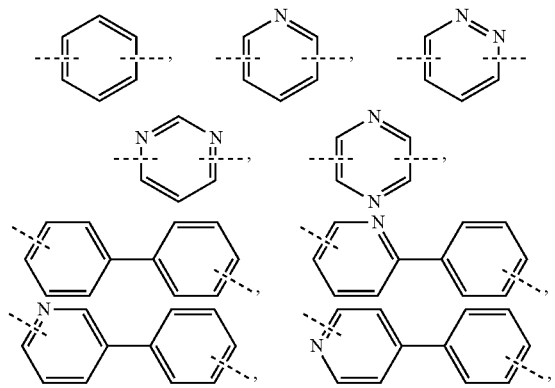

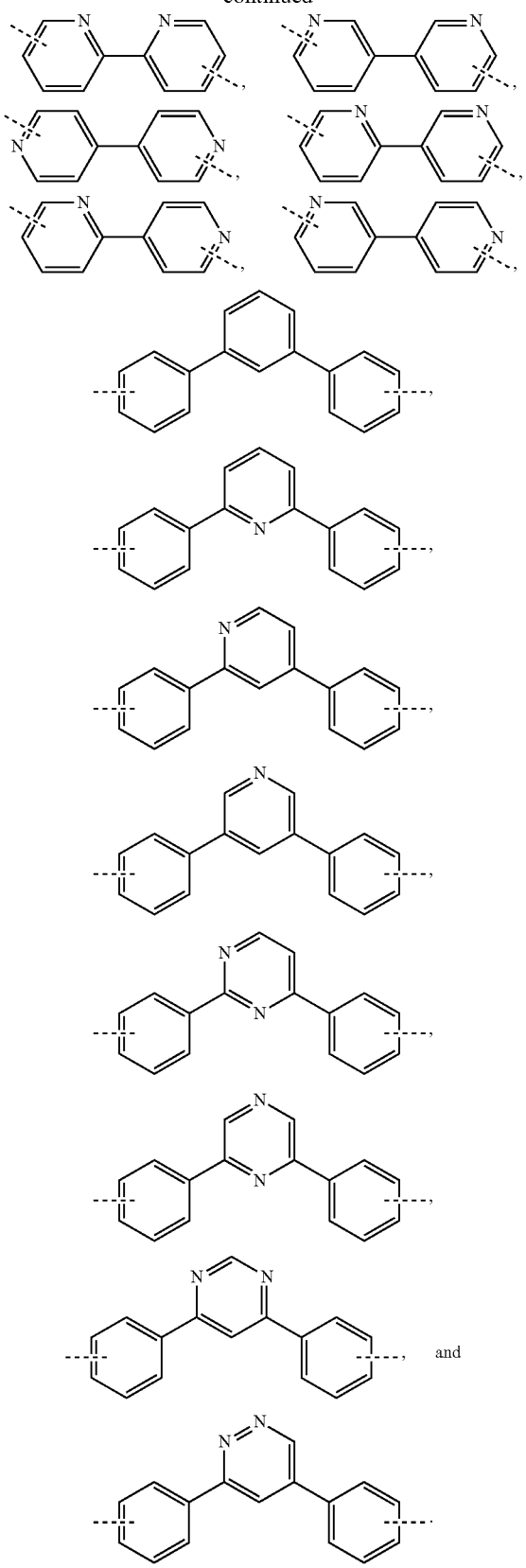

In another aspect of the first device, A is selected from the group consisting of:

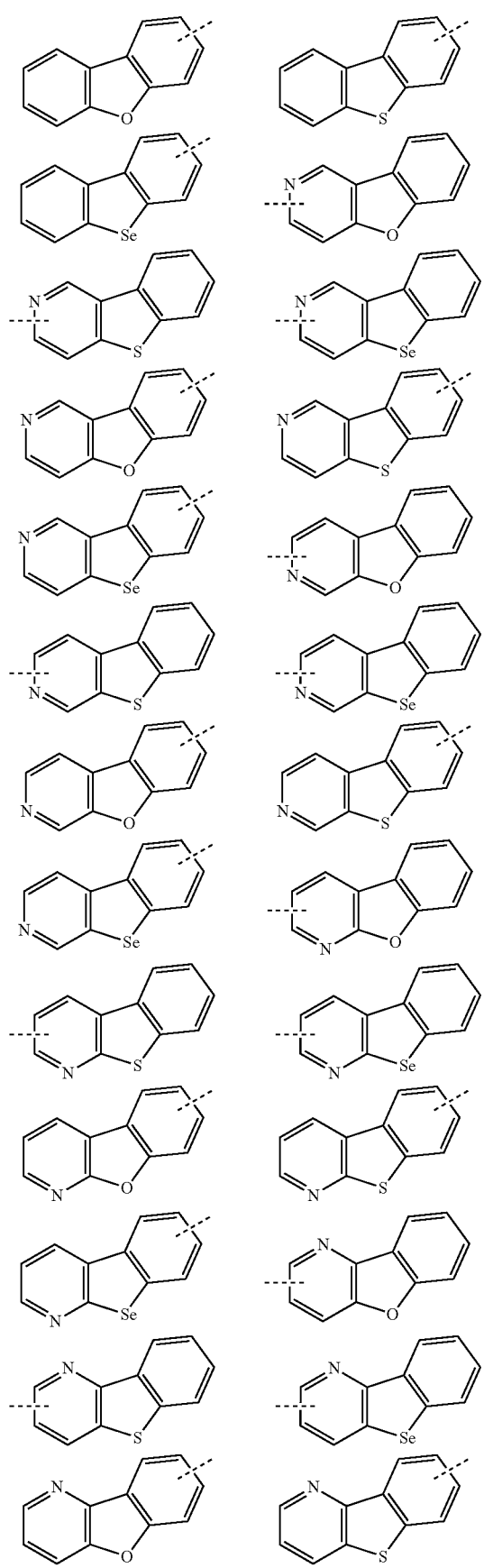
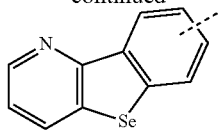
In another embodiment of the first device, the compound is selected from the group consisting of:
Compound 3
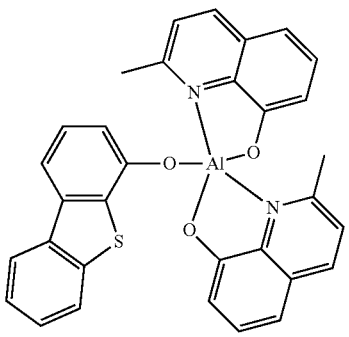
Compound 17
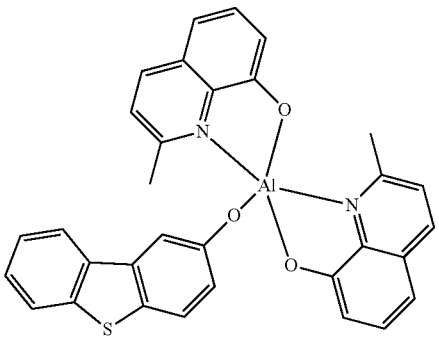
Compound 31
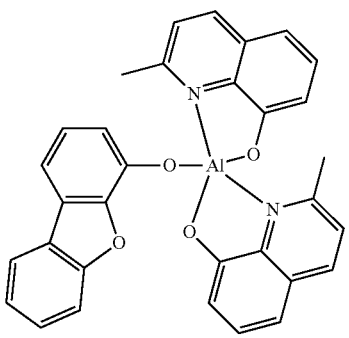
Compound 45
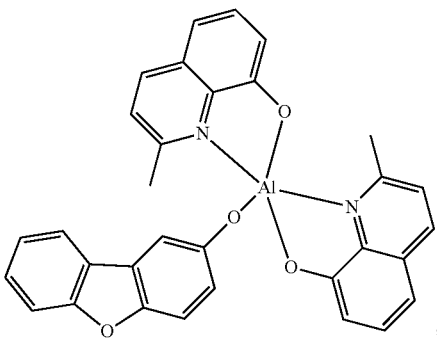

-continued
Compound 58
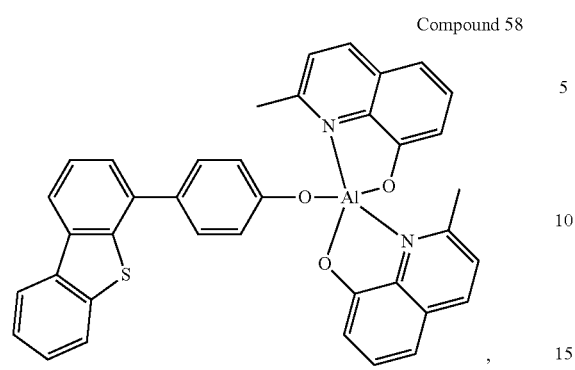
Compound 115
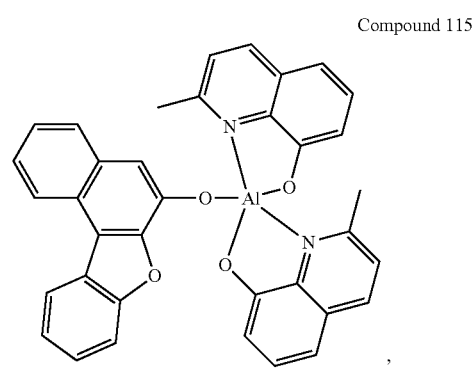
Compound 72
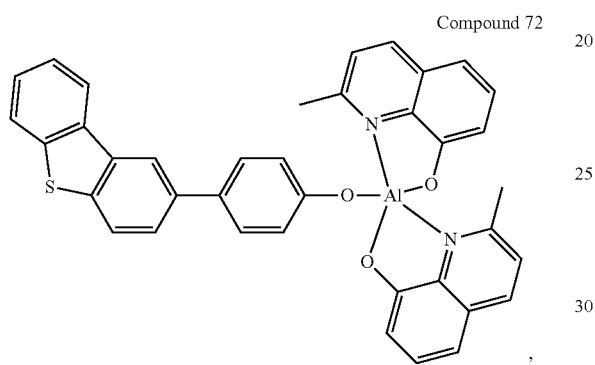
Compound 116
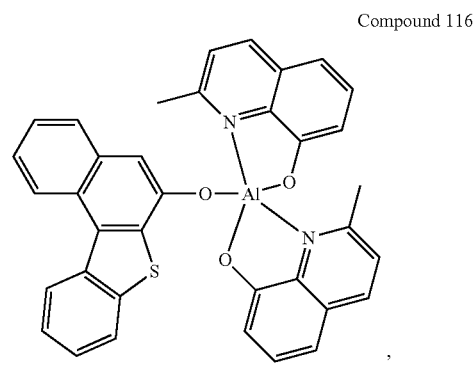
Compound 86
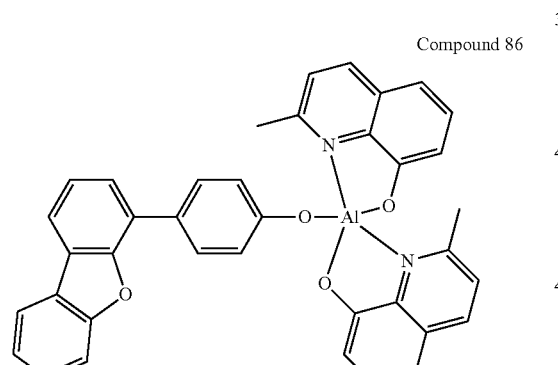
Compound 119
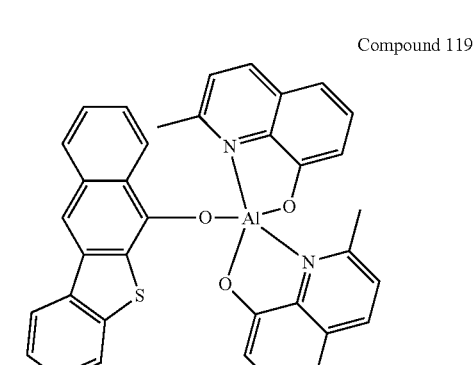
Compound 100
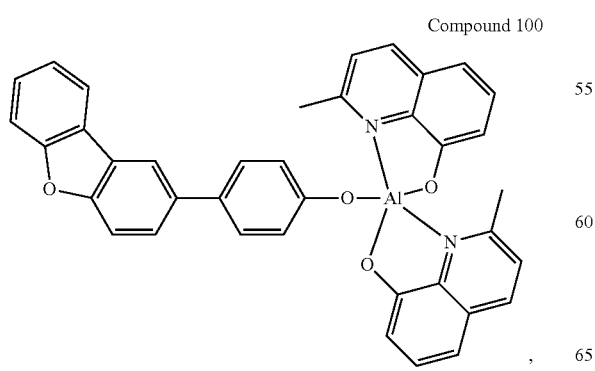
Compound 120
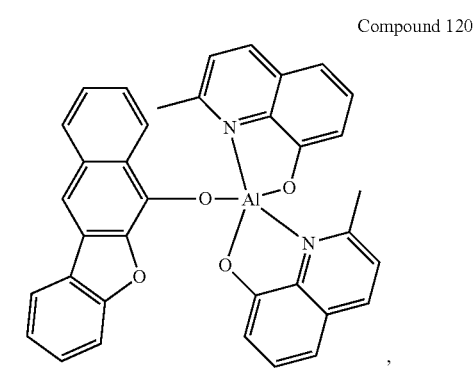

-continued

Compound 121
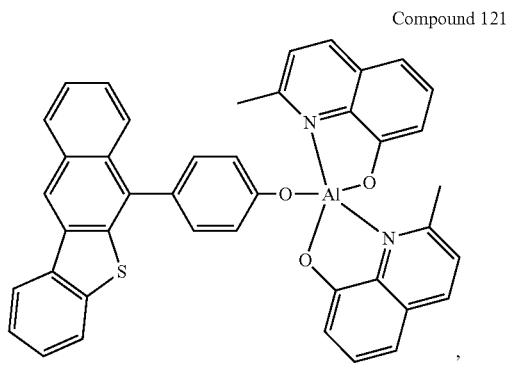

Compound 122
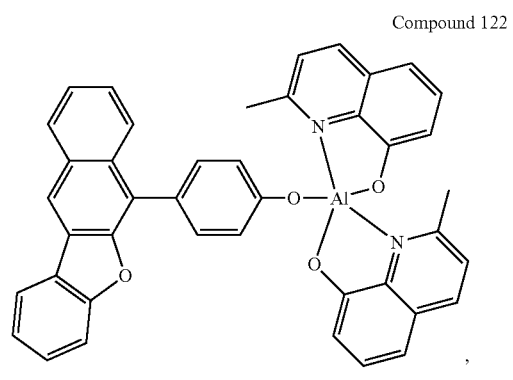

Compound 123
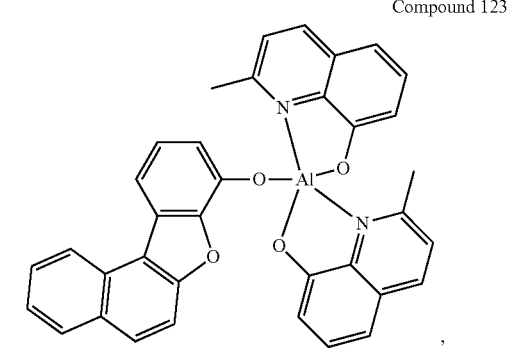

Compound 124
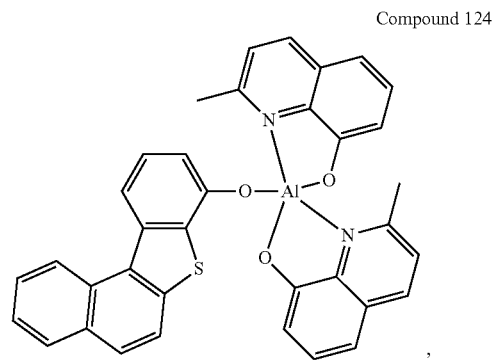

-continued

Compound 127
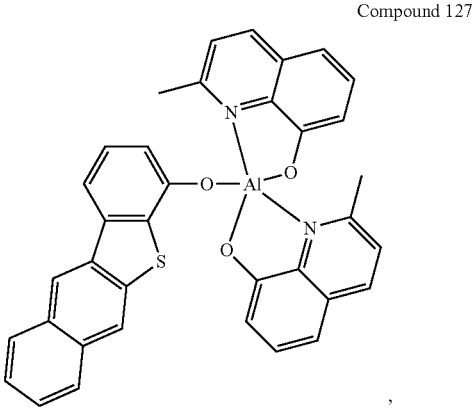

Compound 128
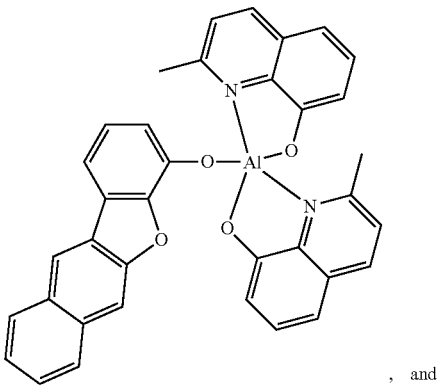

, and

Compound 131
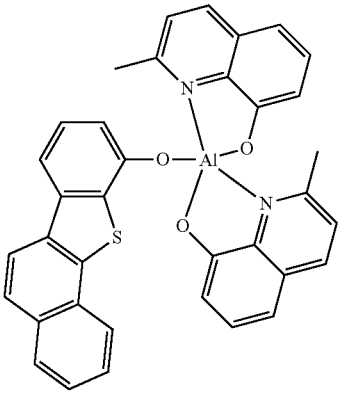

.

In another embodiment of the first device, the compound is selected from the group consisting of Compound 1 through Compound 208 listed in TABLE 1.

In another embodiment of the first device, M in the compound is aluminum; and $R^3$, $R^4$, $R^5$ and $R^6$ are hydrogen. The organic layer is an emissive layer and the compound having Formula I is a host.

In another embodiment of the first device, the organic layer further comprises an emissive dopant. The emissive dopant can be a transition metal complex having at least one ligand selected from the group consisting of:

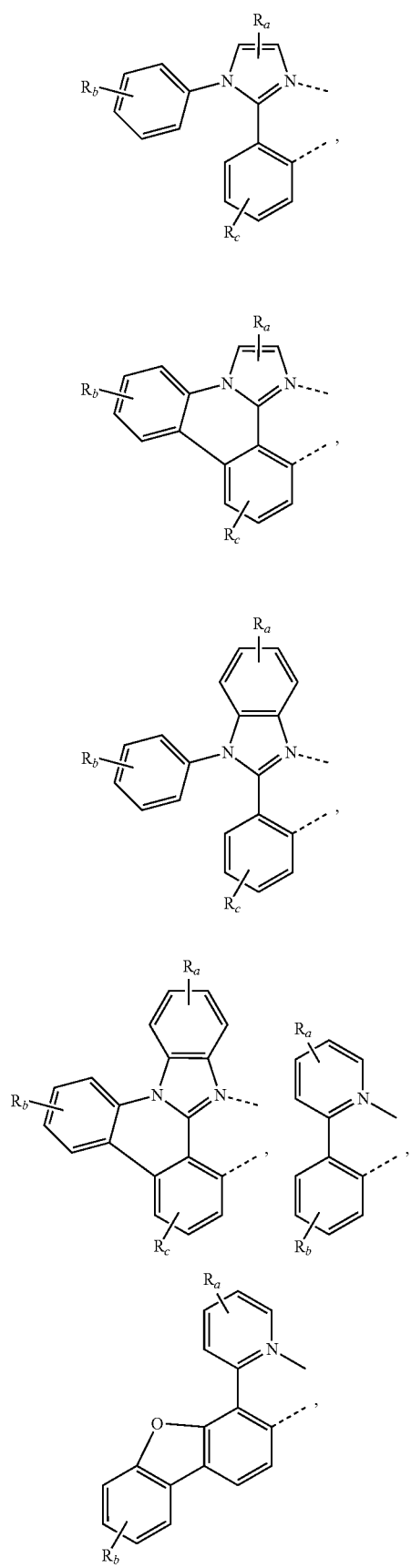
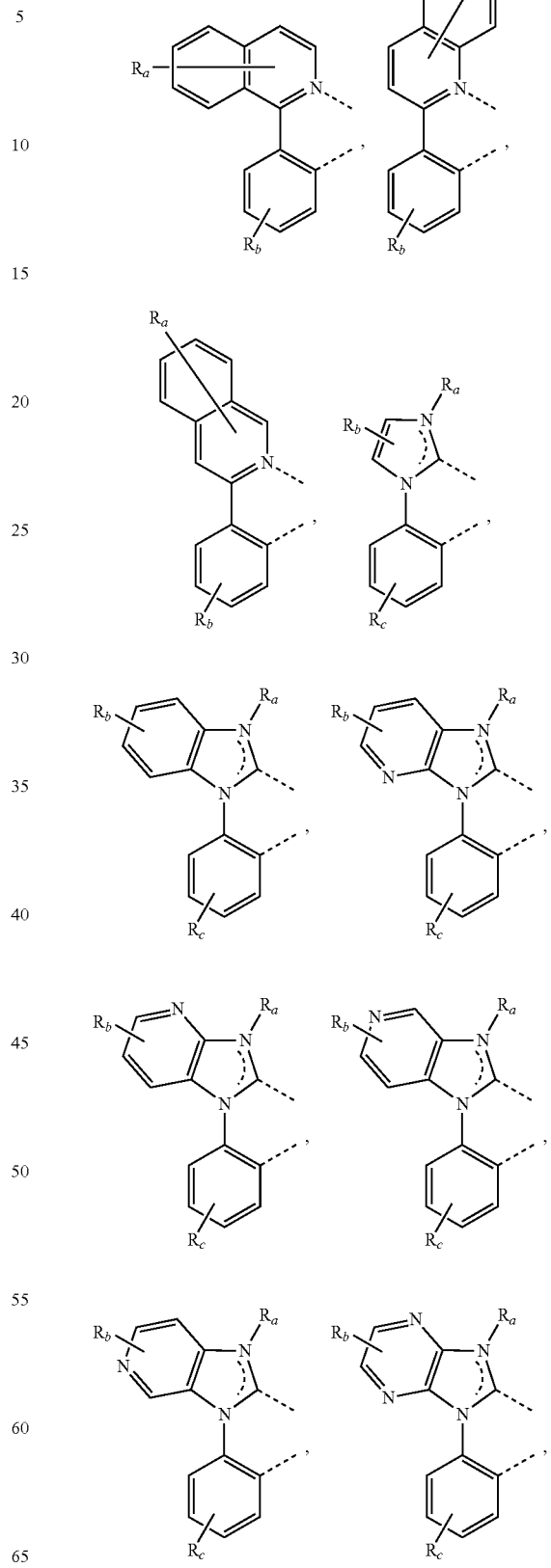

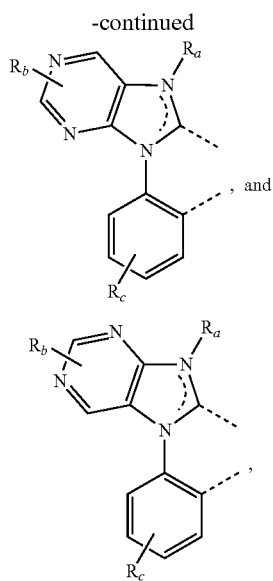

wherein $R_a$, $R_b$, and $R_c$ may represent mono, di, tri or tetra substitutions; $R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and two adjacent substituents of $R_a$, $R_b$, and $R_c$ are optionally joined to form a fused ring.

In one embodiment, the organic layer in the first device can be a blocking layer and the compound having the Formula I is a blocking material in the organic layer. In another embodiment, the organic layer in the first device can be an electron transporting layer and the compound having the Formula I is an electron transporting material in the organic layer.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but not limit to: a phthalocyanine or porphryin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and sliane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

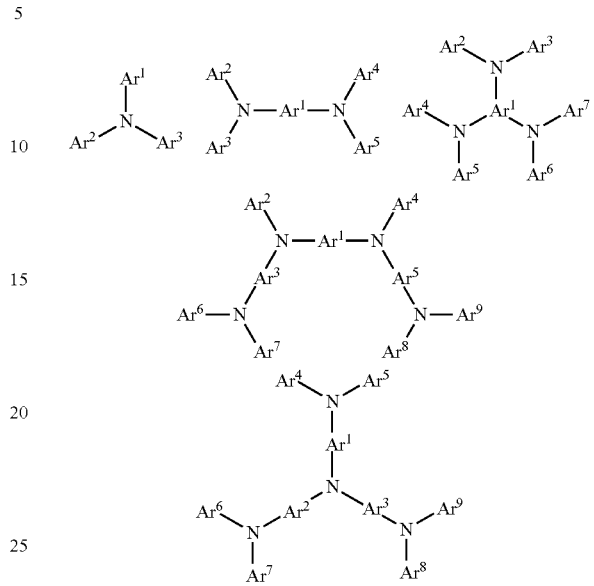

Each of $Ar^1$ to $Ar^9$ is selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

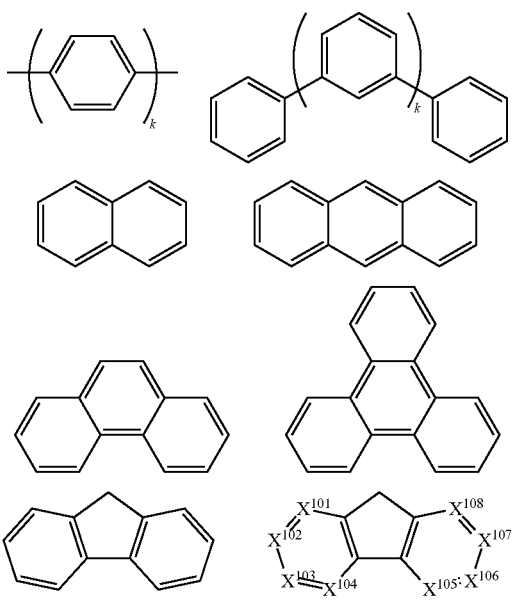

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not limit to the following general formula:

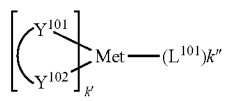

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

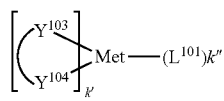

wherein Met is a metal; ($Y^{103}$-$Y^{104}$) is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

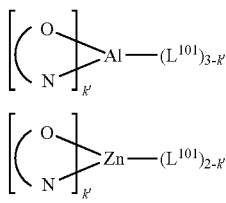

wherein (O—N) is a bidentate ligand, having metal coordinated to atoms O and N.

In another aspect, Met is selected from Ir and Pt.

In a further aspect, ($Y^{103}$-$Y^{104}$) is a carbene ligand.

Examples of organic compounds used as host are selected from the group consisting aromatic hydrocarbon cyclic compounds such as benzene, biphenyl, triphenyl, triphenylene, naphthalene, anthracene, phenalene, phenanthrene, fluorene, pyrene, chrysene, perylene, azulene; group consisting aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and group consisting 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

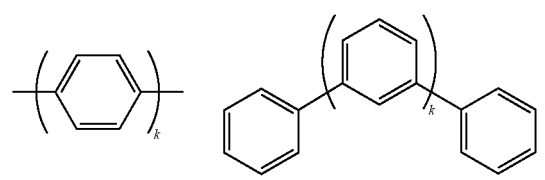
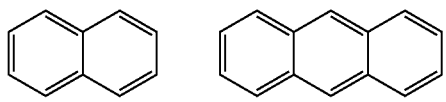
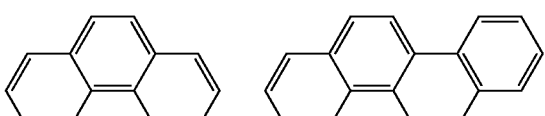
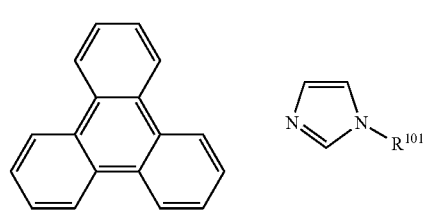
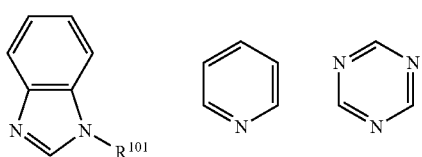
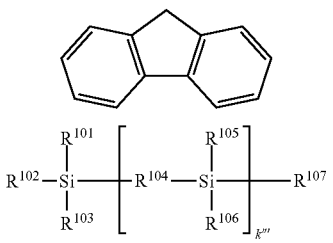
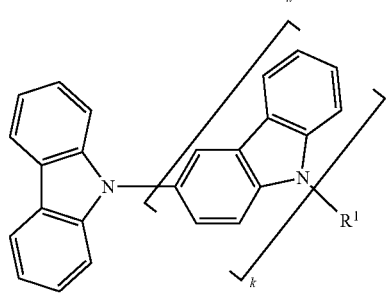
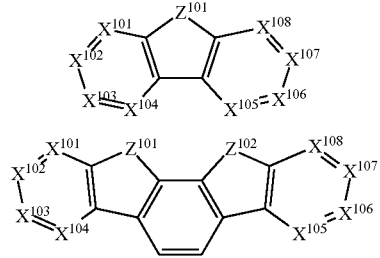

-continued

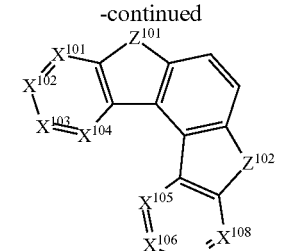
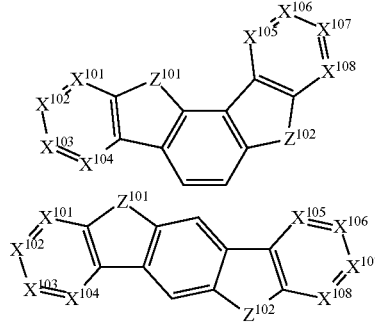
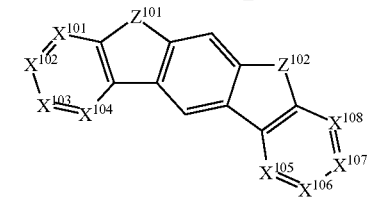

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

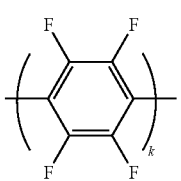
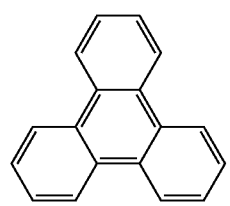

-continued

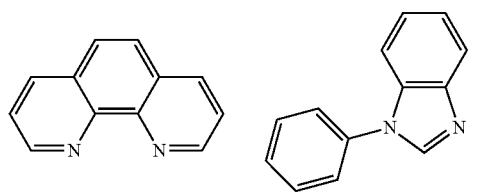

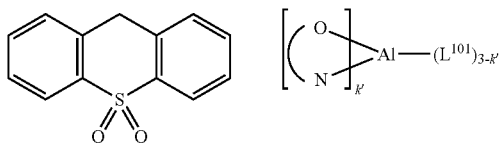

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

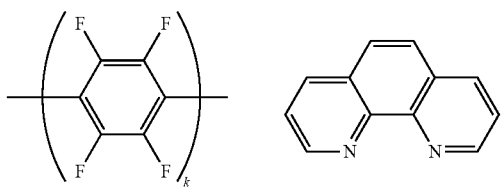

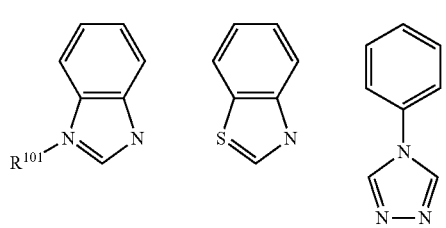

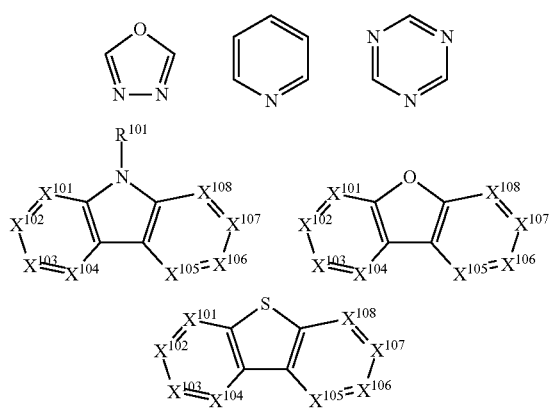

-continued

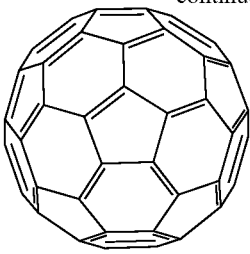

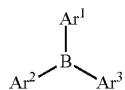

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^a$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

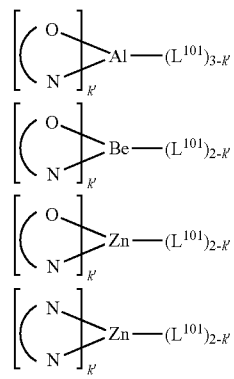

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 2 below. Table 1 lists non-limiting classes of materials, non-limiting examples of compounds for each class, and references that disclose the materials.

TABLE 2

| MATERIAL | EXAMPLES OF MATERIAL | PUBLICATIONS |
| --- | --- | --- |
| | Hole injection materials | |
| Phthalocyanine and porphryin compounds | | Appl. Phys. Lett. 69, 2160 (1996) |
| Starburst triarylamines | | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polypthiophene) | | Synth. Met. 87, 171 (1997) WO2007002683 |
| Phosphonic acid and sliane SAMs | | US20030162053 |
| Triarylamine or polythiophene polymers with conductivity dopants | | EP1725079A1 |

TABLE 2-continued

| MATERIAL | EXAMPLES OF MATERIAL | PUBLICATIONS |
| --- | --- | --- |
| Organic compounds with conductive inorganic compounds, such as molybdenum and tungsten oxides | | US20050123751<br>SID Symposium Digest, 37, 923 (2006)<br>WO2009018009 |
| n-type semiconducting organic complexes | | US20020158242 |
| Metal organometallic complexes | | US20060240279 |
| Cross-linkable compounds | | US20080220265 |
| Polythiophene based polymers and copolymers | | WO 2011075644<br>EP2350216 |

TABLE 2-continued
| MATERIAL | EXAMPLES OF MATERIAL | PUBLICATIONS |
|---|---|---|
| | Hole transporting materials | |
| Triarylamines (e.g., TPD, α-NPD) | 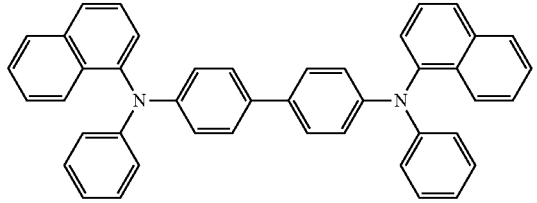 [SMILES: c1ccc(N(c2ccc(-c3ccc(N(c4ccccc4)c4cccc5ccccc45)cc3)cc2)c2cccc3ccccc23)cc1] | Appl. Phys. Lett. 51, 913 (1987)<br><br>US5061569<br><br>EP650955<br><br>J. Mater. Chem. 3, 319 (1993) |

TABLE 2-continued

| MATERIAL | EXAMPLES OF MATERIAL | PUBLICATIONS |
|---|---|---|
| | | Appl. Phys. Lett. 90, 183503 (2007) |
| | | Appl. Phys. Lett. 90, 183503 (2007) |
| Triaylamine on spirofluorene core | | Synth. Met. 91, 209 (1997) |
| Arylamine carbazole compounds | | Adv. Mater. 6, 677 (1994), US20080124572 |

TABLE 2-continued
| MATERIAL | EXAMPLES OF MATERIAL | PUBLICATIONS |
| --- | --- | --- |
| Triarylamine with (di)benzothiophene/ (di)benzofuran | 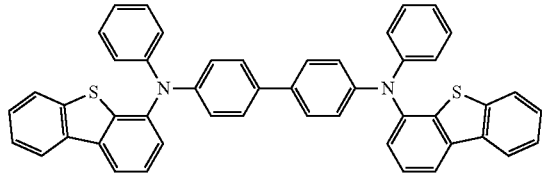 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |
| Indolocarbazoles | 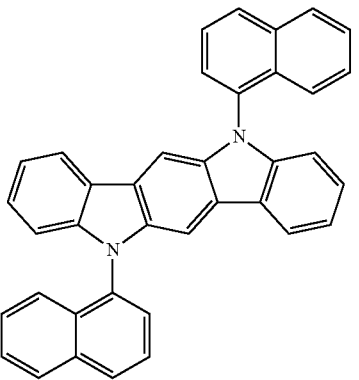 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 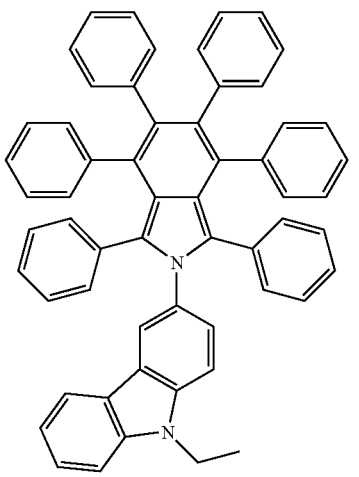 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 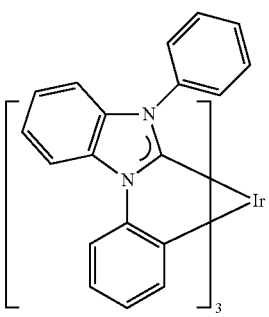 | US20080018221 |

TABLE 2-continued
| MATERIAL | EXAMPLES OF MATERIAL | PUBLICATIONS |
|---|---|---|
| | Phosphorescent OLED host materials<br>Red hosts | |
| Arylcarbazoles | 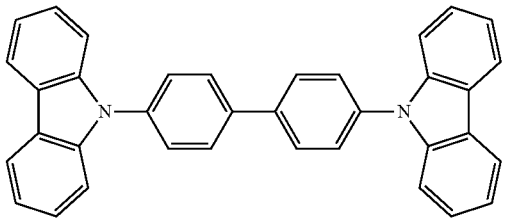 [SMILES: c1ccc2c(c1)c1ccccc1n2-c1ccc(-c2ccc(-n3c4ccccc4c4ccccc43)cc2)cc1] | Appl. Phys. Lett.<br>78, 1622 (2001) |
| Metal<br>8-hydroxyquinolates<br>(eg., Alq$_3$, BAlq) | 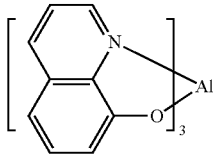 | Nature 395,<br>151 (1998) |
| | 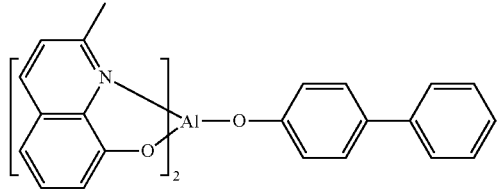 | US20060202194 |
| | 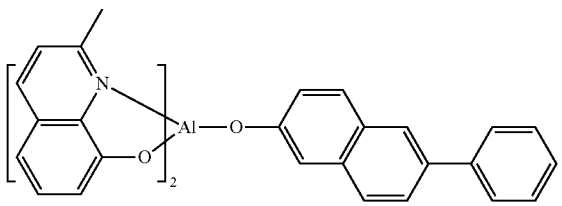 | WO2005014551 |
| | 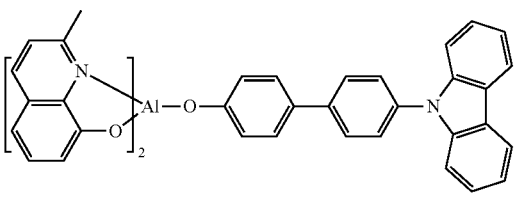 | WO2006072002 |
| Metal<br>phenoxybenzothiazole<br>compounds | 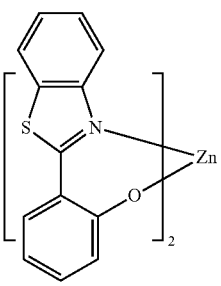 | Appl. Phys. Lett.<br>90, 123509 (2007) |
| Conjugated oligomers<br>and polymers<br>(e.g., polyfluorene) | 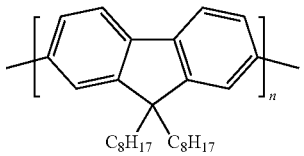 | Org. Electron. 1, 15<br>(2000) |

| MATERIAL | EXAMPLES OF MATERIAL | PUBLICATIONS |
|---|---|---|
| Aromatic fused rings | 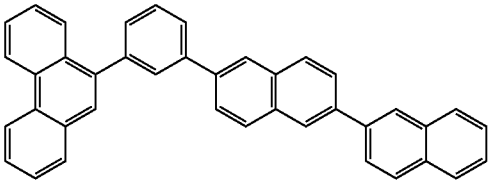 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |
| Zinc complexes | 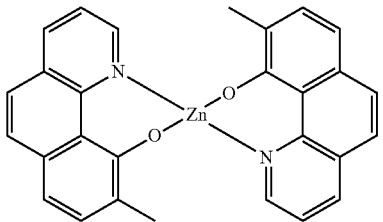 | WO2010056066 |
| Chrysene based compounds | 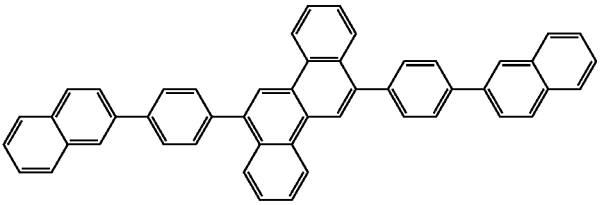 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
Green hosts
| | | |
|---|---|---|
| Arylcarbazoles | 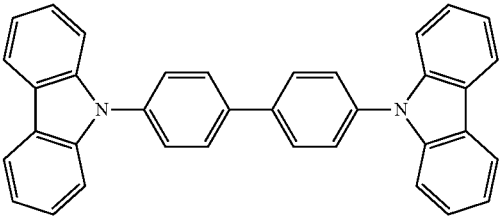 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 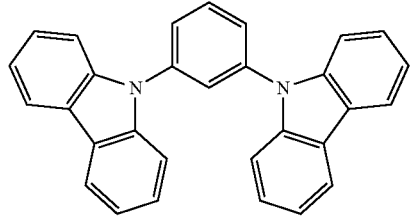 [SMILES: c1cc(-n2c3ccccc3c3ccccc32)cc(-n2c3ccccc3c3ccccc32)c1] | US20030175553 |
| | 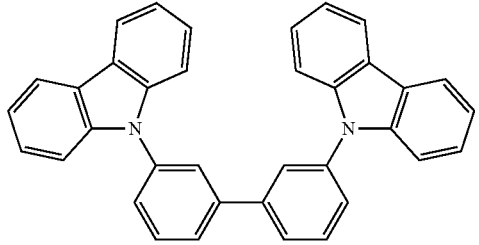 [SMILES: c1cc(-c2cccc(-n3c4ccccc4c4ccccc43)c2)cc(-n2c3ccccc3c3ccccc32)c1] | WO2001039234 |

TABLE 2-continued
| MATERIAL | EXAMPLES OF MATERIAL | PUBLICATIONS |
|---|---|---|
| Aryltriphenylene compounds | 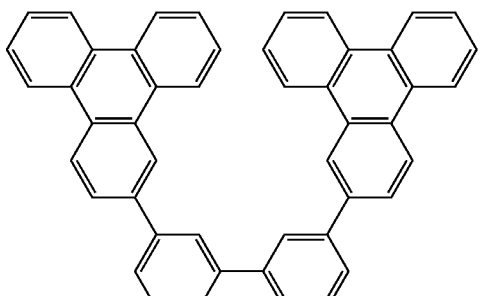 | US20060280965 |
| | 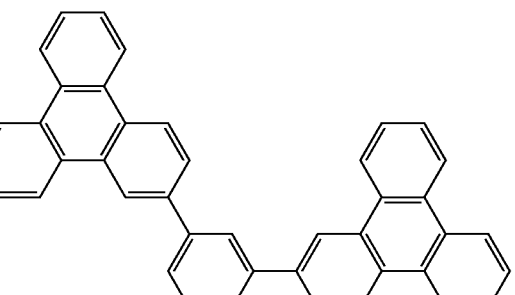 | US20060280965 |
| | 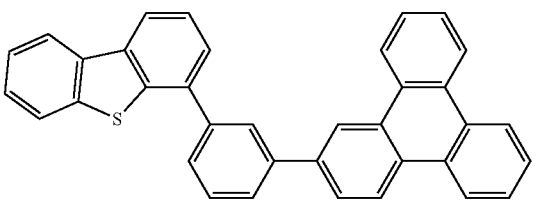 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 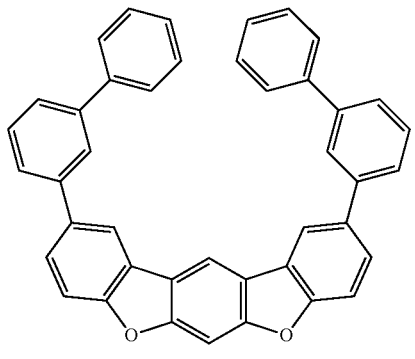 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 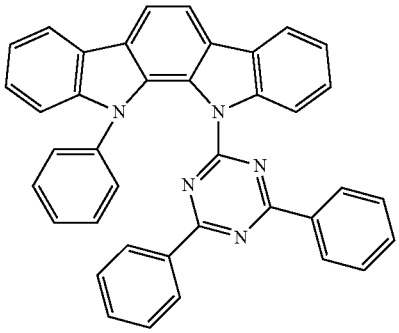 [SMILES: c1ccc(-c2nc(-c3ccccc3)nc(-n3c4ccccc4c4ccc5c6ccccc6n(-c6ccccc6)c5c43)n2)cc1] | WO2008056746 |

TABLE 2-continued
| MATERIAL | EXAMPLES OF MATERIAL | PUBLICATIONS |
|---|---|---|
| | 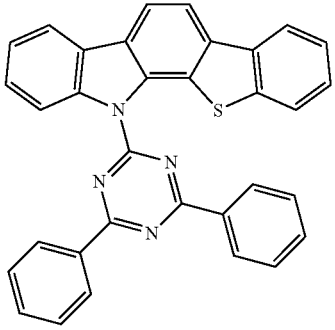 [SMILES: c1ccc(-c2nc(-c3ccccc3)nc(-n3c4ccccc4c4ccc5c6ccccc6sc5c43)n2)cc1] | WO2010107244 |
| Aza-carbazole/ DBT/DBF | 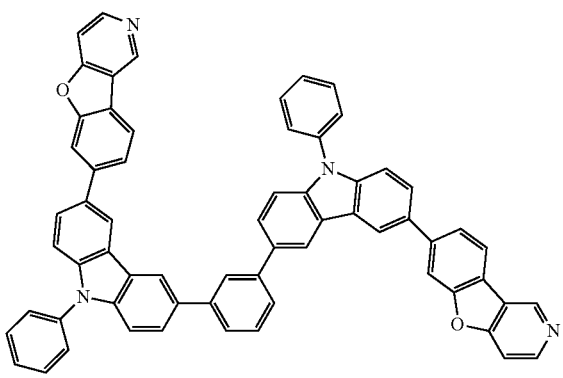 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 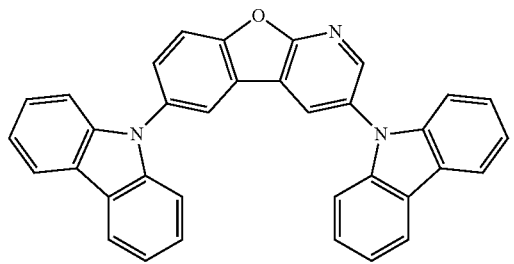 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 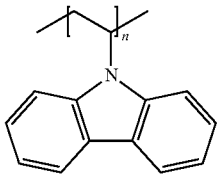 | Appl. Phys. Lett. 77, 2280 (2000) |
| Spirofluorene compounds | 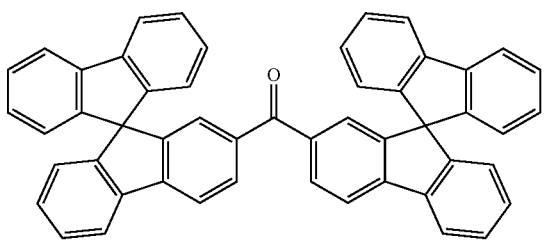 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |

TABLE 2-continued

| MATERIAL | EXAMPLES OF MATERIAL | PUBLICATIONS |
|---|---|---|
| Metal phenoxybenzooxazole compounds | | WO2005089025 |
| | | WO2006132173 |
| | | JP200511610 |
| Spirofluorene-carbazole compounds | | JP2007254297 |
| | | JP2007254297 |

TABLE 2-continued

| MATERIAL | EXAMPLES OF MATERIAL | PUBLICATIONS |
|---|---|---|
| Indolocabazoles | | WO2007063796 |
| | | WO2007063754 |
| 5-member ring electron deficient heterocycles (e.g., triazole, oxadiazole) | | J. Appl. Phys. 90, 5048 (2001) |
| | | WO2004107822 |
| Tetraphenylene complexes | | US20050112407 |

TABLE 2-continued
| MATERIAL | EXAMPLES OF MATERIAL | PUBLICATIONS |
|---|---|---|
| Metal phenoxypyridine compounds | 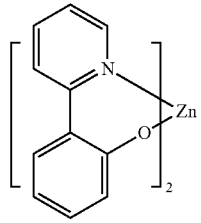 | WO2005030900 |
| Metal coordination complexes (e.g., Zn, Al with N^N ligands) | 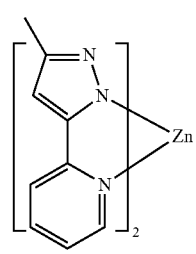 | US20040137268, US20040137267 |
Blue hosts
| | | |
|---|---|---|
| Arylcarbazoles | 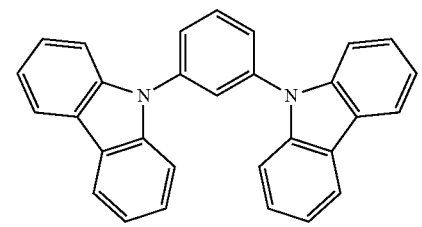 [SMILES: c1cc(-n2c3ccccc3c3ccccc32)cc(-n2c3ccccc3c3ccccc32)c1] | Appl. Phys. Lett, 82, 2422 (2003) |
| | 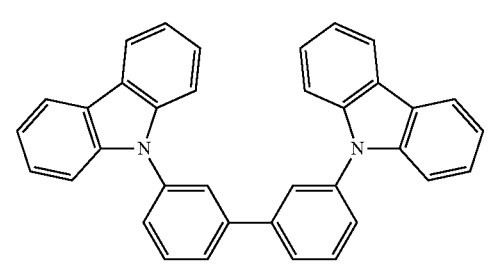 [SMILES: c1cc(-c2cccc(-n3c4ccccc4c4ccccc43)c2)cc(-n2c3ccccc3c3ccccc32)c1] | US20070190359 |
| Dibenzothiophene/ Dibenzofuran-carbazole compounds | 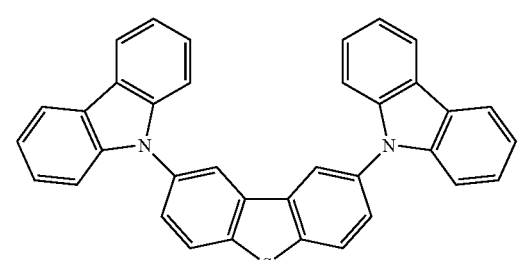 | WO2006114966, US20090167162 |
| | 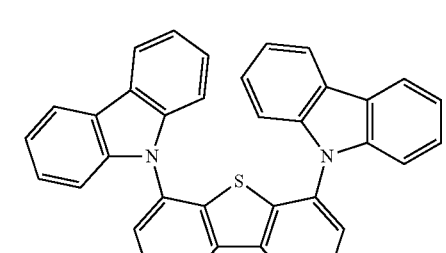 | US20090167162 |

TABLE 2-continued
| MATERIAL | EXAMPLES OF MATERIAL | PUBLICATIONS |
|---|---|---|
| | 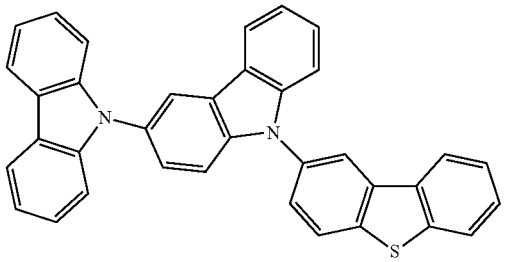 [SMILES: c1ccc2c(c1)sc1ccc(-n3c4ccccc4c4cc(-n5c6ccccc6c6ccccc65)ccc43)cc12] | WO2009086028 |
| | 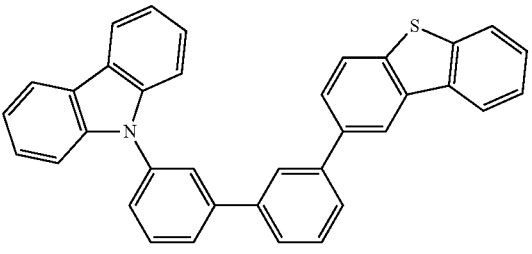 [SMILES: c1cc(-c2cccc(-n3c4ccccc4c4ccccc43)c2)cc(-c2ccc3sc4ccccc4c3c2)c1] | US20090030202, US20090017330 |
| | 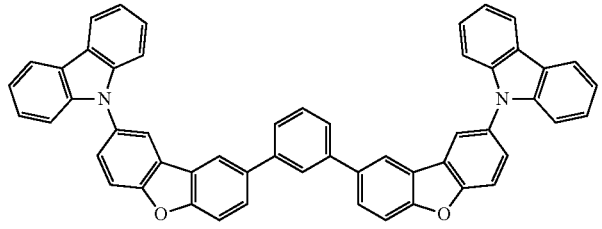 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 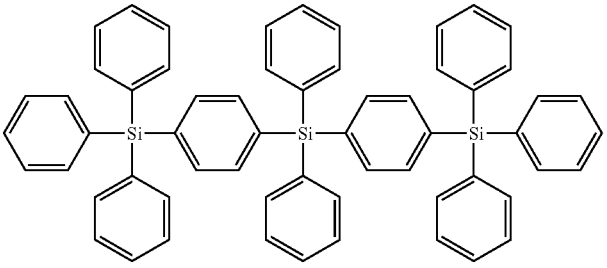 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 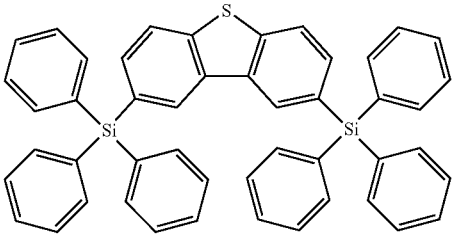 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 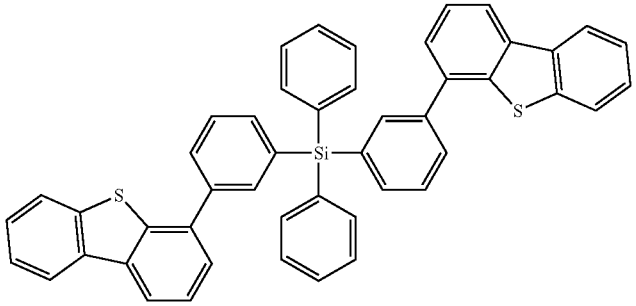 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |

TABLE 2-continued

| MATERIAL | EXAMPLES OF MATERIAL | PUBLICATIONS |
| --- | --- | --- |
| Aryl benzoyl ester | | WO2006100298 |
| Carbazole linked by non-conjugated groups | | US20040115476 |
| Aza-carbazoles | | US20060121308 |
| High triplet metal organometallic complex | | US7154114 |

Phosphorescent dopants
Red dopants

| Heavy metal porphyrins (e.g., PtOEP) | | Nature 395, 151 (1998) |
| --- | --- | --- |
| Iridium(III) organometallic complexes | | Appl. Phys. Lett. 78, 1622 (2001) |

TABLE 2-continued

| MATERIAL | EXAMPLES OF MATERIAL | PUBLICATIONS |
| --- | --- | --- |
| | | US2006835469 |
| | | US2006835469 |
| | | US20060202194 |
| | | US20060202194 |
| | | US20070087321 |

TABLE 2-continued

| MATERIAL | EXAMPLES OF MATERIAL | PUBLICATIONS |
|---|---|---|
| | | US20080261076<br>US20100090591 |
| | | US20070087321 |
| | | Adv. Mater. 19, 739 (2007) |
| | | WO2009100991 |
| | | WO2008101842 |

TABLE 2-continued
| MATERIAL | EXAMPLES OF MATERIAL | PUBLICATIONS |
|---|---|---|
| | 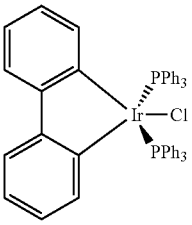 | US7232618 |
| Platinum(II) organometallic complexes | 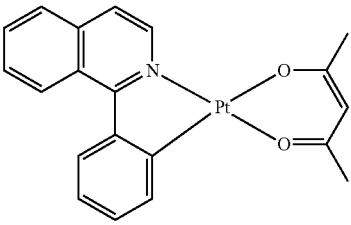 | WO2003040257 |
| | 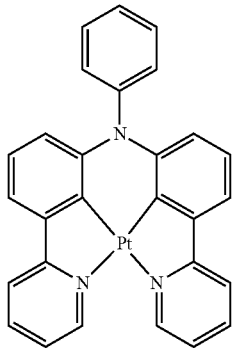 | US20070103060 |
| Osminum(III) complexes | 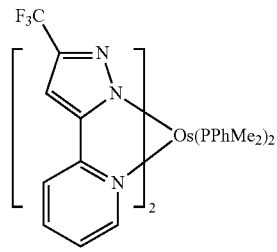 | Chem. Mater. 17, 3532 (2005) |
| Ruthenium(II) complexes | 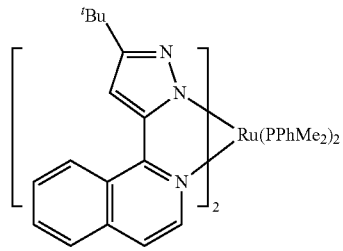 | Adv. Mater. 17, 1059 (2005) |
| Rhenium (I), (II), and (III) complexes | 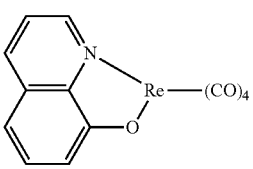 | US20050244673 |

TABLE 2-continued
| MATERIAL | EXAMPLES OF MATERIAL | PUBLICATIONS |
| --- | --- | --- |
| | Green dopants | |
| Iridium(III) organometallic complexes | 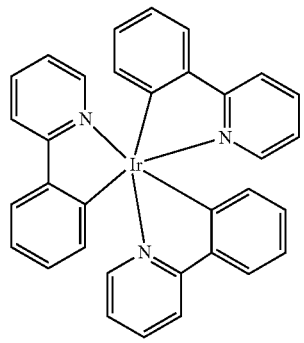
and its derivatives | Inorg. Chem. 40, 1704 (2001) |
| | 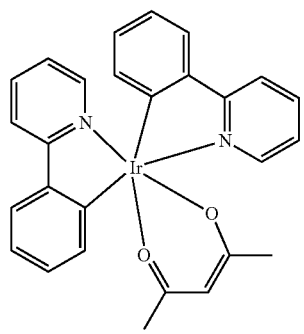 | US20020034656 |
| | 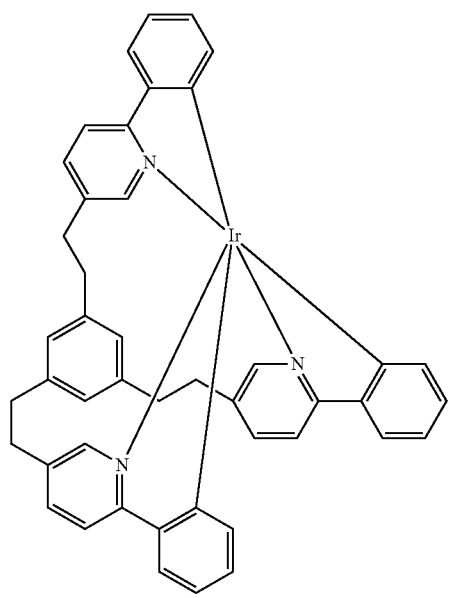 | US7332232 |

TABLE 2-continued
| MATERIAL | EXAMPLES OF MATERIAL | PUBLICATIONS |
|---|---|---|
| | 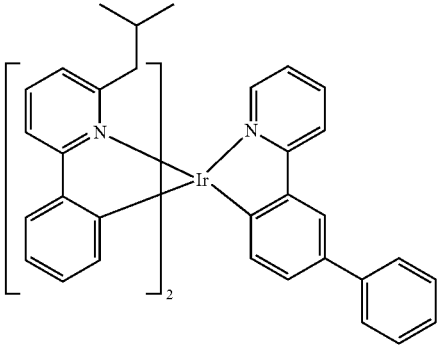 | US20090108737 |
| | 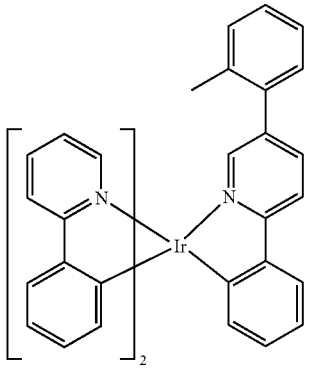 | WO2010028151 |
| | 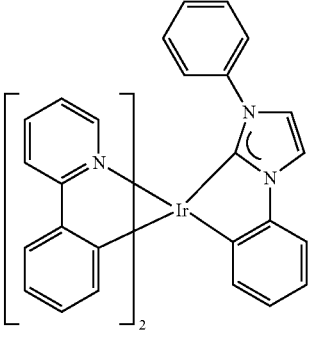 | EP1841834B |
| | 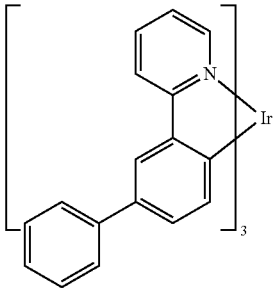 | US20060127696 |
| | 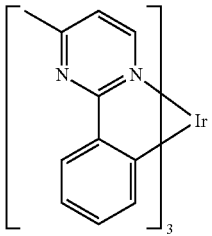 | US20090039776 |

TABLE 2-continued

| MATERIAL | EXAMPLES OF MATERIAL | PUBLICATIONS |
|---|---|---|
| | | US6921915 |
| | | US20100244004 |
| | | US6687266 |
| | | Chem. Mater. 16, 2480 (2004) |
| | | US20070190359 |

TABLE 2-continued

| MATERIAL | EXAMPLES OF MATERIAL | PUBLICATIONS |
|---|---|---|
| | | US 20060008670
JP2007123392 |
| | | WO2010086089,
WO2011044988 |
| | | Adv. Mater. 16,
2003 (2004) |
| | | Angew. Chem.
Int. Ed.
2006, 45, 7800 |
| | | WO2009050290 |
| | | US20090165846 |

TABLE 2-continued

| MATERIAL | EXAMPLES OF MATERIAL | PUBLICATIONS |
| --- | --- | --- |
| | | US20080015355 |
| | | US20010015432 |
| | | US20100295032 |
| Monomer for polymeric metal organometallic compounds | | US7250226, US7396598 |
| Pt(II) organometallic complexes, including polydentated ligands | | Appl. Phys. Lett. 86, 153505 (2005) |

TABLE 2-continued
| MATERIAL | EXAMPLES OF MATERIAL | PUBLICATIONS |
|---|---|---|
| | 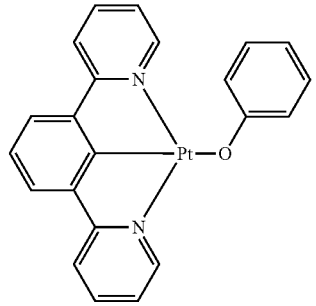 | Appl. Phys. Lett. 86, 153505 (2005) |
| | 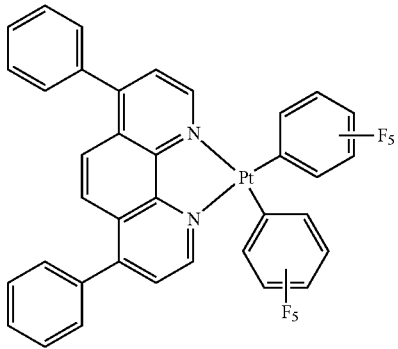 | Chem. Lett. 34, 592 (2005) |
| | 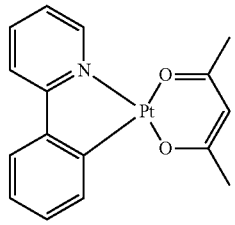 | WO2002015645 |
| | 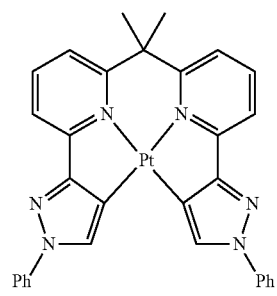 | US20060263635 |
| | 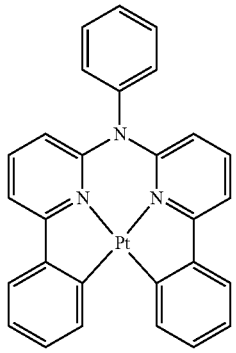 | US20060182992<br>US20070103060 |

TABLE 2-continued
| MATERIAL | EXAMPLES OF MATERIAL | PUBLICATIONS |
| --- | --- | --- |
| Cu complexes | 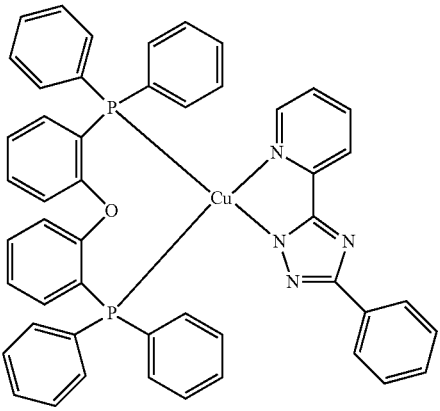 | WO2009000673 |
|  | 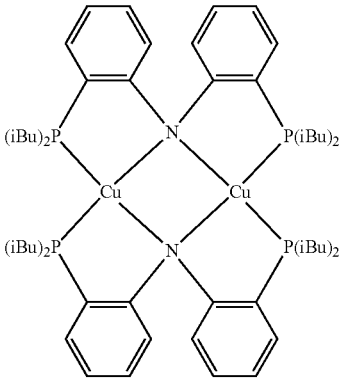 | US20070111026 |
| Gold complexes | 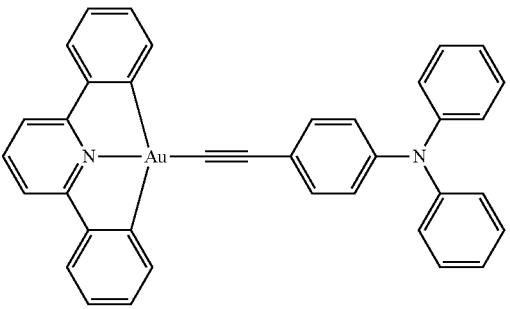 | Chem. Commun. 2906 (2005) |
| Rhenium(III) complexes | 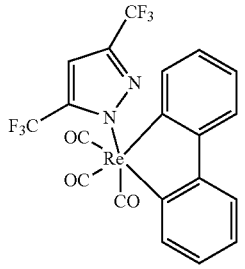 | Inorg. Chem. 42, 1248 (2003) |

TABLE 2-continued

| MATERIAL | EXAMPLES OF MATERIAL | PUBLICATIONS |
| --- | --- | --- |
| Osmium(II) complexes | | US7279704 |
| Deuterated organometallic complexes | | US20030138657 |
| Organometallic complexes with two or more metal centers | | US20030152802 |
| | | US7090928 |

TABLE 2-continued

| MATERIAL | EXAMPLES OF MATERIAL | PUBLICATIONS |
|---|---|---|
| | Blue dopants | |
| Iridium(III) organometallic complexes | | WO2002002714 |
| | | WO2006009024 |
| | | US20060251923<br>US20110057559<br>US20110204333 |
| | | US7393599,<br>WO2006056418,<br>US20050260441,<br>WO2005019373 |
| | | US7534505 |

TABLE 2-continued

| MATERIAL | EXAMPLES OF MATERIAL | PUBLICATIONS |
|---|---|---|
| | | WO2011051404 |
| | | US7445855 |
| | | US20070190359, US20080297033 US20100148663 |
| | | US7338722 |
| | | US20020134984 |

TABLE 2-continued
| MATERIAL | EXAMPLES OF MATERIAL | PUBLICATIONS |
|---|---|---|
| | 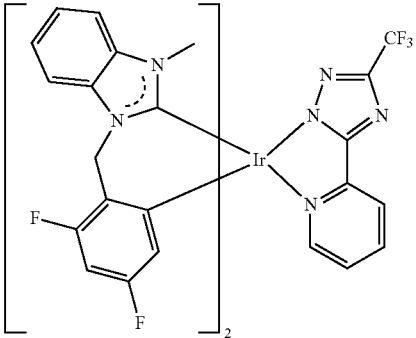 | Angew. Chem. Int. Ed. 47, 4542 (2008) |
| | 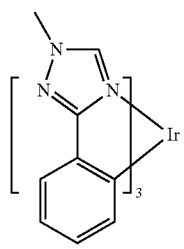 | Chem. Mater. 18, 5119 (2006) |
| | 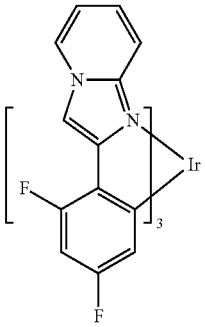 | Inorg. Chem. 46, 4308 (2007) |
| | 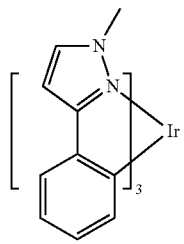 | WO2005123873 |
| | 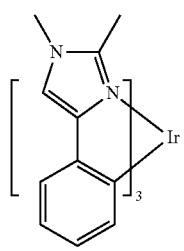 | WO2005123873 |

TABLE 2-continued

| MATERIAL | EXAMPLES OF MATERIAL | PUBLICATIONS |
|---|---|---|
| | | WO2007004380 |
| | | WO2006082742 |
| Osmium(II) complexes | | US7279704 |
| | | Organometallics 23, 3745 (2004) |
| Gold complexes | | Appl. Phys. Lett. 74, 1361 (1999) |
| Platinum(II) complexes | | WO2006098120, WO2006103874 |

TABLE 2-continued

| MATERIAL | EXAMPLES OF MATERIAL | PUBLICATIONS |
| --- | --- | --- |
| Pt tetradentate complexes with at least one metal-carbene bond | 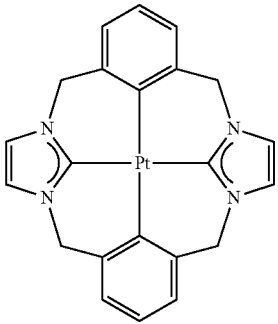 | US7655323 |

Exciton/hole blocking layer materials

| | | |
| --- | --- | --- |
| Bathocuprine compounds (e.g., BCP, BPhen) | 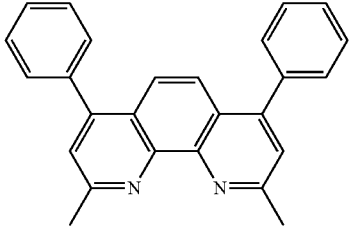 [SMILES: Cc1cc(-c2ccccc2)c2ccc3c(-c4ccccc4)cc(C)nc3c2n1] | Appl. Phys. Lett. 75, 4 (1999) |
| | 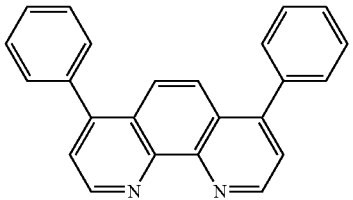 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 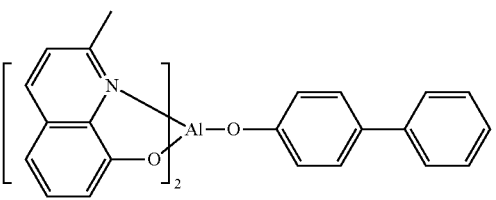 | Appl. Phys. Lett. 81, 162 (2002) |
| 5-member ring electron deficient heterocycles such as triazole, oxadiazole, imidazole, benzoimidazole | 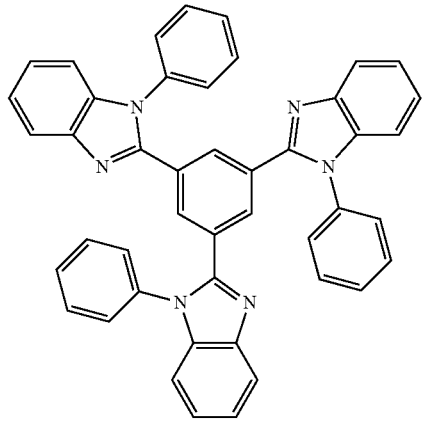 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE 2-continued
| MATERIAL | EXAMPLES OF MATERIAL | PUBLICATIONS |
|---|---|---|
| Triphenylene compounds | 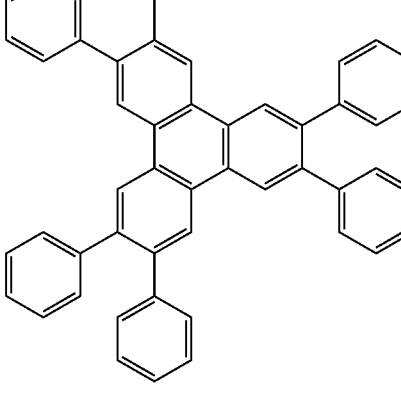 | US20050025993 |
| Fluorinated aromatic compounds | 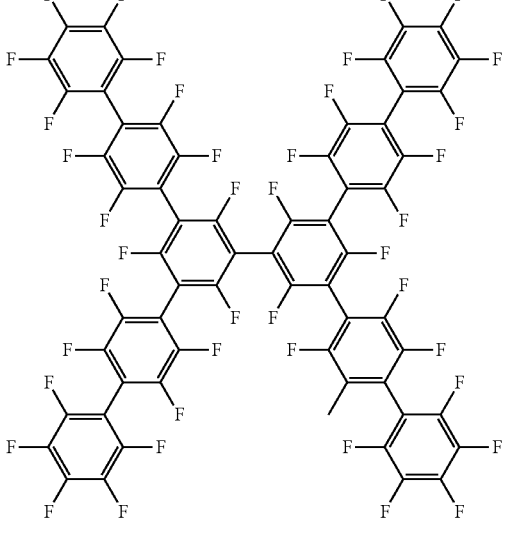 | Appl. Phys. Lett. 79, 156 (2001) |
| Phenothiazine-S-oxide | 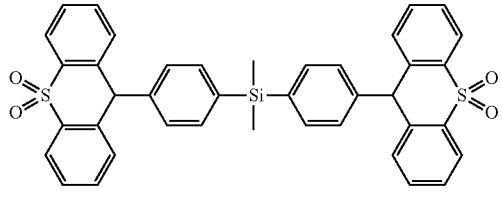 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 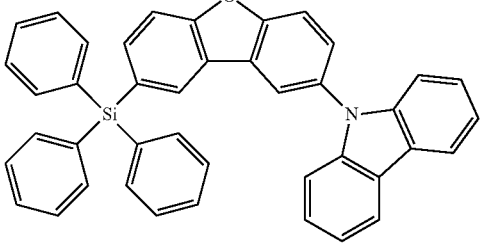 | WO2010079051 |

| MATERIAL | EXAMPLES OF MATERIAL | PUBLICATIONS |
|---|---|---|
| Aza-carbazoles | 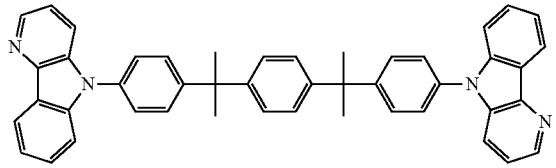 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 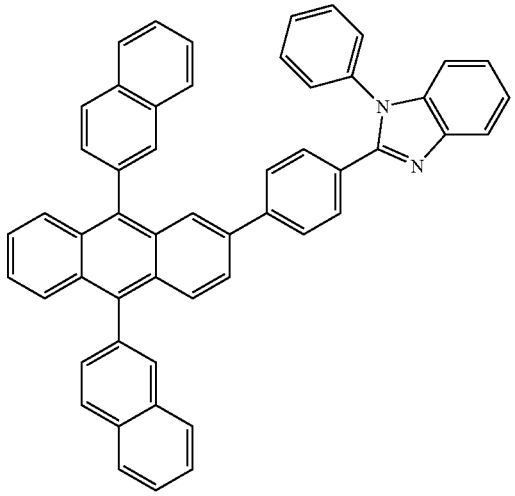 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 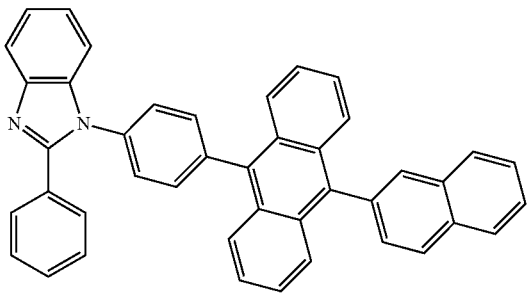 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 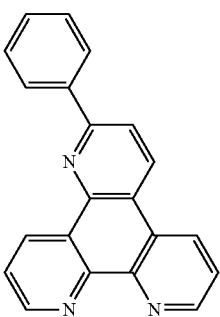 [SMILES: c1ccc(-c2ccc3c4cccnc4c4ncccc4c3n2)cc1] | US20090115316 |
| Anthracene-benzothiazole compounds | 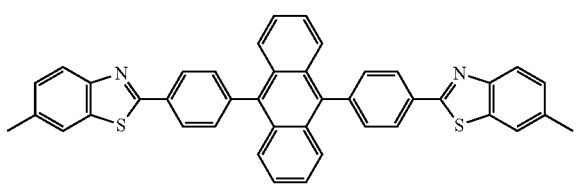 | Appl. Phys. Lett. 89, 063504 (2006) |

TABLE 2-continued

| MATERIAL | EXAMPLES OF MATERIAL | PUBLICATIONS |
| --- | --- | --- |
| Metal 8-hydroxyquinolates (e.g., Alq$_3$, Zrq$_4$) | | Appl. Phys. Lett. 51, 913 (1987) US7230107 |
| Metal hydroxybenoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE 2-continued

| MATERIAL | EXAMPLES OF MATERIAL | PUBLICATIONS |
|---|---|---|
| | (triazole structure) | Jpn. J. Apply. Phys. 32, L917 (1993) |
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |
| Fullerene (e.g., C60) | | US20090101870 |
| Triazine complexes | | US20040036077 |

TABLE 2-continued

| MATERIAL | EXAMPLES OF MATERIAL | PUBLICATIONS |
|---|---|---|
| Zn (N^N) complexes | | US6528187 |

Experimental—Synthesis of Example Compounds

Synthesis of Compound 3

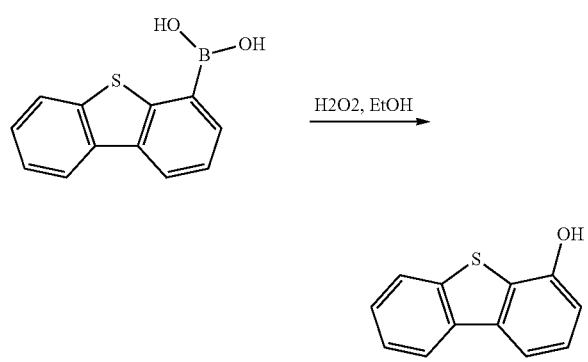 [SMILES: OB(O)c1cccc2c1sc1ccccc12 ; Oc1cccc2c1sc1ccccc12]

$H_2O_2$ (30% aqueous solution, 8.96 ml, 88 mmol) was added dropwise to a mixture of dibenzo[b,d]thiophen-4-ylboronic acid (10 g, 43.8 mmol) in ethanol (120 ml) at room temperature. The mixture was stirred at ambient temperature for two hours. Upon evaporation of the ethanol, the reaction product was diluted with water and extracted with EtOAc (4×25 mL). The organic extract was washed with NaHCO$_3$, dried and evaporated. The product was recrystallized from DCM/AcOEt/Hexane (2/1/7) to give a white solid (4.3 g, 49% yield).

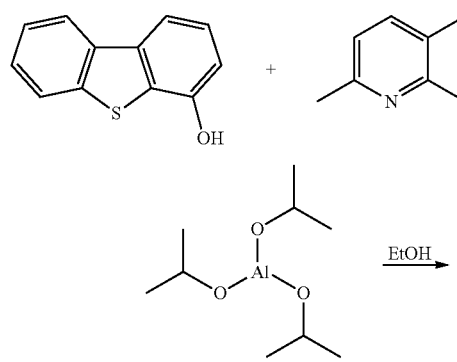

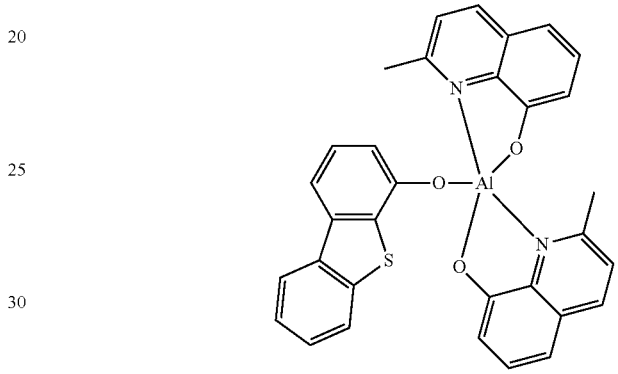

2-Methylquinolin-8-ol (1.590 g, 9.99 mmol) and triisopropoxyaluminum (2.040 g, 9.99 mmol) were dissolved in EtOH (80 ml). The mixture was refluxed for two hours under N$_2$. The mixture was cooled down. To this mixture was added 2-methylquinolin-8-ol (1.590 g, 9.99 mmol) and dibenzo[b,d]thiophen-4-ol (2.0 g, 9.99 mmol) in 80 mL of EtOH. The mixture was then refluxed under N$_2$ overnight, then it was cooled down to 50° C., filtered yellow solid, washed with EtOH to afford Compound 3 in the form of a greenish powder (4.3 g, 79% yield).

Synthesis of Compound 31

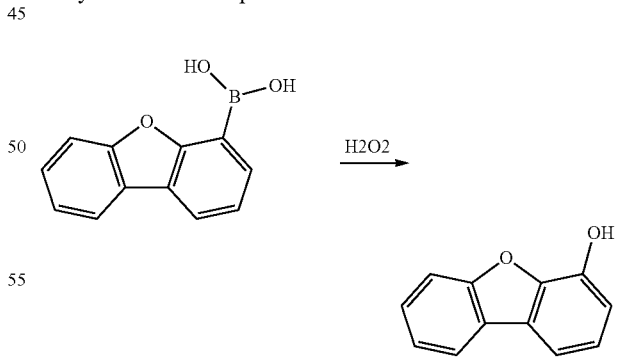

Dibenzo[b,d]furan-4-ylboronic acid (6 g, 28.3 mmol), was dissolved in ethanol (60 ml), added H$_2$O$_2$ (30% aqueous solution, 8.67 ml, 85 mmol) and stirred at 60° C. for 2 h. Added 300 mL of water, extracted with EtOAc (3×40 mL), organic fractions were combined, filtered and evaporated. The solid residue was crystallized two times from DCM/hexane, providing dibenzo[b,d]furan-4-ol as colorless needles (3 g, 16.29 mmol, 57.6% yield).

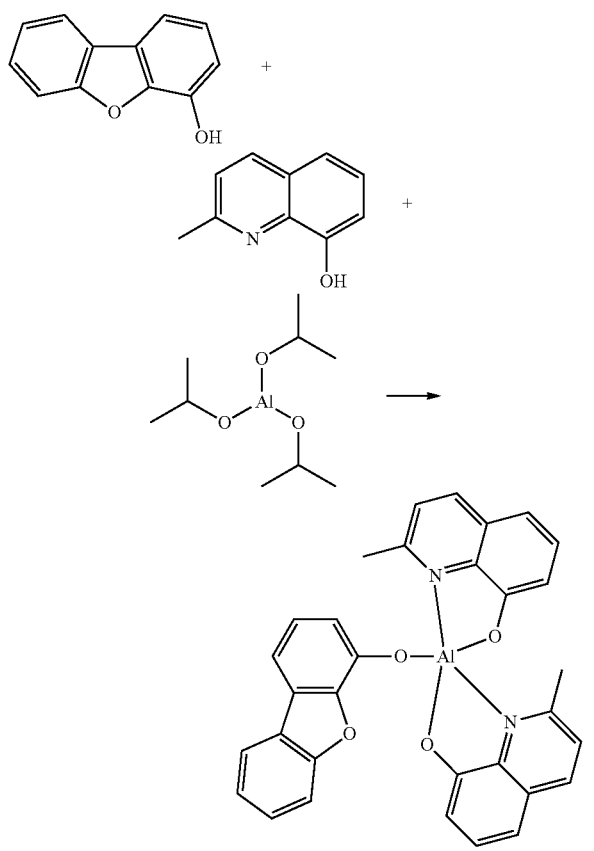

2-Methylquinolin-8-ol (1.800 g, 11.31 mmol) and triisopropoxyaluminum (2.310 g, 11.31 mmol) were dissolved in EtOH (75 ml), refluxed 2 h under N$_2$. Then added 2-methylquinolin-8-ol (1.800 g, 11.31 mmol) and dibenzo[b,d]furan-4-ol (2.083 g, 11.31 mmol) in 75 mL of EtOH, refluxed overnight, cooled down, filtered yellow solid (4.1 g, 62% yield) of Compound 31.

Synthesis of Compound 86

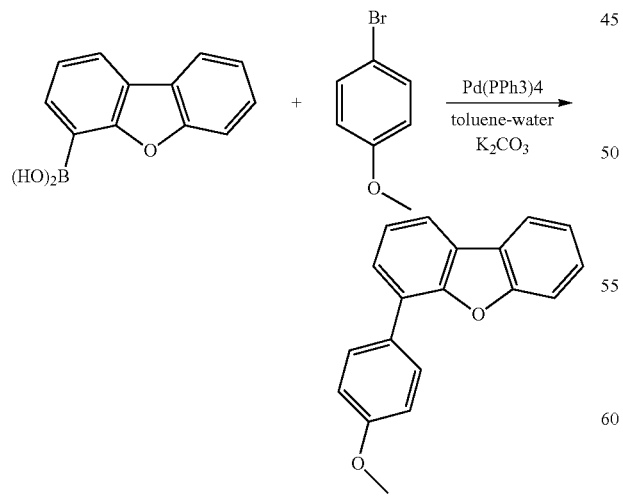

Dibenzo[b,d]furan-4-ylboronic acid (4.00 g, 18.87 mmol) and 1-bromo-4-methoxybenzene (5.29 g, 28.3 mmol) were dissolved in toluene (100 ml). Potassium carbonate (5.22 g, 37.7 mmol) in water (20 ml) was added. The reaction was bubbled with N$_2$, and Pd(PPh$_3$)$_4$ (0.436 g, 0.377 mmol) was then added. The reaction was degassed and heated to reflux overnight. The solution was cooled down. The organic layer was separated. The crude product was purified by column chromatography on silica gel, eluted with hexane/DCM 9/1 to 1/1 (v/v) gradient mixture to give a white solid (3.7 g, 72%).

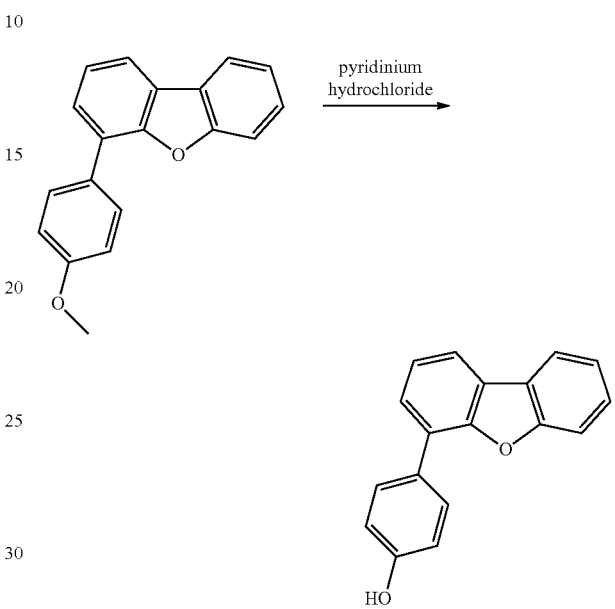

4-(4-Methoxyphenyl)dibenzo[b,d]furan (3.70 g, 13.49 mmol) and pyridinium hydrochloride (15.59 g, 135 mmol) were placed in the round-bottom flask with magnetic stirrer under N$_2$ atm. The flask was placed in the oil bath at 220° C., cooled down to 120° C., added excess of water, and stirred for 1 h. The resulting product was extracted with ethyl acetate. The organic layer was washed with water several times. The solvent was evaporated. The crude product was purified by column chromatography on silica gel, eluted with hexane/ethyl acetate 1/1 (v/v) to provide of 2-Methylquinolin-8-ol (2.1 g, 60%).

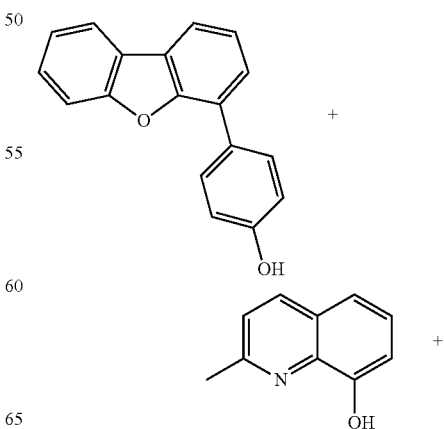

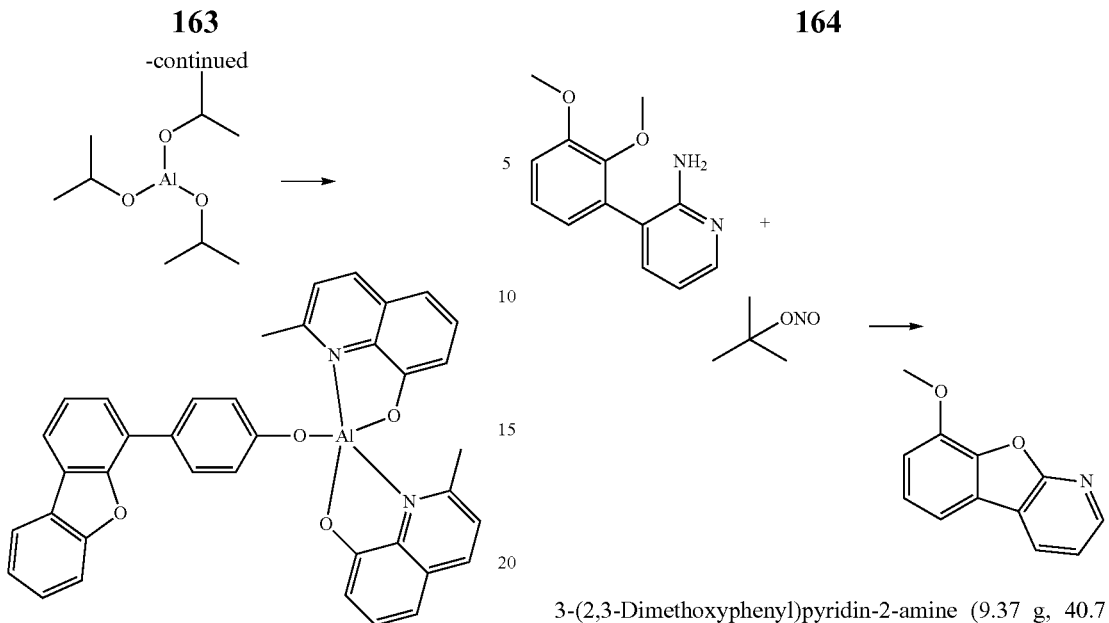

2-Methylquinolin-8-ol (0.734 g, 4.61 mmol) and triisopropoxyaluminum (0.942 g, 4.61 mmol) were suspended in EtOH (10 ml), heated to 100° C. for 2 h. A mixture of 2-methylquinolin-8-ol (0.734 g, 4.61 mmol) and 4-(dibenzo[b,d]furan-4-yl)phenol (1.200 g, 4.61 mmol) in EtOH (10 ml) was added as one portion to the hot reaction mixture, forming slightly cloudy solution. After 30 min of refluxing white solid precipitated. The solution was stirred overnight at 90° C. Compound 86 in yellow solid form was filtered off, washed with hexane and dried (2.3 g, 83%).

Synthesis of Compound 157

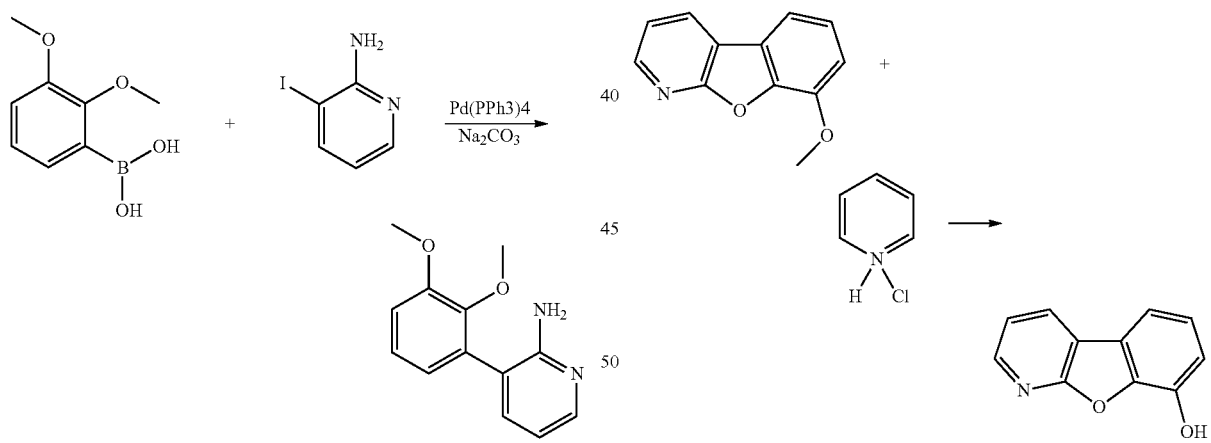

(2,3-Dimethoxyphenyl)boronic acid (4.33 g, 23.82 mmol) and 3-iodopyridin-2-amine (5.24 g, 23.82 mmol) were suspended in THF (200 ml). Sodium carbonate (5.05 g, 47.6 mmol) in 50 mL of water was added. The reaction was bubbled with $N_2$ for 30 min. Pd(PPh$_3$)$_4$ catalyst (0.688 g, 0.595 mmol) was added. The reaction was warmed up to 80° C., stirred overnight under $N_2$. The mixture was diluted with 80 mL of EtOAc, washed with NaCl saturated solution. The solvent was evaporated and the crude product was purified by column chromatography on silica gel, and eluted with hexane/EtOAc 1/1 (v/v) to provide a product of 3-(2,3-Dimethoxyphenyl)pyridin-2-amine as white solid material (3.8 g, 63% yield).

3-(2,3-Dimethoxyphenyl)pyridin-2-amine (9.37 g, 40.7 mmol) was dissolved in the mixture of AcOH (120 ml) and 20 mL of THF, cooled in the ice bath. tert-Butyl nitrite (8.39 g, 73.2 mmol) in 20 mL of THF was added. The reaction was warmed up to RT. The solvent was evaporated to about half of the volume. The reaction was then diluted with brine, extracted with EtOAc (4×25 mL). The organic fractions were combined, washed with Na2CO3 aq., dried over Na$_2$SO$_4$ and evaporated 2/3 of solvent. Yellow crystals formed and the crystals were filtered off and dried. The remaining material was purified by chromatography on silica gel, eluted with hexane/EtOAc 1/1 (v/v), providing yellow solid of 8-Methoxybenzofuro[2,3-b]pyridine. Total yield was 4.2 g, 52%.

8-Methoxybenzofuro[2,3-b]pyridine (5.00 g, 25.10 mmol) and pyridinium hydrochloride (14.50 g, 125 mmol) were immersed in the oil bath at 190° C. The reaction was heated for 5 h upon vigorous stirring. The mixture was cooled to 100° C. Water was added and the reaction was stirred overnight resulting in formation of grey solid. The grey solid was filtered, washed with a generous amount of water, then dried in a vacuum oven. The solid material was refluxed with 50 ml of DCM; then 50 ml of hexane was added. The mixture was refluxed and cooled down. The solid material was filtered and dried. The resulting product of 2-Methylquinolin-8-ol was obtained as grey solid. (4 g, 85% yield).

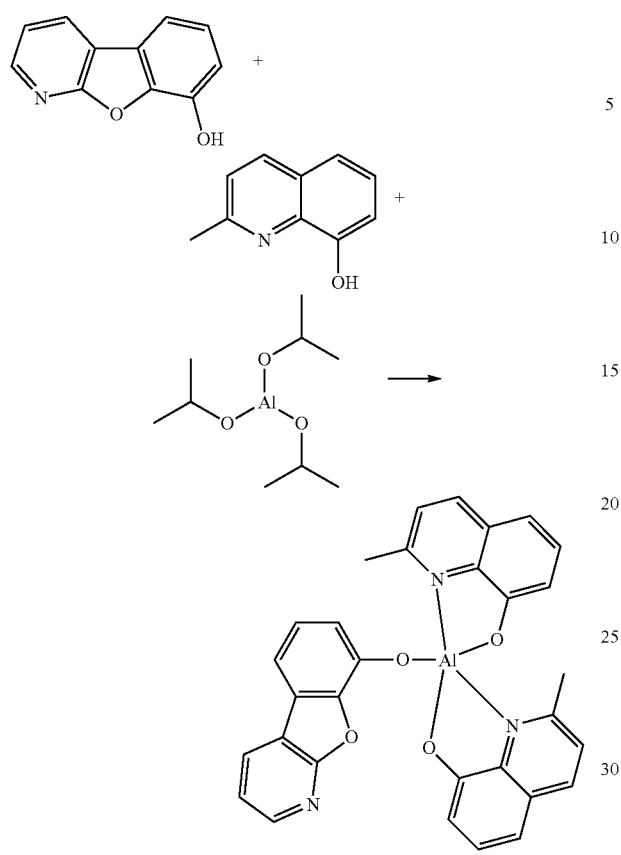

2-Methylquinolin-8-ol (1.393 g, 8.75 mmol) and triisopropoxyaluminum (1.787 g, 8.75 mmol) were suspended together in 120 mL of abs. ethanol and heated to reflux upon vigorous stirring under nitrogen atmosphere. After 1 h, yellow slightly cloudy reaction mixture was filtered through celite, providing Solution A.

A solution of 2-methylquinolin-8-ol (1.393 g, 8.75 mmol) and benzofuro[2,3-b]pyridin-8-ol (1.620 g, 8.75 mmol) in 50 mL of EtOH was prepared and called Solution B. Solution B was added to the solution A. The mixture was refluxed for 12 h. the solid was filtered to give Compound 157 (2.8 g, 5 mmol, 57%).

Properties of Synthesized Materials:

TABLE 3

| Compound | Deposition Temperature, ° C. | Tg ° C. |
|---|---|---|
| Compound 31 | 200 | 108 |
| Compound 3 | 240 | 120 |
| Compound 157 | 210 | 115 |
| Compound 86 | 265 | 123 |
| Comparative Compound | 200 | 92 |

As one can see, synthesized compounds have significantly better (higher) glass transition temperature (Tg) than the Comparative Compound while having deposition temperatures low enough for VTE process.

Device Examples

All example devices were fabricated by high vacuum ($<10^{-7}$ Torr) thermal evaporation. The anode electrode is 1200 Å of indium tin oxide (ITO). The cathode consisted of 10 Å of LiF followed by 1,000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

Compounds were tested in two device structures: Structure 1 and Structure 2. The compounds used in device fabrication have the following chemical structures:

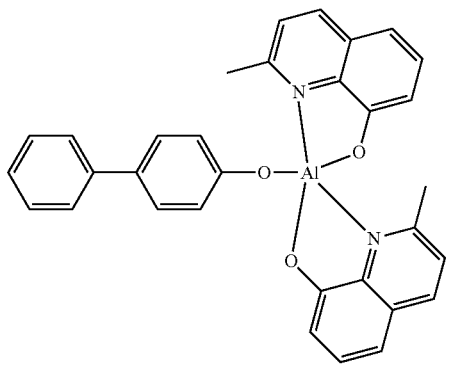

Comparative compound

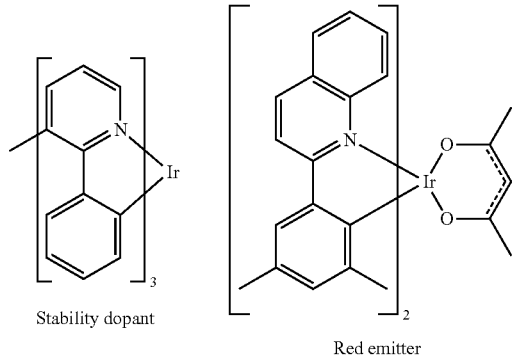

Stability dopant

Red emitter

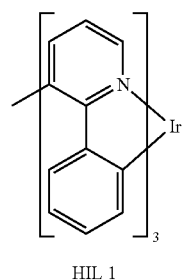

HIL 1

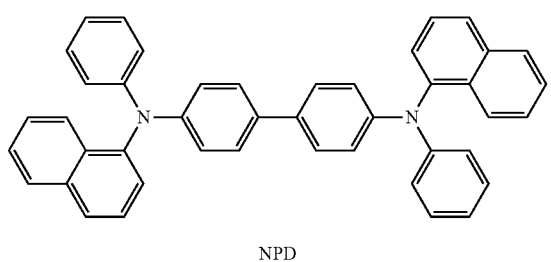

NPD

-continued

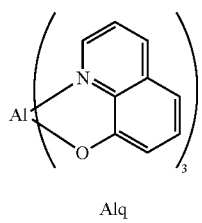

Alq

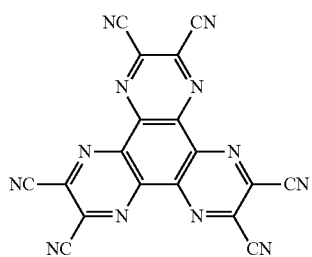

HIL 2

Device Structure 1 (the Compound as Host):

The organic stack of the device consisted of sequentially, from the ITO surface, 100 Å of Compound HIL 1 as the hole injection layer (HIL), 400 Å of 4,4'-bis[N-(1-naphthyl)-N-phenylamino]biphenyl (NPD) as the hole transporting layer (HTL), 300 Å of the invention compound as host doped with Stability dopant and Red emitter in a ratio 87:10:3 forming the emissive layer (EML), and 550 Å of Alq₃ (tris-8-hydroxyquinoline aluminum) as the electron transporting layer (ETL). Comparative Examples with Comparative Compound were fabricated similarly to the Device Examples except that the Comparative Compound was used as the host in the EML.

Device Structure 2 (Compound as Host and/or BL):

The organic stack of the device consisted of sequentially, from the ITO surface, 100 Å of Compound HIL 1 as the HIL, 400 Å of NPD as the HTL, 300 Å of the invention compound as host doped with Red emitter in a ratio 91:9 forming the EML, 100 Å of Compound 31 or Comparative Compound as hole Blocking Layer (BL), 450 Å of Alq₃ (tris-8-hydroxyquinoline aluminum) as the ETL. Comparative Examples with Comparative Compound was fabricated similarly to the Device Examples except that the Comparative Compound was used as the host in the EML.

The example devices were evaluated and their performance data are summarized in Tables 4 and 5 below.

TABLE 4

Device Performances of Compound 157 vs. Comparative Compound in Device Structure 1

| | At 1,000 nits | | | | | |
|---|---|---|---|---|---|---|
| | 1931 CIE | | Voltage | LE | EQE | PE |
| Host | CIE x | CIE y | (relative units) | (relative units) | (relative units) | (relative units) |
| Compound 157 | 0.667 | 0.333 | 0.90 | 1.28 | 1.30 | 1.42 |
| Comparative Compound | 0.663 | 0.336 | 1 | 1 | 1 | 1 |

Comparison of Compound 157 and Comparative Compound in Device Structure 1 configuration shows similar CIE color coordinates but Compound 157 exhibited surprisingly improved voltage, luminous efficiency (LE), external quantum efficiency (EQE) and power efficiency (PE).

TABLE 5

Device performances of Compound 31 vs. Comparative Compound in Device Structure 2

| | | At 1,000 nits | | | | |
|---|---|---|---|---|---|---|
| | | 1931 CIE | | Voltage | LE | EQE (relative units) | PE (relative units) |
| Host | BL | CIE x | CIE y | (relative units) | (relative units) | | |
| Comp. Compound | Comp. Compound | 0.670 | 0.327 | 1 | 1 | 1 | 1 |
| Cmpd. 31 | Comp. Compound | 0.672 | 0.327 | 0.92 | 1.04 | 1.03 | 1.14 |
| Cmpd. 31 | Cmpd. 31 | 0.672 | 0.328 | 0.90 | 1.04 | 1.02 | 1.18 |
| Comp. 3 | Comp. Compound | 0.674 | 0.326 | 0.98 | 1 | 1.03 | 1.05 |
| Comp. 86 | Comp. Compound | 0.672 | 0.327 | 0.91 | 1.04 | 1.03 | 1.15 |

Comparison of Compounds 3, 31, and 86 and Comparative Compound in Device Structure 2 demonstrates same color coordinates with improved voltage, EQE and PE of the device. Using Compound 31 as both the host and BL some additional improvement in voltage and PE. This suggests that the inventive compounds are suitable to be used as BL in combination with being used as the host material.

Based on the experimental device data shown above, the inventors found that replacement of biphenyl fragment of the host molecule by DBT- or DBF-containing fragment improved such important parameters of the device as voltage, EQE, and power efficiency. Improvement of other important parameter of OLED material as Tg was also observed.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound having a structure according to Formula I

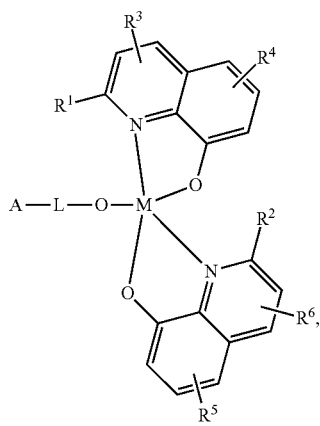

Formula I wherein M is a group III element;
wherein L is selected from the group consisting of

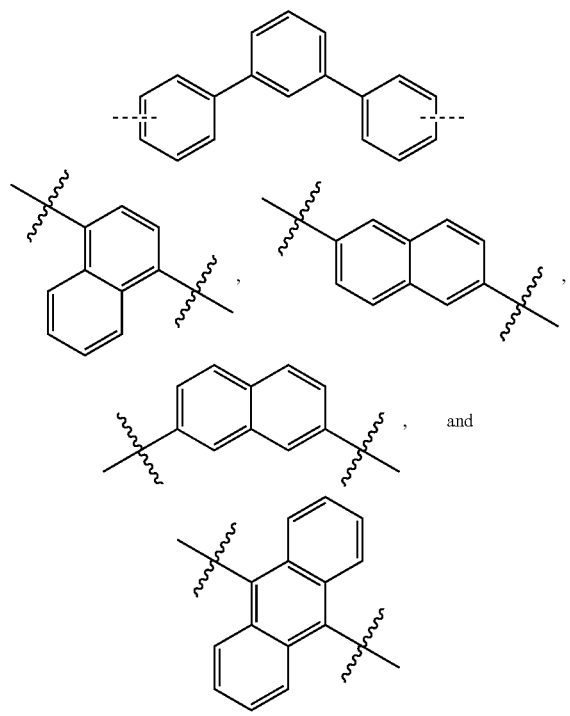

and L is optionally further substituted with one or more groups selected from hydrogen, deuterium, alkyl, cycloalkyl, aralkyl, alkoxy, aryloxy, amino, silyl, aryl, heteroaryl, and combinations thereof;

wherein A contains a group selected from the group consisting of dibenzoselenophene, aza-dibenzofuran, aza-dibenzothiophene, aza-dibenzoselenophene, and combination thereof, which are optionally further substituted with one or more groups selected from hydrogen, deuterium, alkyl, cycloalkyl, aralkyl, alkoxy, aryloxy, amino, silyl, aryl, heteroaryl, and combinations thereof;

wherein $R^3$ and $R^6$ each represent mono, di substitutions, or no substitution;

wherein $R^4$ and $R^5$ each represent mono, di, tri substitutions, or no substitution; and wherein $R^1$, $R^2$, $R^3$, $R^4$, $R^5$, and $R^6$ are each independently selected from the group consisting of hydrogen, deuterium, alkyl, cycloalkyl, aralkyl, alkoxy, aryloxy, amino, silyl, aryl, heteroaryl, and combinations thereof.

2. The compound of claim 1, wherein M is selected from the group consisting of Al, In and Ga.

3. The compound of claim 1, wherein M is Al.

4. The compound of claim 1, wherein L is

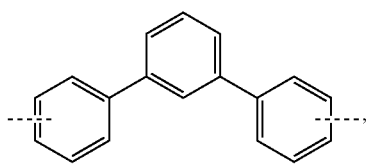

5. The compound of claim 1, wherein A is selected from the group consisting of:

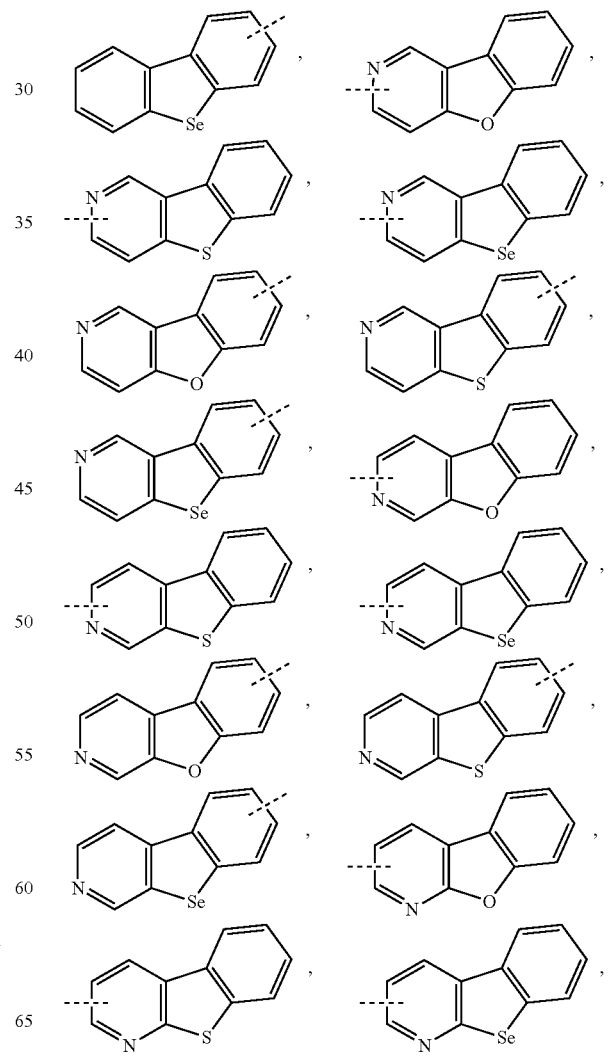

-continued

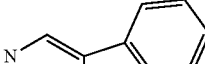

6. The compound of claim 1, wherein $R^1$ and $R^2$ are each independently selected from the group consisting of hydrogen, deuterium, methyl, ethyl, propyl, iso-propyl, and combinations thereof.

7. The compound of claim 1, wherein M is aluminum; and wherein $R^3$, $R^4$, $R^5$ and $R^6$ are hydrogen.

8. The compound of claim 7, wherein L is selected from the group consisting of

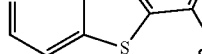

9. The compound of claim 7, wherein A is selected from the group consisting of

-continued

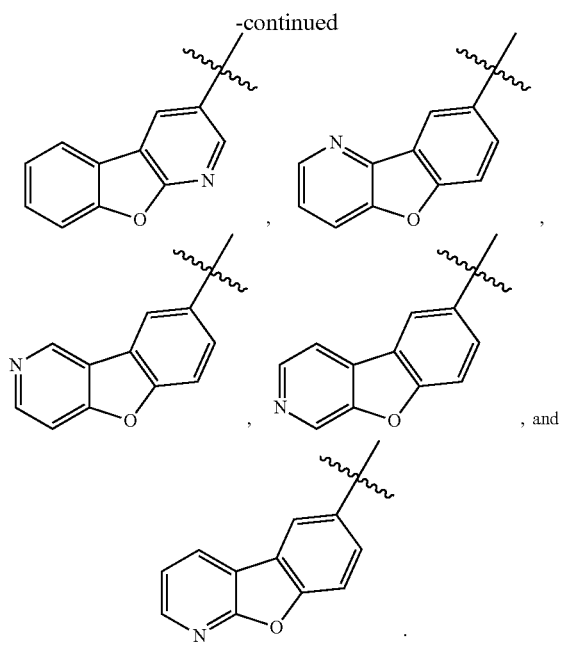

, and

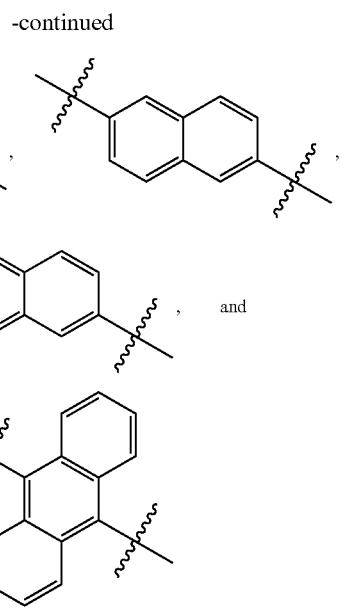

10. A formulation comprising a compound of claim 1.

11. A first device comprising a first organic light emitting device, further comprising:
an anode;
a cathode;
an organic layer, disposed between the anode and the cathode, comprising a compound having a structure according to Formula I Formula I

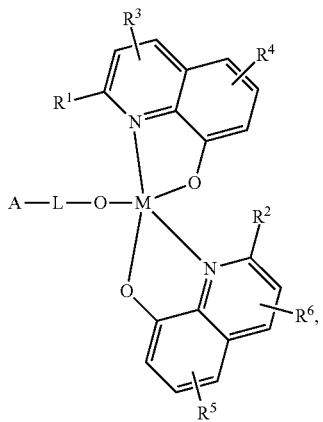

wherein M is a group III element;
wherein L is selected from the group consisting of

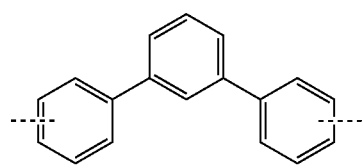

and L is optionally further substituted with one or more groups selected from hydrogen, deuterium, alkyl, cycloalkyl, aralkyl, alkoxy, aryloxy, amino, silyl, aryl, heteroaryl, and combinations thereof;

wherein A contains a group selected from the group consisting of dibenzoselenophene, aza-dibenzofuran, aza-dibenzothiophene, aza-dibenzoselenophene, and combination thereof, which are optionally further substituted with one or more groups selected from hydrogen, deuterium, alkyl, cycloalkyl, aralkyl, alkoxy, aryloxy, amino, silyl, aryl, heteroaryl, and combinations thereof;

wherein $R^3$ and $R^6$ each represent mono, di substitutions, or no substitution;

wherein $R^4$ and $R^5$ each represent mono, di, tri substitutions, or no substitution; and wherein $R^1$, $R^2$, $R^3$, $R^4$, $R^5$, and $R^6$ are each independently selected from the group consisting of hydrogen, deuterium, alkyl, cycloalkyl, aralkyl, alkoxy, aryloxy, amino, silyl, aryl, heteroaryl, and combinations thereof.

12. The first device of claim 11, wherein M is selected from the group consisting of Al, In and Ga.

13. The first device of claim 11, wherein M is Al.

14. The first device of claim 11, wherein L is

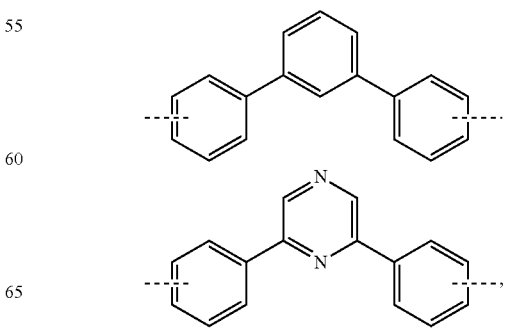

15. The first device of claim 11, wherein A is selected from the group consisting of:

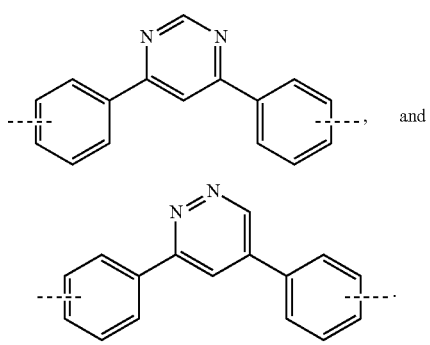

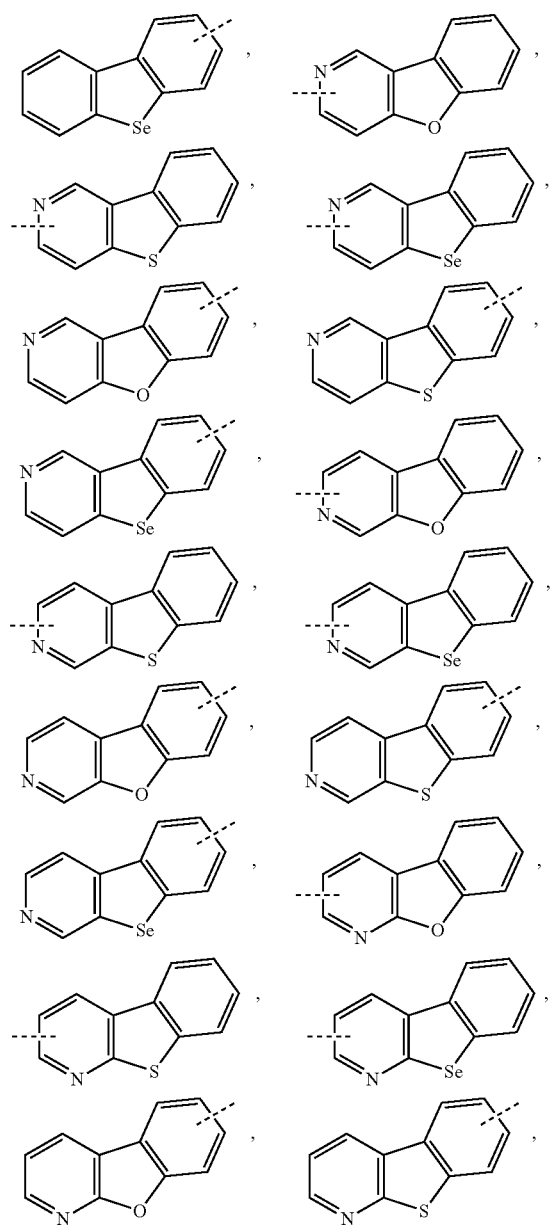

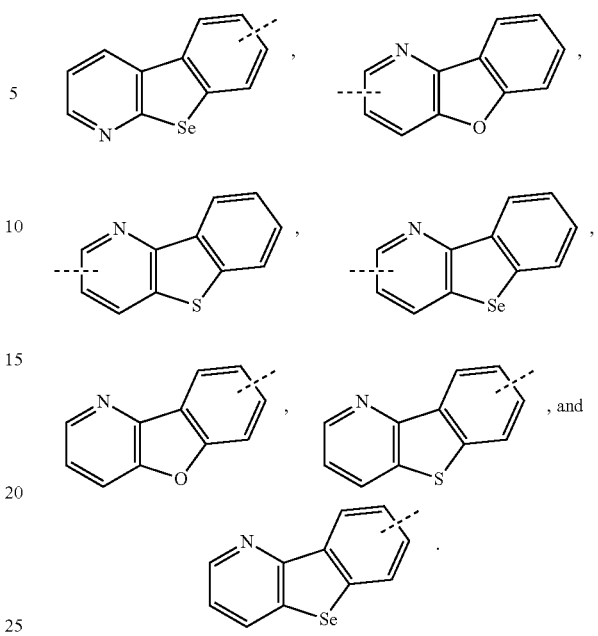

16. The first device of claim 11, wherein M in the compound is aluminum; and wherein $R^3$, $R^4$, $R^5$ and $R^6$ are hydrogen.

17. The first device of claim 11, wherein the organic layer is an emissive layer and the compound having Formula I is a host.

18. The first device of claim 11, wherein $R^1$ and $R^2$ are each independently selected from the group consisting of hydrogen, deuterium, methyl, ethyl, propyl, iso-propyl, and combinations thereof.

19. The first device of claim 17, wherein the organic layer further comprises an emissive dopant.

20. The first device of claim 19, wherein the emissive dopant is a transition metal complex having at least one ligand selected from the group consisting of:

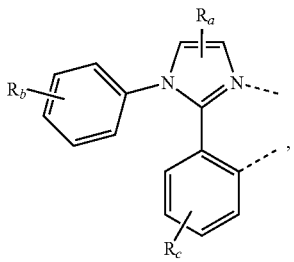

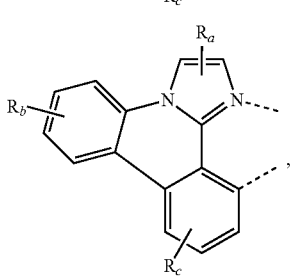

-continued

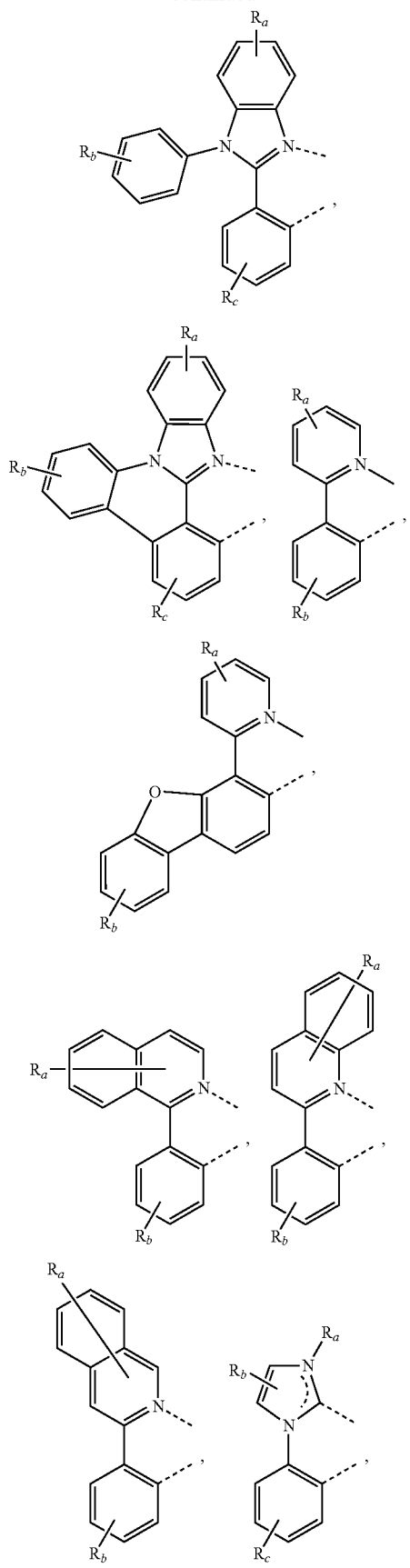

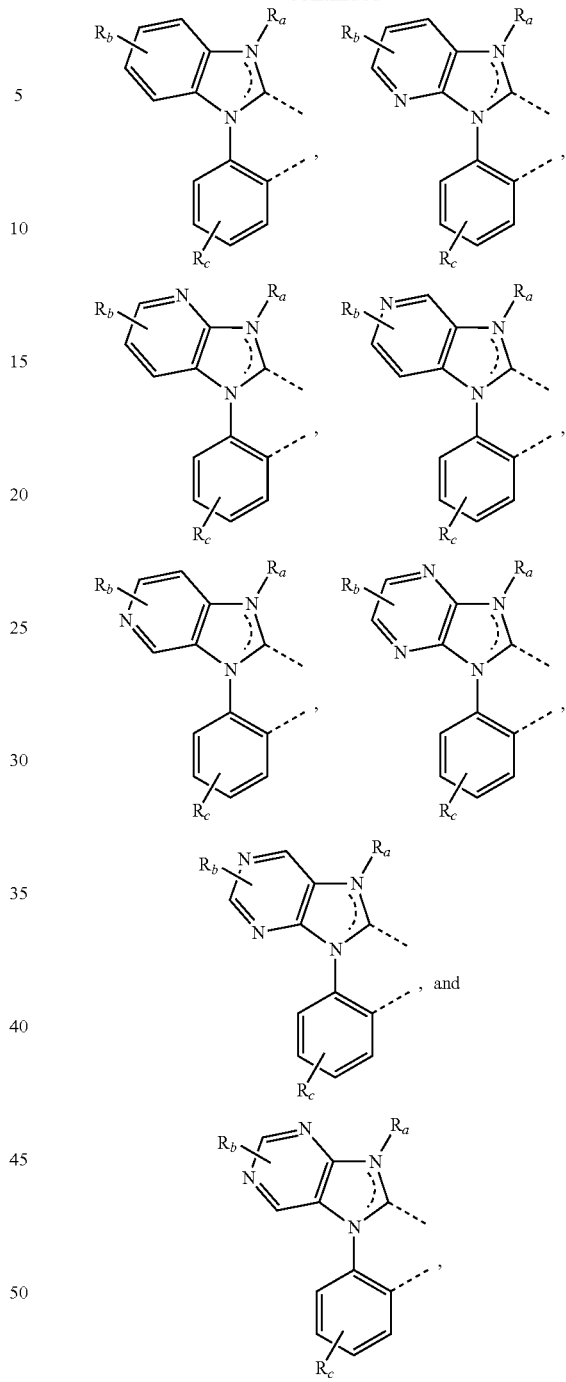

wherein $R_a$, $R_b$, and $R_c$ may represent mono, di, tri or tetra substitutions;

$R_a$, $R_b$, and $R_c$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and two adjacent substituents of $R_a$, $R_b$, and $R_c$ are optionally joined to form a fused ring.

21. The first device of claim 11, wherein the organic layer is a blocking layer and the compound having the Formula I is a blocking material in the organic layer.

22. The first device of claim 11, wherein the organic layer is an electron transporting layer and the compound having the Formula I is an electron transporting material in the organic layer.

23. The first device of claim 11, wherein the first device is a consumer product.

24. The first device of claim 11, wherein the first device is an organic light-emitting device.

25. The first device of claim 11, wherein the first device is a lighting panel.

\* \* \* \* \*